United States Patent
Brandhuber et al.

(10) Patent No.: US 9,809,578 B2
(45) Date of Patent: Nov. 7, 2017

(54) PYRAZOLYL UREA, THIOUREA, GUANIDINE AND CYANOGUANIDINE COMPOUNDS AS TRKA KINASE INHIBITORS

(71) Applicant: Array BioPharma Inc., Boulder, CO (US)

(72) Inventors: Barbara J. Brandhuber, Boulder, CO (US); Yutong Jiang, Boulder, CO (US); Gabrielle R. Kolakowski, Boulder, CO (US); Shannon L. Winski, Boulder, CO (US)

(73) Assignee: Array BioPharma Inc., Boulder, CO (US)

( * ) Notice: Subject to any disclaimer, the term of this patent is extended or adjusted under 35 U.S.C. 154(b) by 152 days.

(21) Appl. No.: 14/442,495

(22) PCT Filed: Nov. 13, 2013

(86) PCT No.: PCT/US2013/069897
§ 371 (c)(1),
(2) Date: May 13, 2015

(87) PCT Pub. No.: WO2014/078417
PCT Pub. Date: May 22, 2014

(65) Prior Publication Data
US 2016/0280690 A1  Sep. 29, 2016

Related U.S. Application Data

(60) Provisional application No. 61/725,947, filed on Nov. 13, 2012.

(51) Int. Cl.
*C07D 403/14* (2006.01)
*C07D 401/14* (2006.01)
*C07D 403/12* (2006.01)

(52) U.S. Cl.
CPC ......... *C07D 403/14* (2013.01); *C07D 401/14* (2013.01); *C07D 403/12* (2013.01)

(58) Field of Classification Search
None
See application file for complete search history.

(56) References Cited

U.S. PATENT DOCUMENTS

| | | |
|---|---|---|
| 5,849,779 A | 12/1998 | Hirota et al. |
| 5,998,424 A | 12/1999 | Galemmo, Jr. et al. |
| 6,197,798 B1 | 3/2001 | Fink et al. |
| 6,410,533 B1 | 6/2002 | Hirth et al. |
| 7,223,782 B2 | 5/2007 | Atkinson et al. |
| 7,625,915 B2 | 12/2009 | Dumas et al. |
| 8,592,454 B2 | 11/2013 | Shirai et al. |
| 9,163,017 B2 | 10/2015 | Degoey et al. |

FOREIGN PATENT DOCUMENTS

| | | |
|---|---|---|
| EP | 0761658 A1 | 12/1997 |
| EP | 1043995 B1 | 11/2006 |
| EP | 2033955 A1 | 3/2009 |
| EP | 1451160 B1 | 1/2010 |
| EP | 2336105 B9 | 9/2014 |
| JP | 2005206527 A | 8/2005 |
| WO | 9804521 A1 | 2/1998 |
| WO | 9923091 A1 | 5/1999 |
| WO | 9932110 A1 | 7/1999 |
| WO | 0039116 A1 | 7/2000 |
| WO | 0043384 A1 | 7/2000 |
| WO | 0112188 A1 | 2/2001 |
| WO | 0202525 A2 | 1/2002 |
| WO | 02088101 A2 | 11/2002 |
| WO | 02090326 A1 | 11/2002 |
| WO | 03037274 A2 | 5/2003 |
| WO | 03045920 A1 | 6/2003 |

(Continued)

OTHER PUBLICATIONS

Aisen Alzheimer's Research & Therapy (2009), vol. 1, pp. 1-6.*
Vogelstein et al. Nature Medicine (2004), vol. 10, pp. 789-799.*
Lippard. The Art of Chemistry, Nature 2002, vol. 416, pp. 587.*
Tsuzuki, Y., et al., Tetrahedron Asymmetry 12 (2001), 2989-2997.
Wadhwa, S., et al., Journal of Biosciences, 2003, 28(2), 181-188.
Wang, T., et al., Expert Opinion in Therapeutic Patents (2009) 19(3):305-319.
Woolf, C.J. et al. (1994) Neuroscience, 62, 327-331.
Yilmaz, T., et al., Cancer Biology and Therapy, 2010, 10(6), 644-653.
Zahn, P.K. et al. (2004) J. Pain, 5, 157-163.
Patent Cooperation Treaty, International Searching Authority, Search Report and Written Opinion for PCT/US2013/069897, dated May 28, 2015, 8 Pages.

(Continued)

*Primary Examiner* — Kendra D Carter
*Assistant Examiner* — Taina D Matos Negron
(74) *Attorney, Agent, or Firm* — Viksnins Harris Padys Malen LLP; Sarah S. Mastous

(57) ABSTRACT

Compounds of Formula I: or stereoisomers, tautomers, or pharmaceutically acceptable salts, solvates or prodrugs thereof, wherein Ring A, Ring C and X are as defined herein, are inhibitors of TrkA kinase and are useful in the treatment of diseases which can be treated with a TrkA kinase inhibitor such as pain, cancer, inflammation/inflammatory diseases, neurodegenerative diseases, certain infectious diseases, Sjogren's syndrome, endometriosis, diabetic peripheral neuropathy, prostatitis or pelvic pain syndrome.

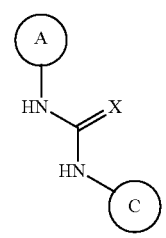

18 Claims, No Drawings

(56) References Cited

FOREIGN PATENT DOCUMENTS

| | | |
|---|---|---|
| WO | 03051275 A2 | 6/2003 |
| WO | 2004005262 A2 | 1/2004 |
| WO | 2004032870 A2 | 4/2004 |
| WO | 2004060305 A2 | 7/2004 |
| WO | 2004060306 A2 | 7/2004 |
| WO | 2004061084 A2 | 7/2004 |
| WO | 2004111009 A1 | 12/2004 |
| WO | 2005024755 A2 | 3/2005 |
| WO | 2005048948 A2 | 6/2005 |
| WO | 2005110994 A2 | 11/2005 |
| WO | 2006014290 A2 | 2/2006 |
| WO | 2006068591 A1 | 6/2006 |
| WO | 2006070198 A1 | 7/2006 |
| WO | 2006071940 A2 | 7/2006 |
| WO | 2006081034 A2 | 8/2006 |
| WO | 2006123257 A2 | 11/2006 |
| WO | 2007008917 A2 | 1/2007 |
| WO | 2007059202 A2 | 5/2007 |
| WO | 2007061882 A2 | 5/2007 |
| WO | 2007064872 A2 | 6/2007 |
| WO | 2008016811 A2 | 2/2008 |
| WO | 2008021859 A1 | 2/2008 |
| WO | 2008033999 A2 | 3/2008 |
| WO | 2008034008 A2 | 3/2008 |
| WO | 2008046003 A2 | 4/2008 |
| WO | 2008131276 A1 | 10/2008 |
| WO | 2008150899 A1 | 12/2008 |
| WO | 2009140128 A2 | 11/2009 |
| WO | 2010032856 A1 | 3/2010 |
| WO | 2010033941 A1 | 3/2010 |
| WO | 2010040663 A1 | 4/2010 |
| WO | 2010048314 A1 | 4/2010 |
| WO | 2010059719 A2 | 5/2010 |
| WO | 2010075376 A2 | 7/2010 |
| WO | 2010077680 A2 | 7/2010 |
| WO | 2010104488 A1 | 9/2010 |
| WO | 2010125799 A1 | 11/2010 |
| WO | 2011006074 A1 | 1/2011 |
| WO | 2011032291 A1 | 3/2011 |
| WO | 2011146336 A1 | 11/2011 |
| WO | 2012158413 A2 | 11/2012 |
| WO | 2013063214 A1 | 5/2013 |
| WO | 2013096226 A1 | 6/2013 |
| WO | 2013176970 A1 | 11/2013 |
| WO | 2014052563 A1 | 4/2014 |
| WO | 2014052566 A1 | 4/2014 |
| WO | 2014078322 A1 | 5/2014 |
| WO | 2014078323 A1 | 5/2014 |
| WO | 2014078325 A1 | 5/2014 |
| WO | 2014078328 A1 | 5/2014 |
| WO | 2014078331 A1 | 5/2014 |
| WO | 2014078372 A1 | 5/2014 |
| WO | 2014078378 A1 | 5/2014 |
| WO | 2014078408 A1 | 5/2014 |
| WO | 2014078417 A1 | 5/2014 |
| WO | 2014078454 A1 | 5/2014 |
| WO | 2015039333 A1 | 3/2015 |
| WO | 2015042085 A2 | 3/2015 |

OTHER PUBLICATIONS

Adriaenssens, E., et al. Cancer Res (2008) 68:(2) 346-351.
Asaumi, K., et al., Bone (2000) 26(6) 625-633.
Bardelli, A., Science 2003, 300, 949.
Bhattacharya, S. K., et al., Bioorganic & Medicinal Chemistry Letters (2012) 22(24) 7523-7592.
Bouhana, Karyn S., et al., "Comparison of Analgesic Effects of an Allosteric Inhibitor of TrkA to that of an ATP site inhibitor of the pan-Trk axis in a Rodent Model of Inflammatory Pain", Gordon Conference, Salve Regina University, Newport, RI, Jun. 7, 2011.
Brodeur, G. M., Nat. Rev. Cancer 2003, 3, 203-216.
Bruno, O., Bioorganic & Medicinal Chemistry (2009) 17, 3379-3387.
Burger, K., et al., Synthesis (1990) vol. 4, 360-365.
Chambers, L. J., et al., Bioorganic & Medicinal Chemistry Letters (2010) 20(10) 3161-3164.
Davidson. B., et al., Clin. Cancer Res. 2003, 9, 2248-2259.
Davies, Stephen G., et al., Asymmetric synthesis of 3,4-anti- and 3,4-syn-substituted aminopyrrolidines via lithium amide conjugate addition, Org. Biomol. Chem., 2007, 5, 1961-1969.
Delafoy, L. et al. (2003) Pain 105, 489-497.
Demelo-Jorge, M. et al., Cell Host & Microbe (2007) 1(4), 251-261.
Dimola, F. F, et. al., Gut (2000) 46(5), 670-678.
Dou, Y.-C., et. al. Archives of Dermatological Research (2006) 298(1), 31-37.
Du, et al., World Journal of Gastroenterology, 2003, 9(7), 1431-1434.
Eguchi, M., et al., Blood 1999, 93 (4), pp. 1355-1363.
El Haddad, M., et al., J. Heterocyclic Chem., (2000) 37, 1247-1252.
Eliav, E. et al., Pain 79, 255-264 (1999).
Euthus, D.M., et al., Cancer Cell 2002, 2 (5), pp. 347-348.
Freund-Michel, V; Frossard, N., Pharmacology & Therapeutics (2008) 117(1), 52-76.
Greco, A., et al., Molecular and Cellular Endocrinology 2010, 321 (1), pp. 44-49.
Gruber-Olipitz, M., et al., Journal of Proteome Research 2008, 7 (5), pp. 1932-1944.
Gwak, Y. S. et al. (2003) Neurosci. Lett. 336, 117-120.
Han, S., et al., J. Biological Chem., (2009), 284(19) 13199-13201.
Herzberg, U. et al., Neuroreport 1997; 8:1613-1618.
Hu, Vivian Y; et al., The Journal of Urology (2005), 173(3), 1016-1021.
Jaggar, S. I. et al., Br. J. Anaesth. (1999) 83, 442-448.
Jin, W., et al., Carcinogenesis (2010) 31 (11), pp. 1939-1947.
Kaymakcioglu, B.K, et al., European Journal of Pharmaceutical Sciences (2005) 26(1), 97-103.
Lamb, K. et al. (2003) Neurogastroenterol. Motil. 15, 355-361.
Li, L. et al. (2003) Mol. Cell. Neurosci. 23, 232-250.
Li, Y.-G., et al., Chinese Journal of Cancer Prevention and Treatment, 2009, 16 (6), pp. 428-430 (with English Abstract).
Ma, Q. P. and Woolf, C. J. NeuroReport (1997) 8, 807-810.
Mantyh, Patrick W., et al., Anesthesiology, vol. 115, No. 1, Jul. 2011, 189-204.
McCarthy, C. and Walker, E., Expert Opin. Ther. Patents (2014) 24(7):731-744.
McMahon, S.B. et al., (1995) Nat. Med. 1, 774-780.
Meyer, J. et al. (2007) Leukemia, 21(10):2171-2180.
Nakagawara, A. (2001) Cancer Letters 169:107-114.
Patapoutian, A. et al., Current Opinion in Neurobiology, 2001, 11, 272-280.
Pierottia, M.A. and Greco A., (2006) Cancer Letters 232:90-98.
Pinski, J. et al., Cancer Research, (2002) 62:986-989.
Ramer, M. S. and Bisby, M. A. (1999) Eur. J. Neurosci. 11, 837-846.
Raychaudhuri, S. P., et al., J. Investigative Dermatology (2004) 122(3), 812-819.
Ricci A, et al., American Journal of Respiratory Cell and Molecular Biology, 2001, 25(4), pp. 439-446.
Ro, L. S. et al., Pain, Feb. 1999; 79(2-3):265-274.
Shelton, D. L. et al. (2005) Pain, 116, 8-16.
Theodosiou, M. et al. (1999) Pain, 81, 245-255.
Truzzi, F., et al., Dermato-Endocrinology, 2011, 3(1), 32-36.

\* cited by examiner

PYRAZOLYL UREA, THIOUREA, GUANIDINE AND CYANOGUANIDINE COMPOUNDS AS TRKA KINASE INHIBITORS

RELATED APPLICATIONS

This application is a 371 filing of PCT Application No. PCT/US2013/069897, filed Nov. 13, 2013, which claims priority to U.S. Provisional Application Ser. No. 61/725,947, filed Nov. 13, 2012, each of which is incorporated herein by reference in its entirety.

BACKGROUND OF THE INVENTION

The present invention relates to novel compounds, to pharmaceutical compositions comprising the compounds, to processes for making the compounds and to the use of the compounds in therapy. More particularly, it relates to pyrazolyl urea, thiourea, guanidine and cyanoguanidine compounds which exhibit TrkA kinase inhibition, and which are useful in the treatment of pain, cancer, inflammation/inflammatory diseases, neurodegenerative diseases, certain infectious diseases, Sjogren's syndrome, endometriosis, diabetic peripheral neuropathy, prostatitis or pelvic pain syndrome.

The current treatment regimens for pain conditions utilize several classes of compounds. The opioids (such as morphine) have several drawbacks including emetic, constipatory and negative respiratory effects, as well as the potential for addictions. Non-steroidal anti-inflammatory analgesics (NSAIDs, such as COX-1 or COX-2 types) also have drawbacks including insufficient efficacy in treating severe pain. In addition, COX-1 inhibitors can cause ulcers of the mucosa. Accordingly, there is a continuing need for new and more effective treatments for the relief of pain, especially chronic pain.

Trk's are the high affinity receptor tyrosine kinases activated by a group of soluble growth factors called neurotrophins (NT). The Trk receptor family has three members: TrkA, TrkB and TrkC. Among the neurotrophins are (i) nerve growth factor (NGF) which activates TrkA, (ii) brain-derived neurotrophic factor (BDNF) and NT-4/5 which activate TrkB and (iii) NT3 which activates TrkC. Trk's are widely expressed in neuronal tissue and are implicated in the maintenance, signaling and survival of neuronal cells (Patapoutian, A. et al., *Current Opinion in Neurobiology*, 2001, 11, 272-280).

Inhibitors of the Trk/neurotrophin pathway have been demonstrated to be effective in numerous pre-clinical animal models of pain. For example, antagonistic NGF and TrkA antibodies such as RN-624 have been shown to be efficacious in inflammatory and neuropathic pain animal models (Woolf, C. J. et al. (1994) *Neuroscience* 62, 327-331; Zahn, P. K. et al. (2004) *J. Pain* 5, 157-163; McMahon, S. B. et al., (1995) *Nat. Med.* 1, 774-780; Ma, Q. P. and Woolf, C. J. (1997) *NeuroReport* 8, 807-810; Shelton, D. L. et al. (2005) *Pain* 116, 8-16; Delafoy, L. et al. (2003) *Pain* 105, 489-497; Lamb, K. et al. (2003) *Neurogastroenterol. Motil.* 15, 355-361; Jaggar, S. I. et al. (1999) *Br. J Anaesth.* 83, 442-448) and neuropathic pain animal models (Ramer, M. S. and Bisby, M. A. (1999) *Eur. J. Neurosci.* 11, 837-846; Ro, L. S. et al. (1999); Herzberg, U. et al., *Pain* 79, 265-274 (1997) *Neuroreport* 8, 1613-1618; Theodosiou, M. et al. (1999) *Pain* 81, 245-255; Li, L. et al. (2003) *Mol. Cell. Neurosci.* 23, 232-250; Gwak, Y. S. et al. (2003) *Neurosci. Lett.* 336, 117-120).

It has also been shown that NGF secreted by tumor cells and tumor invading macrophages directly stimulates TrkA located on peripheral pain fibers. Using various tumor models in both mice and rats, it was demonstrated that neutralizing NGF with a monoclonal antibody inhibits cancer related pain to a degree similar or superior to the highest tolerated dose of morphine. Because TrkA kinase may serve as a mediator of NGF driven biological responses, inhibitors of TrkA and/or other Trk kinases may provide an effective treatment for chronic pain states.

Recent literature has also shown that overexpression, activation, amplification and/or mutation of Trk kinases are associated with many cancers including neuroblastoma (Brodeur, G. M., *Nat. Rev. Cancer* 2003, 3, 203-216), ovarian (Davidson. B., et al., *Clin. Cancer Res.* 2003, 9, 2248-2259), colorectal cancer (Bardelli, A., *Science* 2003, 300, 949), melanoma (Truzzi, F., et al., *Dermato-Endocrinology* 2008, 3 (1), pp. 32-36), head and neck cancer (Yilmaz, T., et al., *Cancer Biology and Therapy* 2010, 10 (6), pp. 644-653), gastric carcinoma (Du, J. et al., *World Journal of Gastroenterology* 2003, 9 (7), pp. 1431-1434), lung carcinoma (Ricci A., et al., *American Journal of Respiratory Cell and Molecular Biology* 25 (4), pp. 439-446), breast cancer (Jin, W., et al., *Carcinogenesis* 2010, 31 (11), pp. 1939-1947), Glioblastoma (Wadhwa, S., et al., *Journal of Biosciences* 2003, 28 (2), pp. 181-188), medulloblastoma (Gruber-Olipitz, M., et al., *Journal of Proteome Research* 2008, 7 (5), pp. 1932-1944), secratory breast cancer (Euthus, D. M., et al., *Cancer Cell* 2002, 2 (5), pp. 347-348), salivary gland cancer (Li, Y.-G., et al., *Chinese Journal of Cancer Prevention and Treatment* 2009, 16 (6), pp. 428-430), papillary thyroid carcinoma (Greco, A., et al., *Molecular and Cellular Endocrinology* 2010, 321 (1), pp. 44-49) and adult myeloid leukemia (Eguchi, M., et al., *Blood* 1999, 93 (4), pp. 1355-1363). In preclinical models of cancer, non-selective small molecule inhibitors of TrkA, B and C were efficacious in both inhibiting tumor growth and stopping tumor metastasis (Nakagawara, A. (2001) *Cancer Letters* 169:107-114; Meyer, J. et al. (2007) *Leukemia*, 1-10; Pierottia, M. A. and Greco A., (2006) *Cancer Letters* 232:90-98; Eric Adriaenssens, E., et al. *Cancer Res* (2008) 68:(2) 346-351).

In addition, inhibition of the neurotrophin/Trk pathway has been shown to be effective in treatment of pre-clinical models of inflammatory diseases with NGF antibodies or non-selective small molecule inhibitors of TrkA. For example, inhibition of the neurotrophin/Trk pathway has been implicated in preclinical models of inflammatory lung diseases including asthma (Freund-Michel, V; Frossard, N., *Pharmacology & Therapeutics* (2008) 117(1), 52-76), interstitial cystitis (Hu Vivian Y; et. al. *The Journal of Urology* (2005), 173(3), 1016-21), bladder pain syndrome (Liu, H.-T., et al., (2010) *BJU International*, 106 (11), pp. 1681-1685), inflammatory bowel diseases including ulcerative colitis and Crohn's disease (Di Mola, F. F, et. al., *Gut* (2000) 46(5), 670-678) and inflammatory skin diseases such as atopic dermatitis (Dou, Y.-C., et. al. *Archives of Dermatological Research* (2006) 298(1), 31-37), eczema and psoriasis (Raychaudhuri, S. P., et al., *J. Investigative Dermatology* (2004) 122(3), 812-819).

The TrkA receptor is also thought to be critical to the disease process in the infection of the parasitic infection of *Trypanosoma cruzi* (Chagas disease) in human hosts (de Melo-Jorge, M. et al., *Cell Host & Microbe* (2007) 1(4), 251-261).

Trk inhibitors may also find use in treating disease related to an imbalance of the regulation of bone remodeling, such as osteoporosis, rheumatoid arthritis, and bone metastases. Bone metastases are a frequent complication of cancer, occurring in up to 70 percent of patients with advanced breast or prostate cancer and in approximately 15 to 30 percent of patients with carcinoma of the lung, colon, stomach, bladder, uterus, rectum, thyroid, or kidney. Osteolytic metastases can cause severe pain, pathologic fractures, life-threatening hypercalcemia, spinal cord compression, and other nerve-compression syndromes. For these reasons, bone metastasis is a serious and costly complication of cancer. Therefore, agents that can induce apoptosis of proliferating osteoblasts would be highly advantageous. Expression of TrkA receptors has been observed in the bone-forming area in mouse models of bone fracture (K. Asaumi, et al., *Bone* (2000) 26(6) 625-633). In addition, localization of NGF was observed in almost all bone-forming cells (K. Asaumi, et al.). Recently, it was demonstrated that a Trk inhibitor inhibits the tyrosine signaling activated by neurotrophins binding to all three of the Trk receptors in human hFOB osteoblasts (J. Pinski, et al., (2002) 62, 986-989). These data support the rationale for the use of Trk inhibitors for the treatment of bone remodeling diseases, such as bone metastases in cancer patients.

Trk inhibitors may also find use in treating diseases and disorders such as Sjogren's syndrome (Fauchais, A. L., et al., (2009) Scandinavian Journal of Rheumatology, 38(1), pp. 50-57), endometriosis (Barcena De Arellano, M. L., et al., (2011) Reproductive Sciences, 18(12), pp. 1202-1210; Barcena De Arellano, et al., (2011) Fertility and Sterility, 95(3), pp. 1123-1126; Cattaneo, A., (2010) Current Opinion in Molecular Therapeutics, 12(1), pp. 94-106), diabetic peripheral neuropathy (Kim, H. C., et al., (2009) Diabetic Medicine, 26 (12), pp. 1228-1234; Siniscalco, D., et al., (2011) Current Neuropharmacology, 9(4), pp. 523-529; Ossipov, M. H., (2011) Current Pain and Headache Reports, 15(3), pp. 185-192), and prostatitis and pelvic pain syndrome (Watanabe, T., et al., (2011) BJU International, 108 (2), pp. 248-251; and Miller, L. J., et al., (2002) Urology, 59(4), pp. 603-608).

Several classes of small molecule inhibitors of Trk kinases said to be useful for treating pain or cancer are known (*Expert Opin. Ther. Patents* (2009) 19(3), 305-319).

SUMMARY OF THE INVENTION

It has now been found that pyrrolidinyl urea, thiourea, guanidine and cyanoguanidine compounds are inhibitors of TrkA, and useful for treating disorders and diseases such as pain, including chronic and acute pain. Compounds of the invention useful in the treatment of multiple types of pain including inflammatory pain, neuropathic pain, and pain associated with cancer, surgery, or bone fracture. In addition, compounds of the invention are useful for treating cancer, inflammation or inflammatory diseases, neurodegenerative diseases, certain infectious diseases, Sjogren's syndrome, endometriosis, diabetic peripheral neuropathy, prostatitis or pelvic pain syndrome, and diseases related to an imbalance of the regulation of bone remodeling, such as osteoporosis, rheumatoid arthritis, and bone metastases.

More specifically, provided herein are compounds of Formula I:

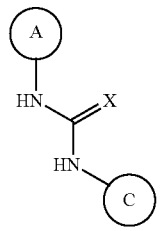

I or stereoisomers, tautomers, or pharmaceutically acceptable salts, solvates or prodrugs thereof, wherein Ring A, Ring C and X are as defined herein.

Another aspect of the present invention provides methods of treating a disease or disorder modulated by TrkA, comprising administering to a mammal in need of such treatment an effective amount of a compound of this invention or a stereoisomer, solvate or pharmaceutically acceptable salt thereof. In one embodiment, the disease and disorders include chronic and acute pain, including but not limited to inflammatory pain, neuropathic pain, and pain associated with cancer, surgery, or bone fracture. In another embodiment, the disease and disorders include, but are not limited to, cancer, inflammation or inflammatory diseases, neurodegenerative diseases, certain infectious diseases, Sjogren's syndrome, endometriosis, diabetic peripheral neuropathy, prostatitis or pelvic pain syndrome, and diseases related to an imbalance of the regulation of bone remodeling, such as osteoporosis, rheumatoid arthritis, and bone metastases. In one embodiment, the treatment includes treating the mammal with a compound of this invention in combination with an additional therapeutic agent.

Another aspect of the present invention provides a pharmaceutical composition comprising a compound of the present invention or a pharmaceutically acceptable salt thereof.

Another aspect of the present invention provides the compounds of the present invention for use in therapy.

Another aspect of the present invention provides the compounds of the present invention for use in the treatment of disease and disorders such as chronic and acute pain, including but not limited to inflammatory pain, neuropathic pain, and pain associated with cancer, surgery, or bone fracture. Another aspect of the present invention provides the compounds of the present invention for use in the treatment of disease and disorders selected from cancer, inflammation or inflammatory diseases, neurodegenerative diseases, certain infectious diseases, Sjogren's syndrome, endometriosis, diabetic peripheral neuropathy, prostatitis or pelvic pain syndrome, and diseases related to an imbalance of the regulation of bone remodeling, such as osteoporosis, rheumatoid arthritis, and bone metastases.

Another aspect of the present invention provides the use of a compound of this invention in the manufacture of a medicament for the treatment of disease and disorders such as chronic and acute pain including, but not limited to, inflammatory pain, neuropathic pain, and pain associated with cancer, surgery, or bone fracture.

Another aspect of the present invention provides the use of a compound of this invention in the manufacture of a medicament for the treatment of disease and disorders selected from cancer, inflammation or inflammatory diseases, neurodegenerative diseases, certain infectious diseases, Sjogren's syndrome, endometriosis, diabetic peripheral neuropathy, prostatitis or pelvic pain syndrome, and diseases related to an imbalance of the regulation of bone remodeling, such as osteoporosis, rheumatoid arthritis, and bone metastases.

Another aspect of the present invention provides intermediates for preparing compounds of Formula I.

Another aspect of the present invention includes methods of preparing, methods of separation, and methods of purification of the compounds of this invention.

DETAILED DESCRIPTION OF THE INVENTION

Provided herein are compounds, and pharmaceutical formulations thereof, that are useful in the treatment of diseases, conditions and/or disorders modulated by TrkA.

A representative compound of the invention (See Table B below), was found to be highly selective for TrkA over a panel of about 230 other kinases at 10 μM concentration. In addition, compounds of the invention such as those shown in Table A below, were found to be at least 1000 fold more selective for TrkA versus p38α.

One embodiment provides a compound of Formula I:

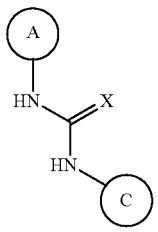

I or stereoisomers, tautomers, or pharmaceutically acceptable salts, solvates or prodrugs thereof, wherein:

X is O, S, NH or N—CN;

Ring A is

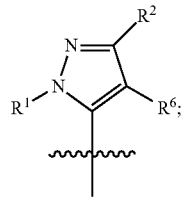

$R^1$ is phenyl optionally substituted with one or more substituents independently selected from halogen and (1-3C)alkyl;

$R^2$ is (1-3C)alkyl [optionally substituted with 1 to 5 fluoros] or (3-4C)cycloalkyl [optionally substituted with one or two fluoros];

$R^6$ is H or $CH_3$;

Ring C is formula C-1 or C-2

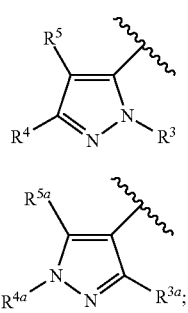

$R^3$ is (1-6C)alkyl, hydroxy(1-6C)alkyl, $Ar^2$, $hetCyc^1$, (3-7C)cycloalkyl or $hetAr^2$;

$Ar^2$ is phenyl optionally substituted with one or more substituents independently selected from halogen and (1-6C)alkyl;

$hetCyc^1$ is a 5-6-membered saturated or partially unsaturated heterocyclic ring having 1-2 ring heteroatoms independently selected from N and O;

$hetAr^2$ is a 5-6 membered heteroaryl ring having 1-3 ring heteroatoms independently selected from N, O and S optionally substituted with one or more substituents independently selected from (1-6C)alkyl and halogen;

$R^4$ is $hetAr^4$, $hetAr^5$ or hydroxy(1-6C)alkoxy;

$hetAr^4$ is a 5-6 membered heteroaryl ring having 1-3 ring heteroatoms independently selected from N, S and O and substituted with one or more substituents independently selected from (1-6C)alkyl [optionally substituted with 1-5 fluoros], halogen, CN, hydroxy(1-6C)alkyl, (3-6C)cycloalkyl, (3-6C cycloalkyl)$CH_2$—, (3-6C cycloalkyl)C(=O)—, (1-3C alkoxy)(1-6C)alkyl, (1-6C)alkoxy, (1-6C)alkylsulfonyl, $NH_2$, (1-6C alkyl)amino, di(1-6C alkyl)amino, (1-3C trifluoro)alkoxy, fluoro(1-6C alkyl)amino, difluoro(1-6C alkyl)amino, trifluoro(1-6C alkyl)amino, and (3-4C cycloalkyl)amino;

$hetAr^5$ is a group selected from the structures:

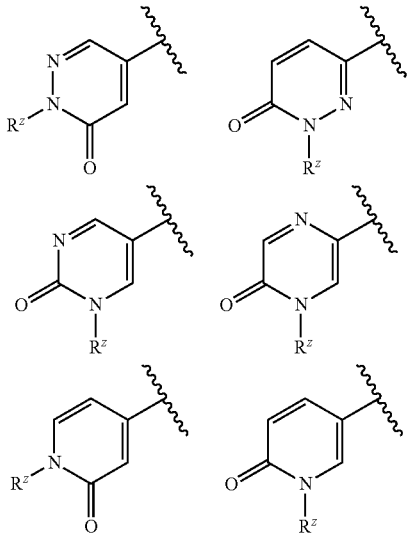

where $R^z$ is (3-4C)cycloalkyl or (1-3C)alkyl (optionally substituted with 1-3 fluoros), wherein each of said $hetAr^5$ groups is optionally further substituted with one or more substituents independently selected from F and (1-3C)alkyl optionally substituted with 1-3 fluoros;

$R^5$ is (1-6C)alkyl, monofluoro(1-6C)alkyl, difluoro(1-6C)alkyl, trifluoro(1-6C)alkyl, tetrafluoro(2-6C)alkyl, pentafluoro(2-6C)alkyl, halogen, CN, (1-4C)alkoxy, hydroxy(1-4C)alkyl, (1-3C alkoxy)(1-4C)alkyl, (1-4C alkyl)OC(=O)—, (1-6C)alkylthio, (3-4C)cycloalkyl, amino, aminocarbonyl, trifluoro(1-3C alkyl)amido, or phenyl (optionally substituted with one or more substituents independently selected from halogen, (1-6C)alkyl and (1-6C)alkoxy); or $R^4$ and $R^5$ together with the atoms to which they are attached form a 5-6 membered saturated, partially unsaturated or unsaturated carbocyclic ring optionally substituted with one or more substituents independently selected from (1-6C)alkyl, or $R^4$ and $R^5$ together with the atoms to which they are attached form 5-6 membered saturated, partially unsaturated or unsaturated heterocyclic ring having a ring heteroatom selected from N, O or S, wherein said heterocyclic ring is optionally substituted with one or two substituents independently selected from (1-6C alkyl)C(=O)O—, (1-6C)acyl, (1-6C)alkyl and oxo, and said sulfur ring atom is optionally oxidized to S(=O) or $SO_2$;

$R^{3a}$ is hydrogen, halogen, (1-6C)alkyl, trifluoro(1-6C)alkyl, (3-6C)cycloalkyl, phenyl optionally substituted with one or more substituents independently selected from halogen and (1-6C)alkyl, or a 5-6 membered heteroaryl ring having 1-3 ring heteroatoms independently selected from N, O and S and optionally substituted with one or more substituents independently selected from (1-6C)alkyl and halogen;

$R^{4a}$ is hydrogen, (1-6C)alkyl, trifluoro(1-6C)alkyl, phenyl [optionally substituted with one or more substituents independently selected from (1-6C)alkyl, halogen, CN, $CF_3$, $CF_3O$—, (1-6C)alkoxy, (1-6Calkyl)OC(=O)—, aminocarbonyl, (1-6C)alkylthio, hydroxy(1-6C)alkyl, (1-6C alkyl)$SO_2$—, HOC(=O)— and (1-3C alkoxy)(1-3C alkyl)OC(=O)—], or a 5-6 membered heteroaryl ring having 1-3 ring heteroatoms independently selected from N, S and O and optionally substituted with 1-2 substituents independently selected from (1-6C)alkyl, hydroxy(1-6C)alkyl, trifluoro(1-6C)alkyl, (3-6C)cycloalkyl, (3-6C cycloalkyl)$CH_2$-(3-6C cycloalkyl)C(=O)—, (1-3C alkoxy)(1-6C)alkyl, (1-6C) alkoxy, (1-6C)alkylsulfonyl, $NH_2$, (1-6C alkyl)amino, di(1-6C alkyl)amino and (1-3C trifluoroalkoxy)(1-3C)trifluoroalkyl; and $R^{5a}$ is hydrogen, halogen, (1-6C)alkyl, trifluoro(1-6C)alkyl, (3-6C)cycloalkyl, phenyl optionally substituted with one or more substituents independently selected from halogen and (1-6C)alkyl, or a 5-6 membered heteroaryl ring having 1-3 ring heteroatoms independently selected from N, O and S and optionally substituted with one or more substituents independently selected from (1-6C)alkyl and halogen.

One embodiment of Formula I includes compounds of Formula I-I

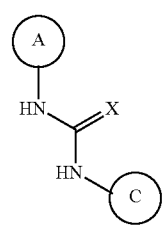

I-1 wherein:
X is O, S, NH or N—CN;
Ring A is

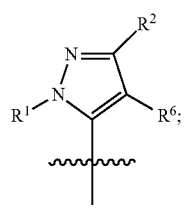

$R^1$ is phenyl optionally substituted with one or more substituents independently selected from halogen and (1-3C)alkyl;

$R^2$ is (1-3C)alkyl [optionally substituted with 1 to 5 fluoros] or (3-4C)cycloalkyl [optionally substituted with one or two fluoros];

$R^6$ is H or $CH_3$;

Ring C is formula C-1 or C-2

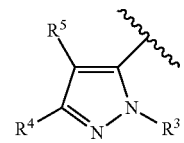

C-1

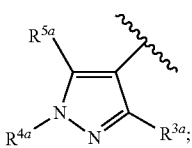

C-2

$R^3$ is (1-6C)alkyl, hydroxy(1-6C)alkyl, $Ar^2$, hetCyc$^1$, (3-7C)cycloalkyl or hetAr$^2$;

$Ar^2$ is phenyl optionally substituted with one or more substituents independently selected from halogen and (1-6C)alkyl;

hetCyc$^1$ is a 5-6-membered saturated or partially unsaturated heterocyclic ring having 1-2 ring heteroatoms independently selected from N and 0;

hetAr$^2$ is a 5-6 membered heteroaryl ring having 1-3 ring heteroatoms independently selected from N, O and S and optionally substituted with one or more substituents independently selected from (1-6C)alkyl and halogen;

$R^4$ is hetAr$^4$ or hetAr$^5$;

hetAr$^4$ is a 5-6 membered heteroaryl ring having 1-3 ring heteroatoms independently selected from N, S and O and substituted with one or more substituents independently selected from (1-6C)alkyl [optionally substituted with 1-5 fluoros], halogen, CN, hydroxy(1-6C)alkyl, (3-6C)cycloalkyl, (3-6C cycloalkyl)$CH_2$—, (3-6C cycloalkyl)C(=O)—, (1-3C alkoxy)(1-6C)alkyl, (1-6C)alkoxy, (1-6C)alkylsulfonyl, $NH_2$, (1-6C alkyl)amino, di(1-6C alkyl)amino, (1-3C trifluoro)alkoxy, fluoro(1-6C alkyl)amino, difluoro(1-6C alkyl)amino, trifluoro(1-6C alkyl)amino, and (3-4C cycloalkyl)amino;

hetAr$^5$ is a group selected from the structures:

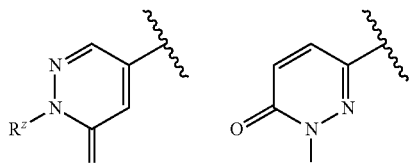

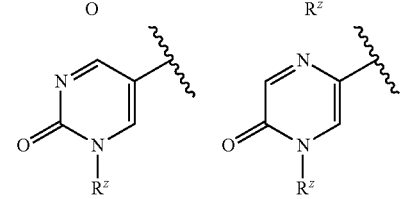

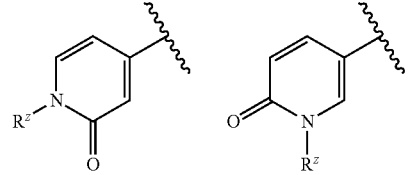

where $R^z$ is (3-4C)cycloalkyl or (1-3C)alkyl (optionally substituted with 1-3 fluoros), wherein each of said hetAr$^5$ groups is optionally further substituted with one or more substituents independently selected from F and (1-3C)alkyl optionally substituted with 1-3 fluoros;

$R^5$ is (1-6C)alkyl, monofluoro(1-6C)alkyl, difluoro(1-6C)alkyl, trifluoro(1-6C)alkyl, tetrafluoro(2-6C)alkyl, pentafluoro(2-6C)alkyl, halogen, CN, (1-4C)alkoxy, hydroxy(1-4C)alkyl, (1-3C alkoxy)(1-4C)alkyl, (1-4C alkyl)OC(=O)—, (1-6C)alkylthio, (3-4C)cycloalkyl, amino, aminocarbonyl, trifluoro(1-3C alkyl)amido, or phenyl (optionally substituted with one or more substituents independently selected from halogen, (1-6C)alkyl and (1-6C)alkoxy); or $R^4$ and $R^5$ together with the atoms to which they are attached form a 5-6 membered saturated, partially unsaturated or unsaturated carbocyclic ring optionally substituted with one or more substituents independently selected from (1-6C)alkyl, or $R^4$ and $R^5$ together with the atoms to which they are attached form 5-6 membered saturated, partially unsaturated or unsaturated heterocyclic ring having a ring heteroatom selected from N, O or S, wherein said heterocyclic ring is optionally substituted with one or two substituents independently selected from (1-6C alkyl)C(=O)O—, (1-6C)acyl, (1-6C)alkyl and oxo, and said sulfur ring atom is optionally oxidized to S(=O) or $SO_2$;

$R^{3a}$ is hydrogen, halogen, (1-6C)alkyl, trifluoro(1-6C)alkyl, (3-6C)cycloalkyl, phenyl optionally substituted with one or more substituents independently selected from halogen and (1-6C)alkyl, or a 5-6 membered heteroaryl ring having 1-3 ring heteroatoms independently selected from N, O and S and optionally substituted with one or more substituents independently selected from (1-6C)alkyl and halogen;

$R^{4a}$ is hydrogen, (1-6C)alkyl, trifluoro(1-6C)alkyl, phenyl [optionally substituted with one or more substituents independently selected from (1-6C)alkyl, halogen, CN, $CF_3$, $CF_3O$—, (1-6C)alkoxy, (1-6Calkyl)OC(=O)—, aminocarbonyl, (1-6C)alkylthio, hydroxy(1-6C)alkyl, (1-6C alkyl)$SO_2$—, HOC(=O)— and (1-3C alkoxy)(1-3C alkyl)OC(=O)—], or a 5-6 membered heteroaryl ring having 1-3 ring heteroatoms independently selected from N, S and O and optionally substituted with 1-2 substituents independently selected from (1-6C)alkyl, hydroxy(1-6C)alkyl, trifluoro(1-6C)alkyl, (3-6C)cycloalkyl, (3-6C cycloalkyl)$CH_2$-(3-6C cycloalkyl)C(=O)—, (1-3C alkoxy)(1-6C)alkyl, (1-6C) alkoxy, (1-6C)alkylsulfonyl, $NH_2$, (1-6C alkyl)amino, di(1-6C alkyl)amino and (1-3C trifluoroalkoxy)(1-3C)trifluoroalkyl; and $R^{5a}$ is hydrogen, halogen, (1-6C)alkyl, trifluoro(1-6C)alkyl, (3-6C)cycloalkyl, phenyl optionally substituted with one or more substituents independently selected from halogen and (1-6C)alkyl, or a 5-6 membered heteroaryl ring having 1-3 ring heteroatoms independently selected from N, O and S and optionally substituted with one or more substituents independently selected from (1-6C)alkyl and halogen.

It is to be understood that in instances where two or more radicals are used in succession to define a substituent attached to a structure, the first named radical is considered to be terminal and the last named radical is considered to be attached to the structure in question. Thus, for example, the radical "alkoxyalkyl" is attached to the structure in question by the alkyl group.

The terms "(1-6C)alkyl" and "(1-3C)alkyl" as used herein refer to saturated linear monovalent hydrocarbon radicals of one to six carbon atoms, and one to three carbon atoms, respectively, or a branched saturated monovalent hydrocarbon radical of three to six carbon atoms, three to four carbon atoms, or three carbon atoms, respectively. Examples include, but are not limited to, methyl, ethyl, 1-propyl, 2-propyl, 1-butyl, 2-methyl-1-propyl, 2-butyl, 2-methyl-2-propyl, 2,2-dimethylpropyl, 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, and 3,3-dimethyl-2-butyl.

"(1-6C alkyl)amino" refers to a R—NH— radical where R is (1-6C)alkyl as defined above.

"Di(1-6C alkyl)amino" refers to a $R_2$—N— radical where each R is (1-6C)alkyl as defined above.

"Difluoro(1-6C alkyl)amino" refers to a R—NH— radical where R is (1-6C)alkyl as defined above, wherein the alkyl portion is substituted with two fluoros.

"Trifluoro(1-6C alkyl)amino" refers to a R—NH— radical where R is (1-6C)alkyl as defined above, wherein the alkyl portion is substituted with two fluoros.

"(1-6C)alkoxy" refers to an RO— radical where R is (1-6C)alkyl as defined above. Examples include methoxy, ethoxy, and the like.

"(1-6C)acyl" means a RC(=O)— radical where R is a linear saturated monovalent hydrocarbon radical of one to five carbon atoms or a branched saturated monovalent hydrocarbon radical of three to five carbon atoms, e.g., methylcarbonyl, and the like.

"(1-3C Alkoxy)(1-6C)alkyl" and "(1-3C alkoxy)(1-4C)alkyl" mean a linear saturated monovalent hydrocarbon radical of one to six carbon atoms or one to four carbon atoms, or a branched saturated monovalent hydrocarbon radical of three to six carbon atoms or three to four carbon atoms, respectively, wherein one of the carbon atoms is substituted with one (1-3C)alkoxy group as defined herein.

"Amino" means a —NRR' group where R and R' are independently selected from hydrogen or (1-3C)alkyl as defined herein. Examples include $H_2N$—, $CH_3NH$—, $(CH_3)_2N$, and the like.

"Aminocarbonyl" means a RR'NCO— radical where R and R' are independently hydrogen or (1-6C)alkyl as defined herein. Examples include $H_2NCO$—, dimethylaminocarbonyl, and the like.

"(1-6C)Alkylsulfonyl" means a —$SO_2$R radical where R is (1-6C)alkyl as defined above, e.g., methylsulfonyl, and the like.

"Halogen" as used herein means F, Cl, Br or I.

"Heterocycle" refers to a saturated or partially unsaturated ring system having one or more ring heteroatoms as recited for the specific heterocyclic group, wherein the heterocycle is optionally substituted with substituents as defined for that particular heterocyclic group.

"Heteroaryl" refers to a 5-6 membered unsaturated ring system having one or more ring heteroatoms as recited for the specific heteroaryl group, wherein the heteroaryl is optionally substituted with substituents as defined for that particular heteroaryl group.

"Hydroxy(1-6C)alkyl" means a linear saturated hydrocarbon radical of one to six carbon atoms or a branched saturated monovalent hydrocarbon radical of three to six carbon atoms or three to four carbon atoms, respectively, wherein one of the carbon atoms is substituted with a hydroxy (OH) group.

"Hydroxy(1-6C)alkoxy" means a (1-6C)alkoxy group as defined above, wherein one of the carbon atoms is substituted with a hydroxyl (OH) group.

"Monofluoro(1-6C)alkyl", "difluoro(1-6C)alkyl" and "trifluoro(1-6C)alkyl" refer to a (1-6C)alkyl group as defined herein wherein one to three hydrogen atoms, respectively, is replaced by a fluoro group.

"Tetrafluoro(2-6C)alkyl" and "pentafluoro(2-6C)alkyl" refer to a linear saturated monovalent hydrocarbon radical of two to six carbon atoms or a branched saturated monovalent hydrocarbon radical of three to six carbon atoms wherein four to five hydrogen atoms, respectively, is replaced by a fluoro group.

"Trifluoro(1-3C alkyl)amido" means a (1-3C alkyl)C(=O)NH— group wherein one of the carbons is substituted with three fluoros.

"Trifluoro(1-6C)alkoxy" means a (1-6C)alkoxy group as defined herein, wherein one of the carbon atoms is substituted with three fluoros.

It should be noted that compounds of the invention may contain groups that may exist in tautomeric forms, such as heteroatom substituted heteroaryl or heterocyclic groups and the like, which are illustrated in the following general and specific examples:

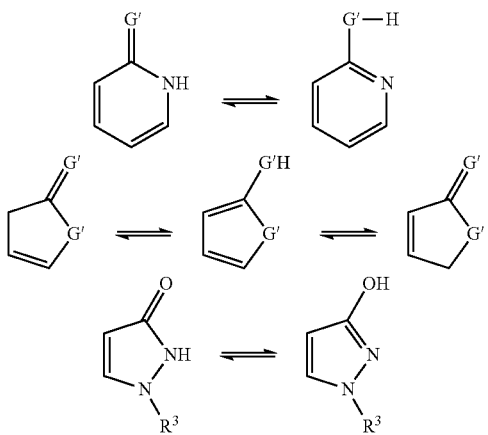

where G'=O, S, or NR, and though one form is named, described, displayed and/or claimed herein, all the tautomeric forms are intended to be inherently included in such name, description, display and/or claim.

In one embodiment of Formula I, X is O.

In one embodiment, X is S.

In one embodiment, X is NH.

In one embodiment, X is N—CN.

In one embodiment of Formula I, $R^1$ is phenyl optionally substituted with one or more substituents independently selected from halogen or (1-3C)alkyl.

In one embodiment of Formula I, $R^1$ is phenyl.

In one embodiment of Formula I, $R^2$ is (1-3C)alkyl [optionally substituted with 1 to 5 fluoros] or (3-4C)cycloalkyl [optionally substituted with one or two fluoros].

In one embodiment of Formula I, $R^2$ is (1-3C)alkyl optionally substituted with 1 to 5 fluoros. In one embodiment, $R^2$ is methyl, isopropyl, trifluoromethyl or 2,2,2-trifluoroethyl.

In one embodiment of Formula I, $R^2$ is (3-4C)cycloalkyl optionally substituted with one or two fluoros. In one embodiment, $R^2$ is cyclopropyl or 2,2-difluorocyclopropyl.

In one embodiment of Formula I, $R^6$ is H or $CH_3$. In one embodiment, $R^6$ is H. In one embodiment, $R^6$ is $CH_3$.

In one embodiment of Formula I, Ring C is formula C-1:

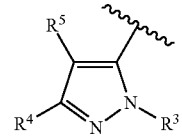

C-1 where $R^3$, $R^4$ and $R^5$ are as defined for Formula I.

In one embodiment, $R^3$ is (1-6C)alkyl. In one embodiment, $R^3$ is methyl or ethyl.

In one embodiment, $R^3$ is hydroxy(1-6C)alkyl. An example of $R^3$ is 2-hydroxyethyl.

In one embodiment, $R^3$ is $Ar^2$, where $Ar^2$ is phenyl optionally substituted with one or more substituents independently selected from halogen and (1-6C)alkyl.

In one embodiment, $R^3$ when represented by $Ar^2$ is phenyl, 2-fluorophenyl, 3-fluorophenyl, 4-fluorophenyl, 2-methylphenyl, 3-methylphenyl, 4-methylphenyl, 3-chlorophenyl, 3-chloro-4-fluorophenyl or 3-chloro-2-fluorophenyl. In one embodiment, $R^3$ when represented by $Ar^2$ is phenyl, 2-fluorophenyl, 3-fluorophenyl, 4-fluorophenyl, 2-methylphenyl, 3-methylphenyl or 4-methylphenyl. In one embodiment, $R^3$ is phenyl.

In one embodiment, $R^3$ is $hetCyc^1$, where $hetCyc^1$ is a 5-6-membered saturated or partially unsaturated heterocyclic ring having 1-2 ring heteroatoms independently selected from N and O. In one embodiment, $R^3$ is a pyrrolidinyl, tetrahydrofuranyl, imidazolidinyl, piperidinyl, piperazinyl, tetrahydropyranyl, or morpholinyl ring. In one embodiment, $R^3$ is tetrahydro-2H-pyran-4-yl.

In one embodiment, $R^3$ is (3-7C)cycloalkyl. In one embodiment $R^3$ is cyclohexyl.

In one embodiment, $R^3$ is $hetAr^2$, where $hetAr^2$ is 5-6 membered heteroaryl ring having 1-3 ring heteroatoms independently selected from N, O and S and optionally substituted with one or more substituents independently selected from (1-6C)alkyl and halogen. In one embodiment, $R^3$ is thienyl, furyl, imidazolyl, pyrazolyl, thiazolyl, isothiazolyl, oxazolyl, isoxazolyl, triazolyl, thiadiazolyl, oxadiazolyl, pyridyl, pyrimidyl, pyrazinyl, or pyridazinyl optionally substituted with one or more substituents independently selected from (1-6C)alkyl and halogen. In one embodiment, $R^3$ is pyrazolyl, pyridyl or pyridazinyl optionally substituted with one or more substituents independently selected from (1-6C)alkyl and halogen. In one embodiment, $R^3$ is pyrazolyl, pyridyl or pyridazinyl optionally substituted with (1-6C)alkyl or halogen. In one embodiment, $R^3$ when represented by $hetAr^2$ is 1-methyl-1H-pyrazol-4-yl, pyrid-2-yl, pyrid-3-yl, pyrid-4-yl, pyridazinyl or 3-chloropyrid-5-yl.

In one embodiment, $R^3$ is selected from $Ar^2$ and $hetAr^2$.

In one embodiment, $R^3$ is $Ar^2$. In one embodiment, $R^3$ is phenyl.

In one embodiment, $R^4$ is $hetAr^4$, where $hetAr^4$ is a 5-6 membered heteroaryl ring having 1-3 ring heteroatoms independently selected from N, S and O and substituted with one or more substituents independently selected from (1-6C) alkyl [optionally substituted with 1-5 fluoros], halogen, CN, hydroxy(1-6C)alkyl, (3-6C)cycloalkyl, (3-6C cycloalkyl)$CH_2$—, (3-6C cycloalkyl)C(=O)—, (1-3C alkoxy)(1-6C) alkyl, (1-6C)alkoxy, (1-6C)alkylsulfonyl, $NH_2$, (1-6C alkyl) amino, di(1-6C alkyl)amino, (1-3C trifluoro)alkoxy, fluoro (1-6C alkyl)amino, difluoro(1-6C alkyl)amino, trifluoro(1-6C alkyl)amino, and (3-4C cycloalkyl)amino.

In one embodiment, R⁴ is hetAr⁴ where hetAr⁴ is pyridyl, pyrimidinyl pyridazinyl, pyrazolyl, imidazolyl, thienyl, 1,2,4-triazolyl, 1,2,3-triazolyl, thiazolyl, oxazolyl, 1,3,4-oxadiazolyl, or 1,2,4-oxadiazolyl substituted with one or more substituents independently selected from (1-6C)alkyl, halogen, CN, hydroxy(1-6C)alkyl, trifluoro(1-6C)alkyl, difluoro(1-6C)alkyl, fluoro(1-6C)alkyl, (3-6C)cycloalkyl, (3-6C cycloalkyl)CH₂-(3-6C cycloalkyl)C(=O)—, (1-3C alkoxy)(1-6C)alkyl, (1-6C)alkoxy, (1-6C)alkylsulfonyl, NH₂, (1-6C alkyl)amino, di(1-6C alkyl)amino, (1-3C trifluoroalkoxy), fluoro(1-6C alkyl)amino, difluoro(1-6C alkyl)amino, trifluoro(1-6C alkyl)amino, and (3-4C cycloalkyl)amino.

In one embodiment, R⁴ is hetAr⁴ where hetAr⁴ is pyridyl, pyrimidinyl pyridazinyl, pyrazolyl, imidazolyl, thienyl, 1,2,4-triazolyl, 1,2,3-triazolyl, thiazolyl, oxazolyl, 1,3,4-oxadiazolyl, or 1,2,4-oxadiazolyl substituted with one or more substituents independently selected from (1-6C)alkyl, hydroxy(1-6C)alkyl, trifluoro(1-6C)alkyl, (3-6C)cycloalkyl, (3-6C cycloalkyl)CH₂— (3-6C cycloalkyl)C(=O)—, (1-3C alkoxy)(1-6C)alkyl, (1-6C)alkoxy, (1-6C)alkylsulfonyl, NH₂, (1-6C alkyl)amino, di(1-6C alkyl)amino, (1-3C trifluoroalkoxy)(1-3C)trifluoroalkyl and cyclopropylNH—.

In one embodiment, R⁴ is hetAr⁴, where hetAr⁴ is pyridyl, pyrimidinyl pyridazinyl, pyrazolyl, imidazolyl, thionyl, 1,2,4-triazolyl, 1,2,3-triazolyl, thiazolyl, oxazolyl, 1,3,4-oxadiazolyl, or 1,2,4-oxadiazolyl substituted with 1-3 substituents independently selected from fluoro, methyl, ethyl, isopropyl, cyclopropylmethyl, cyclopropyl, trifluoromethyl, 2,2,2-trifluoroethyl, methoxy, ethoxy, CN, H₂N—, (CH₃)₂N—, 2-hydroxyethyl, 2-methoxyethyl, 1-(2,2,2-trifluoroethoxy)-2,2,2-trifluoroethyl, cyclopropylcarbonyl, methylsulfonyl and cyclopropylNH—.

In one embodiment, R⁴ is hetAr⁴, where hetAr⁴ is pyridyl, pyrimidinyl or pyridazinyl substituted with 1-3 substituents independently selected from fluoro, methyl, ethyl, isopropyl, cyclopropylmethyl, cyclopropyl, trifluoromethyl, 2,2,2-trifluoroethyl, methoxy, ethoxy, CN, H₂N—, CH₃NH—, (CH₃)₂N—, and cyclopropylNH—.

In one embodiment, R⁴ is hetAr⁴, where hetAr⁴ is pyrazolyl substituted with 1-3 substituents independently selected from fluoro, methyl, ethyl, isopropyl, cyclopropylmethyl, cyclopropyl, trifluoromethyl, 2,2,2-trifluoroethyl, methoxy, ethoxy, CN, H₂N—, (CH₃)₂N—, 2-hydroxyethyl, 2-methoxyethyl, 1-(2,2,2-trifluoroethoxy)-2,2,2-trifluoroethyl, cyclopropylcarbonyl, methylsulfonyl and cyclopropylNH—.

In one embodiment, R⁴ when represented by hetAr⁴ is selected from the structures:

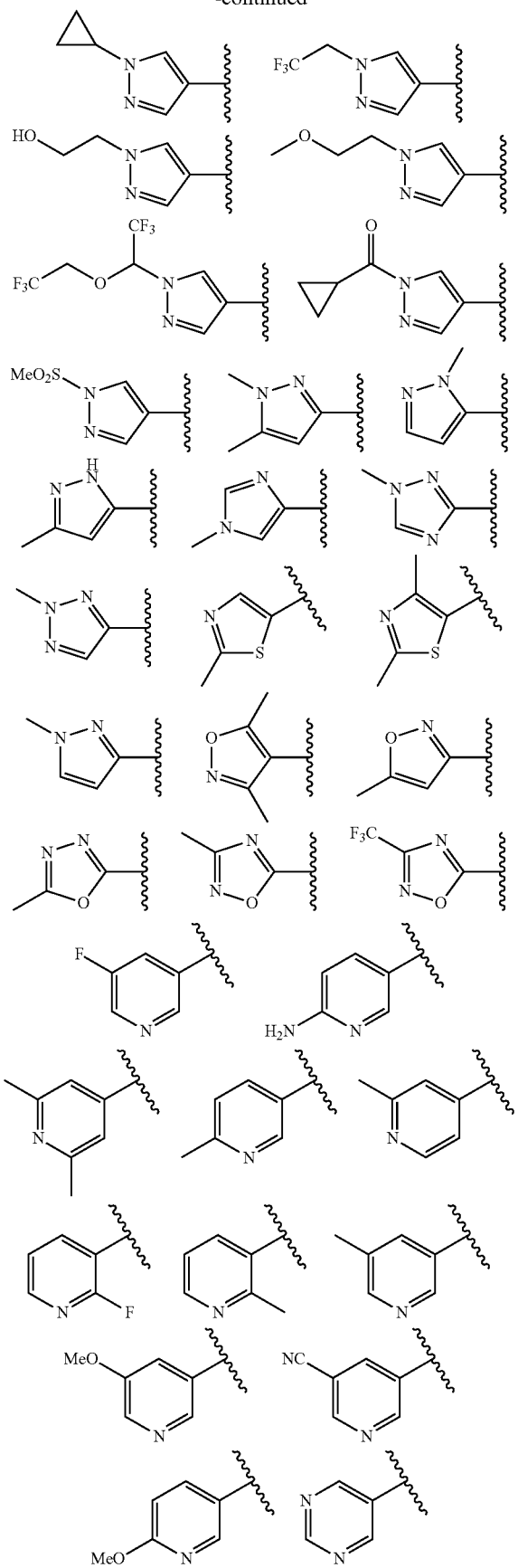

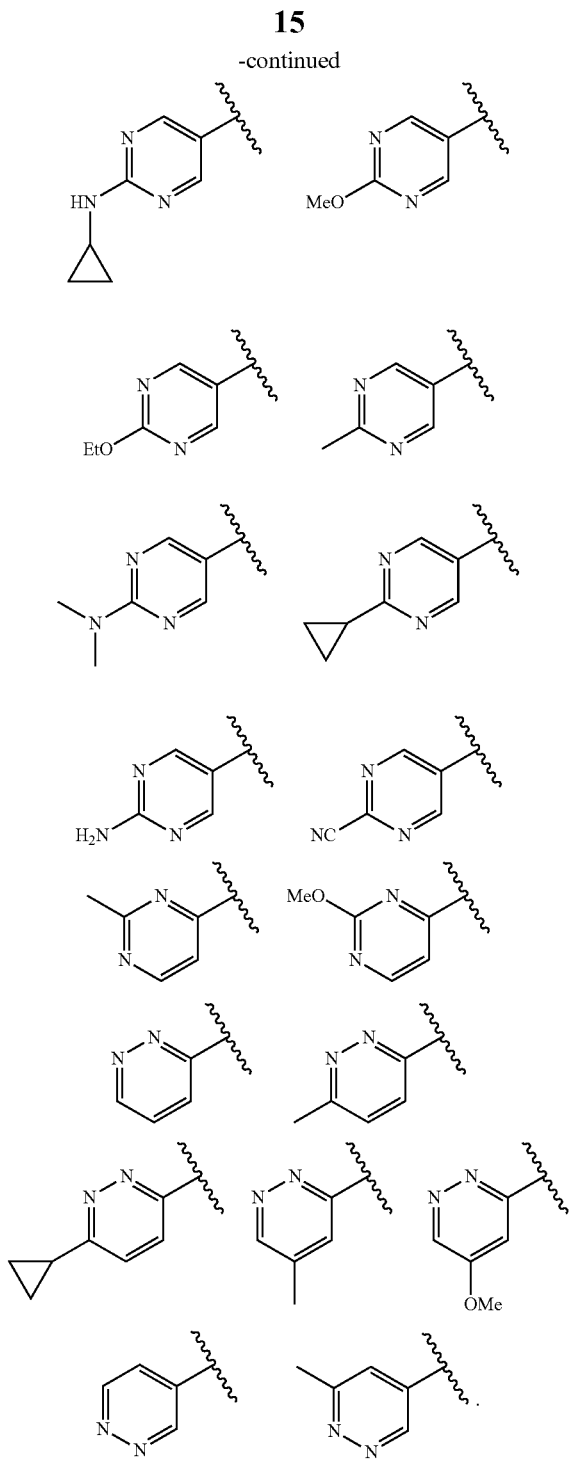

In one embodiment, R⁴ is hetAr⁵, where hetAr⁵ is a group selected from the structures:

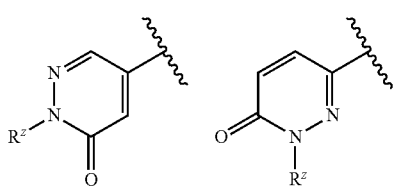

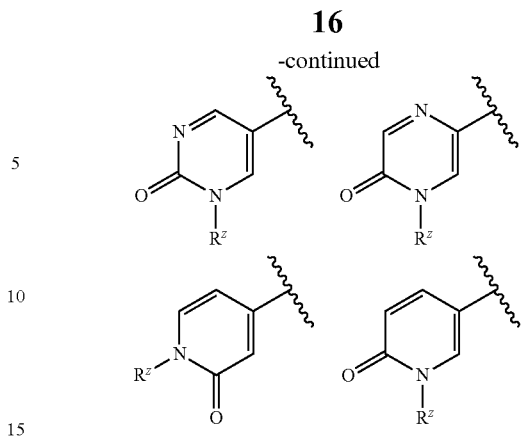

where R$^z$ is (3-4C)cycloalkyl or (1-3C)alkyl (optionally substituted with 1-3 fluoros), wherein each of said hetAr⁵ groups is optionally further substituted with one or more substituents independently selected from F and (1-3C)alkyl optionally substituted with 1-3 fluoros.

In one embodiment, R⁴ when represented by hetAr⁵ is selected from the structures:

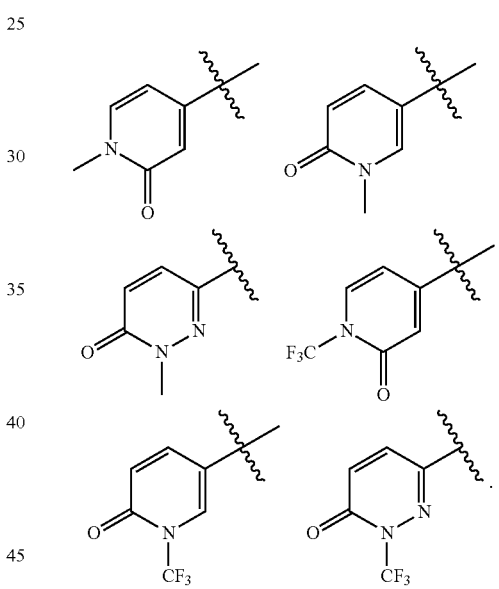

In one embodiment, R⁴ is hydroxy(1-6C)alkoxy. In one embodiment, R⁴ is 2-hydroxyethoxy.

In one embodiment, R⁵ is (1-6C)alkyl. In one embodiment, R⁵ is methyl, ethyl, propyl, isopropyl or butyl.

In one embodiment, R⁵ is monofluoro(1-6C)alkyl, difluoro(1-6C)alkyl, trifluoro(1-6C)alkyl, tetrafluoro(2-6C)alkyl or pentafluoro(2-6C)alkyl. In one embodiment, R⁵ is fluoromethyl, 2-fluoroethyl, difluoromethyl, 2,2-difluoroethyl, 1,3-difluoroprop-2-yl, trifluoromethyl, 2,2,2-trifluoroethyl, 3,3,3-trifluoropropyl, 1,1,2,2-tetrafluoropropane or 2,2,3,3,3-pentafluoropropyl.

In one embodiment, R⁵ is halogen. In one embodiment, R⁵ is F. In one embodiment, R⁵ is Cl. In one embodiment, R⁵ is Br.

In one embodiment, R⁵ is CN.

In one embodiment, R⁵ is (1-4C)alkoxy. In one embodiment, R⁵ is methoxy or ethoxy.

In one embodiment, R⁵ is hydroxy(1-4C)alkyl. In one embodiment, R⁵ is hydroxymethyl or 3-hydroxypropyl.

In one embodiment, R⁵ is (1-4C alkyl)OC(=O)—. In one embodiment, R⁵ is CH₃CH₂OC(=O)—.

In one embodiment, R⁵ is (1-6C)alkylthio. In one embodiment, R⁵ is methylthio (MeS—).

In one embodiment, R⁵ is phenyl optionally substituted with one or more substituents independently selected from halogen, (1-6C)alkyl and (1-6C)alkoxy. In one embodiment, R⁵ is phenyl optionally substituted with one or more substituents independently selected from F, Cl, methyl, ethyl, methoxy and ethoxy. In one embodiment, R⁵ is phenyl.

In one embodiment, R⁵ is (3-4C)cycloalkyl. In one embodiment, R⁵ is cyclopropyl. In one embodiment, R⁵ is cyclobutyl.

In one embodiment, R⁵ is amino. In one embodiment, R⁵ is NH₂.

In one embodiment, R⁵ is aminocarbonyl. In one embodiment, R⁵ is H₂NC(=O)—.

In one embodiment, R⁵ is trifluoro(1-3C alkyl)amido. In one embodiment, R⁵ is CF₃C(=O)NH—.

In one embodiment, R⁵ is halogen, CN, (1-6C)alkyl, (1-4C)alkoxy, hydroxy(1-4C)alkyl, or phenyl optionally substituted with one or more substituents independently selected from halogen, (1-6C)alkyl and (1-6C)alkoxy.

In one embodiment, R⁵ is selected from halogen, and (1-6C)alkyl.

In one embodiment, R⁵ is selected from methyl, Cl and Br.

In one embodiment, R⁴ and R⁵ together with the atoms to which they are attached form a 5-6 membered saturated carbocyclic ring optionally substituted with one or more substituents independently selected from (1-6C)alkyl, or R⁴ and R⁵ together with the atoms to which they are attached form a 5-6 membered saturated heterocyclic ring having a ring heteroatom selected from N, O or S, wherein said ring nitrogen atom is optionally substituted with (1-6C alkyl)C(=O)O— or (1-6C)acyl, and said sulfur ring atom is optionally oxidized to S(=O) or SO₂.

In one embodiment, R⁴ and R⁵ together with the atoms to which they are attached form a 5-6 membered saturated carbocyclic ring optionally substituted with one or more substituents independently selected from (1-6C)alkyl. In one embodiment, Ring C when R⁴ and R⁵ together with the atoms to which they are attached form a 5-6 membered saturated carbocyclic ring is selected from the structures:

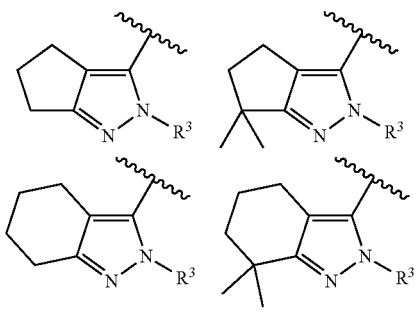

where R³ is as defined for Formula I.

In one embodiment, R⁴ and R⁵ together with the atoms to which they are attached form a 5-6 membered saturated, partially unsaturated or unsaturated heterocyclic ring having a ring heteroatom selected from N, O or S, wherein said ring N atom is optionally substituted with (1-6C alkyl)C(=O)O—, (1-6C alkyl)C(=O)—, (1-6C)alkyl or oxo, and said S ring atom is optionally oxidized to S(=O) or SO₂. In one embodiment, Ring C when R⁴ and R⁵ together with the atoms to which they are attached form a 5-6 membered saturated heterocyclic ring is selected from the structures:

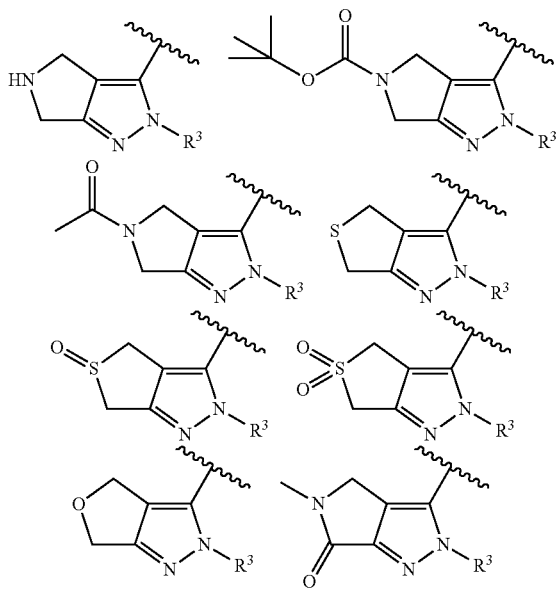

where R³ is as defined for Formula I.

In one embodiment, Ring C is formula C-2

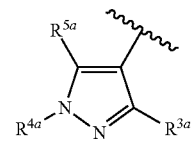

C-2 where R³ᵃ, R⁴ᵃ and R⁵ᵃ are as defined for Formula I.

In one embodiment, R³ᵃ is hydrogen.

In one embodiment, R³ᵃ is halogen.

In one embodiment, R³ᵃ is (1-6C)alkyl. In one embodiment, R³ᵃ is methyl.

In one embodiment, R³ᵃ is trifluoro(1-6C)alkyl. In one embodiment, R³ᵃ is CF₃.

In one embodiment, R³ᵃ is (3-6C)cycloalkyl. In one embodiment, R³ᵃ is cyclopropyl.

In one embodiment, R³ᵃ is phenyl optionally substituted with one or more substituents independently selected from halogen and (1-6C)alkyl. In one embodiment, R³ᵃ is phenyl, fluorophenyl or methylphenyl, for example include phenyl, 2-fluorophenyl, 3-fluorophenyl, 4-fluorophenyl, 2-methylphenyl, 3-methylphenyl, 4-methylphenyl, 3-chlorophenyl, 3-chloro-4-fluorophenyl or 3-chloro-2-fluorophenyl. In one embodiment, R³ᵃ is phenyl.

In one embodiment, R³ᵃ is a 5-6 membered heteroaryl ring having 1-3 ring heteroatoms independently selected from N, O and S and optionally substituted with one or more substituents independently selected from (1-6C)alkyl and halogen. In one embodiment, R³ᵃ is a thienyl, furyl, imidazolyl, pyrazolyl, thiazolyl, isothiazolyl, oxazolyl, isoxazolyl, triazolyl, thiadiazolyl, oxadiazolyl, pyridyl, pyrimidyl, pyrazinyl, or pyridazinyl ring optionally substituted with (1-6C)alkyl or halogen. In one embodiment, R³ᵃ is pyrazolyl, pyridyl or pyridazinyl optionally substituted with one or more substituents independently selected from (1-6C)

alkyl and halogen. In one embodiment, $R^{3a}$ is pyrazolyl, pyridyl or pyridazinyl optionally substituted with (1-6C) alkyl or halogen.

In one embodiment, $R^{4a}$ is hydrogen.

In one embodiment, $R^{4a}$ is (1-6C)alkyl. In one embodiment, $R^{4a}$ is methyl, ethyl or isopropyl.

In one embodiment, $R^{4a}$ is trifluoro(1-6C)alkyl. In one embodiment, $R^{4a}$ is 2,2,2-trifluoroethyl.

In one embodiment, $R^{4a}$ is phenyl optionally substituted with one or more substituents independently selected from (1-6C)alkyl, halogen, CN, $CF_3$, $CF_3O-$, (1-6C)alkoxy, (1-6Calkyl)OC(=O)—, aminocarbonyl, (1-6C)alkylthio, hydroxy(1-6C)alkyl, (1-6C alkyl)$SO_2$—, HOC(=O)— and (1-3C alkoxy)(1-3C alkyl)OC(=O)—. In one embodiment, $R^{4a}$ is phenyl optionally substituted with one or more substituents independently selected from methyl, F, Cl, CN, methoxy, $CH_3$OC(=O)—, aminocarbonyl, methylaminocarbonyl, dimethylaminocarbonyl, methylthio, $CH_3SO_2$—, HOC(=O)— or $CH_3OCH_2CH_2$OC(=O)—. In certain embodiments, $R^{4a}$ is phenyl optionally substituted with one or two of said substituents. In one embodiment, $R^{4a}$ is phenyl.

In one embodiment, $R^{4a}$ is a 5-6 membered heteroaryl ring having 1-3 ring heteroatoms independently selected from N, S and O and optionally substituted with 1-2 substituents independently selected from (1-6C)alkyl, hydroxy (1-6C)alkyl, trifluoro(1-6C)alkyl, (3-6C)cycloalkyl, (3-6C cycloalkyl)$CH_2$— (3-6C cycloalkyl)C(=O)—, (1-3C alkoxy)(1-6C)alkyl, (1-6C)alkoxy, (1-6C)alkylsulfonyl, $NH_2$, (1-6C alkyl)amino, di(1-6C alkyl)amino, and (1-3C trifluoroalkoxy)(1-3C)trifluoroalkyl. In one embodiment, $R^{4a}$ is pyridyl, pyrimidinyl pyridazinyl, pyrazolyl, imidazolyl, thionyl, 1,2,4-triazolyl, 1,2,3-triazolyl, thiazolyl, oxazolyl, 1,3,4-oxadiazolyl, 1,2,4-oxadiazolyl or imidazo[1,2-a]pyridinyl optionally substituted with 1-2 substituents independently selected from (1-6C)alkyl, hydroxy(1-6C) alkyl, trifluoro(1-6C)alkyl, (3-6C)cycloalkyl, (3-6C cycloalkyl)$CH_2$— (3-6C cycloalkyl)C(=O)—, (1-3C alkoxy)(1-6C)alkyl, (1-6C)alkoxy, (1-6C)alkylsulfonyl, $NH_2$, (1-6C alkyl)amino, di(1-6C alkyl)amino, and (1-3C trifluoroalkoxy)(1-3C)trifluoroalkyl. In one embodiment, $R^{4a}$ is pyrazinyl.

In one embodiment, $R^{5a}$ is as defined for Formula I.

In one embodiment, $R^{5a}$ is selected from hydrogen, halogen, (1-6C)alkyl and phenyl.

In one embodiment, $R^{5a}$ is hydrogen.

In one embodiment, $R^{5a}$ is halogen.

In one embodiment, $R^{5a}$ is (1-6C)alkyl. In one embodiment, $R^{5a}$ is methyl.

In one embodiment, $R^{5a}$ is phenyl.

In one embodiment, Ring C is formula C-2, in which $R^{3a}$ is (1-6C)alkyl, trifluoro(1-6C)alkyl or phenyl; $R^{4a}$ is (1-6C) alkyl, trifluoro(1-6C)alkyl, phenyl or pyrazinyl; and $R^{5a}$ is hydrogen, (1-6C)alkyl or phenyl.

In one embodiment, Formula I includes compounds of Formula I-a, wherein:

X is O; Ring C is C-1; $R^4$ is hetAr$^4$; and hetAr$^4$, Ring A, $R^1$, $R^2$, $R^3$, $R^4$, $R^5$ and $R^6$ are as defined for Formula I.

In one embodiment, Formula I includes compounds of Formula I-b, wherein:

X is O; Ring C is C-1; $R^4$ is hetAr$^5$; and hetAr$^5$, Ring A, $R^1$, $R^2$, $R^3$, $R^4$, $R^5$ and $R^6$ are as defined for Formula I.

It will be appreciated that certain compounds according to the invention may contain one or more centers of asymmetry and may therefore be prepared and isolated in a mixture of isomers such as a racemic mixture, or in an enantiomerically pure form.

It will further be appreciated that the compounds of Formula I or their salts may be isolated in the form of solvates, and accordingly that any such solvate is included within the scope of the present invention. For example, compounds of Formula I can exist in unsolvated as well as solvated forms with pharmaceutically acceptable solvents such as water, ethanol, and the like.

The compounds of Formula I include pharmaceutically acceptable salts thereof. In addition, the compounds of Formula I also include other salts of such compounds which are not necessarily pharmaceutically acceptable salts, and which are useful as intermediates for preparing and/or purifying compounds of Formula I and/or for separating enantiomers of compounds of Formula I. Particular examples of salts include hydrochloride salts or trifluoroacetate salts.

In one embodiment, the compounds of Formula I include the free base form of compounds of Examples 4, 5, 6, 11 and 12, or a pharmaceutically acceptable salt thereof.

In one embodiment, the compounds of Formula I include the hydrochloride salts of compounds of Examples 4, 5, 6, 11 and 12.

In one embodiment, the compounds of Formula I include the trifluoroacetate salts of compounds of Examples 4, 5, 6, 11 and 12.

The term "pharmaceutically acceptable" indicates that the substance or composition is compatible chemically and/or toxicologically, with the other ingredients comprising a formulation, and/or the mammal being treated therewith.

The present invention also provides a process for the preparation of a compound of Formula I or a salt thereof as defined herein, which comprises:

(a) for a compound of Formula I where X is O, coupling a corresponding compound having the formula II

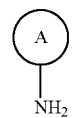

II with a corresponding compound having the formula III

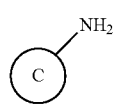

III in the presence carbonyldiimidazole or triphosgene and a base; or (b) for a compound of Formula I where X is S, coupling a corresponding compound having the formula II

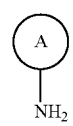

II with a corresponding compound of formula III

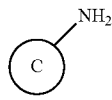

in the presence di(1H-imidazol-2-yl)methanethione and a base; or (c) for a compound of Formula I where X is O, coupling a corresponding compound having the formula II

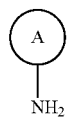

with a corresponding compound having the formula IV

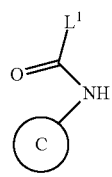

where $L^1$ is a leaving group, in the presence of a base; or (d) for a compound of Formula I where X is O, coupling a corresponding compound having the formula V

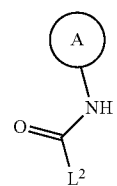

where $L^2$ is a leaving group, with a corresponding compound having the formula III

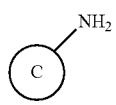

in the presence of a base; or (e) for a compound of Formula I where X is O, activating a corresponding compound having the formula VI

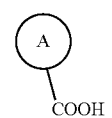

with diphenylphosphoryl azide followed by coupling the activated intermediate with a corresponding compound having the formula III

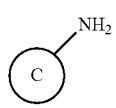

in the presence a base; or (f) for a compound of Formula I where X is O, coupling a corresponding compound having the formula II

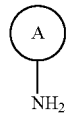

with a corresponding compound having the formula VII

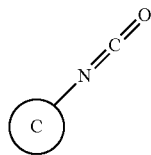

in the presence of a base; or (g) for a compound of Formula I where X is O, coupling a corresponding compound having the formula VIII

with a corresponding compound having the formula III

in the presence of a base; and optionally removing protecting groups and optionally preparing a pharmaceutically acceptable salt thereof.

In the above methods, the term "corresponding" means that the definitions for the "corresponding compound" are as defined for Formula I unless stated otherwise.

Referring to method (a), the base may be an amine base, such as triethylamine or diisopropylethylamine. Suitable solvents include dichloromethane, dichloroethane, THF, DMA and DMF. The reaction is conveniently performed at ambient temperature.

Referring to method (b), the base may be an amine base, such as triethylamine or diisopropylethylamine. Suitable solvents include dichloromethane, dichloroethane, THF, DMA and DMF. The reaction is conveniently performed at ambient temperature.

Referring to method (c), the leaving group may be, for example, phenoxy or 4-nitrophenoxy. The base may be an amine base, such as triethylamine or diisopropylethylamine. Suitable solvents include DMA, DMF and DCE. The reaction is conveniently performed at ambient temperature or elevated temperatures.

Referring to method (d), the leaving group may be, for example, phenoxy or 4-nitrophenoxy. The base may be an amine base, such as triethylamine or diisopropylethylamine. Suitable solvents include DCE, DMA and DMF. The reaction is conveniently performed at ambient temperature.

Referring to method (e), the base may be an amine base, such as triethylamine or diisopropylethylamine. Suitable solvents include toluene and DMF. The reaction is conveniently performed at elevated temperatures, for example the reflux temperature of the solvent.

Referring to methods (f) and (g), the base may be an amine base, such as triethylamine or diisopropylethylamine. Suitable solvents include DCM, DCE, DMF and THF. The reaction is conveniently performed at temperatures between about 0° C. and ambient temperature.

Amine groups in compounds described in any of the above methods may be protected with any convenient amine protecting group, for example as described in Greene & Wuts, eds., "Protecting Groups in Organic Synthesis", $2^{nd}$ ed. New York; John Wiley & Sons, Inc., 1991. Examples of amine protecting groups include acyl and alkoxycarbonyl groups, such as t-butoxycarbonyl (BOC) and [2-(trimethylsilyl)ethoxy]methyl (SEM). Likewise, carboxyl groups may be protected with any convenient carboxyl protecting group, for example as described in Greene & Wuts, eds., "Protecting Groups in Organic Synthesis", $2^{nd}$ ed. New York; John Wiley & Sons, Inc., 1991. Examples of carboxyl protecting groups include (1-6C)alkyl groups, such as methyl, ethyl and t-butyl. Alcohol groups may be protected with any convenient alcohol protecting group, for example as described in Greene & Wuts, eds., "Protecting Groups in Organic Synthesis", $2^{nd}$ ed. New York; John Wiley & Sons, Inc., 1991. Examples of alcohol protecting groups include benzyl, trityl, silyl ethers, and the like.

Amine groups in compounds described in any of the above methods may be protected with any convenient amine protecting group, for example as described in Greene & Wuts, eds., "Protecting Groups in Organic Synthesis", $2^{nd}$ ed. New York; John Wiley & Sons, Inc., 1991. Examples of amine protecting groups include acyl and alkoxycarbonyl groups, such as t-butoxycarbonyl (BOC), phenoxycarbonyl, and [2-(trimethylsilyl)ethoxy]methyl (SEM). Likewise, carboxyl groups may be protected with any convenient carboxyl protecting group, for example as described in Greene & Wuts, eds., "Protecting Groups in Organic Synthesis", $2^{nd}$ ed. New York; John Wiley & Sons, Inc., 1991. Examples of carboxyl protecting groups include (1-6C)alkyl groups, such as methyl, ethyl and t-butyl. Alcohol groups may be protected with any convenient alcohol protecting group, for example as described in Greene & Wuts, eds., "Protecting Groups in Organic Synthesis", $2^{nd}$ ed. New York; John Wiley & Sons, Inc., 1991. Examples of alcohol protecting groups include benzyl, trityl, silyl ethers, and the like.

The compounds of the formulas II, V, VI, VII, and VIII are also provided as further aspects of the invention. In one embodiment, compounds of the formulas II, V, VI, VII, and VIII are useful as intermediates for the preparation of compounds of Formula I.

Compounds of Formula I are useful in the treatment of pain, cancer, inflammation/inflammatory diseases, neurodegenerative diseases, certain infectious diseases, Sjogren's syndrome, endometriosis, diabetic peripheral neuropathy, prostatitis or pelvic pain syndrome.

In one embodiment, compounds of Formula I are useful for treating pain, including chronic and acute pain. For example, compounds of Formula I are useful in the treatment of multiple types of pain including inflammatory pain, neuropathic pain, and pain associated with cancer, surgery or bone fracture.

In one embodiment, compounds of Formula I are useful for treating acute pain. Acute pain, as defined by the International Association for the Study of Pain, results from disease, inflammation, or injury to tissues. This type of pain generally comes on suddenly, for example, after trauma or surgery, and may be accompanied by anxiety or stress, and is confined to a given period of time and severity. In some instances, it can become chronic.

In one embodiment, compounds of Formula I are useful for treating chronic pain. Chronic pain, as defined by the International Association for the Study of Pain, is widely believed to represent a disease in itself. It can be made much worse by environmental and psychological factors. Chronic pain persists over a longer period than acute pain and is resistant to most medical treatments, generally over 3 months or more. It can and often does cause severe problems for patients.

Compounds of Formula I are also useful for treating cancer. Particular examples include neuroblastoma, ovarian, pancreatic, colorectal and prostate cancer.

Compounds of Formula I are also useful for treating inflammation and certain infectious diseases. For example, compounds of Formula I may be used to treat interstitial cystitis (IC), painful bladder syndrome (PBS), urinary incontinence, asthma, atopic dermatitis, and psoriasis.

Compounds of Formula I are also useful for treating a neurodegenerative disease in a mammal, comprising administering to said mammal one or more compounds of Formula I or a pharmaceutically acceptable salt thereof in an amount effective to treat said neurodegenerative disease. In one embodiment, compounds of Formula I may also be used to treat demyelination and dysmyelination by promoting myelination, neuronal survival, and oligodendrocyte differentiation via blocking Sp35-TrkA interaction. In one embodiment, the neurodegenerative disease is multiple sclerosis. In one embodiment, the neurodegenerative disease is Parkinson's disease. In one embodiment, the neurodegenerative disease is Alzheimer's disease.

Compounds of Formula I are also useful for treating certain infectious diseases such as *Trypanosoma cruzi* infection in a mammal.

Compounds of Formula I are also useful for treating Sjogren's syndrome in a mammal.

Compounds of Formula I are also useful for treating endometriosis in a mammal.

Compounds of Formula I are also useful for treating diabetic peripheral neuropathy in a mammal.

Compounds of Formula I are also useful for treating prostatitis in a mammal.

Compounds of Formula I are also useful for treating pelvic pain syndrome in a mammal.

Compounds of Formula I are also useful in treating diseases related to an imbalance of the regulation of bone remodeling, such as osteoporosis, rheumatoid arthritis, and bone metastases.

As used herein, terms "treat" or "treatment" refer to therapeutic or palliative measures. Beneficial or desired clinical results include, but are not limited to, alleviation, in whole or in part, of symptoms associated with a disorder or condition, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment.

In certain embodiments, compounds of Formula I are useful for preventing diseases and disorders as defined herein. The term "preventing" as used herein means the prevention of the onset, recurrence or spread, in whole or in part, of the disease or condition as described herein, or a symptom thereof, and includes to the administration of a compound of Formula I prior to the onset of symptoms.

Accordingly, one embodiment of this invention provides a method of treating pain in a mammal, comprising administering to said mammal in need thereof one or more compounds of Formula I or a pharmaceutically acceptable salt thereof in an amount effective to treat said pain. In one embodiment, the pain is chronic pain. In one embodiment, the pain is acute pain. In one embodiment, the pain is inflammatory pain, neuropathic pain, or pain associated with cancer, surgery, or bone fracture.

Another embodiment of this invention provides a method of preventing pain in a mammal, comprising administering to said mammal in need thereof one or more compounds of Formula I or a pharmaceutically acceptable salt thereof in an amount effective to prevent said pain. In one embodiment, the pain is chronic pain. In one embodiment, the pain is acute pain. In one embodiment, the pain is inflammatory pain, neuropathic pain, or pain associated with cancer, surgery, or bone fracture.

Another embodiment of this invention provides a method of treating cancer in a mammal, comprising administering to said mammal in need thereof one or more compounds of Formula I or a pharmaceutically acceptable salt thereof in an amount effective to treat said cancer.

In one embodiment, provided herein is a method for treating a patient diagnosed with a cancer having a dysregulation of TrkA, comprising administering to the patient a therapeutically effective amount of a compound of the invention or a pharmaceutically acceptable salt thereof.

In one embodiment, the dysregulation of TrkA comprises overexpression of wild-type TrkA (autocrine activation).

In one embodiment, the dysregulation of TrkA comprises one or more chromosome translocations or inversions resulting in TrkA gene fusions. In one embodiment, the dysregulation is a result of genetic translocations in which the expressed protein is a fusion protein containing residues from non-TrkA and TrkA proteins, and at a minimum the TrkA kinase domain. In one embodiment, the TrkA fusion protein is LMNA-TrkA, TFG-TrkA, TPM3-TrkA, CD74-TrkA, NFASC-TrkA, MPRIP-TrkA, BCAN-TrkA, or TPR-TrkA, where:

LMNA=Prelamin-A/C;
TFG=TRK-fused gene protein;
TPM3=Tropomysin alpha-3;
CD74=HLA class II histocompatibility antigen gamma chain;
NFASC=Neurofascin;
MPRIP=MPRIP protein;
BCAN=Brevican core protein; and
TPR=Nucleoprotein TPR In one embodiment, the dysregulation of TrkA comprises one or more deletions, insertions or mutations in the TrkA protein. In one embodiment, the dysregulation comprises a deletion of one or more residues from the TrkA protein, resulting in constitutive activity of TrkA kinase. In one embodiment the deletion includes deletion of residues 303-377 in TrkA Isoform 2.

In one embodiment, the dysregulation of TrkA comprises a splice variation in which the expressed protein is an alternatively spliced variant of TrkA having one or more residues deleted resulting in constitutive activity of TrkA kinase. In one embodiment, an alternatively spliced form of TrkA with constitutive activity has deletions of exons 8, 9, and 11 resulting in an expressed protein missing residues 192-284 and 393-398 relative to TrkA Isoform 2.

Cancers identified as having dysregulation of TrkA (see literature references below; also see www.cancer.gov and www.nccn.org) include:

(A) Cancers wherein the dysregulation of TrkA comprises one or more chromosome translocations or inversions resulting in TrkA gene fusions, including:

| Cancer | Literature reference(s) | Standard of Care |
| --- | --- | --- |
| Non-Small Cell Lung Cancer | Vaishnavi et al. 2013: Nature Medicine 19, 1469-1472 | radiotherapy (e.g. radioiodide therapy, external-beam radiation, radium 223 therapy), chemotherapeutics as single agents (e.g. afatinib dimaleate, bevacizumab, carboplatin, cetuximab, cisplatin, crizotinib, erlotinib, gefitinib, gemcitabine, methotrexate, paclitaxel, pemetrexed) or combinations (e.g. carboplatin-paclitaxel, gemcitabine-paclitaxel, chemoradiation) |
| Papillary Thyroid Carcinoma | Caria et al. 2010: Cancer Genetics and Cytogenetics 203: 21-29 | Radiotherapies (e.g. radioiodide therapy, external-beam radiation) and chemotherapeutics (e.g. sorafenib, sunitinib, pazopanib) |
| Glioblastoma Multiforme | Frattini et al. 2013: Nature Genet. 45(10): 1141-9 | Chemotherapeutics (e.g. bevacizumab, everolimus, lomustine, temozolomide) |
| Colorectal Carcinoma | Martin-Zanca et al. 1986: Nature 319: 743 | Chemotherapeutics as single agents (aflibercept, bevacizumab, capecitabine, cetuximab, fluorouracil, irinotecan, leucovorin, oxaliplatin, panitumumab, regorafenib) or combinations (e.g. folfox, folfiri, capox, folfiri-bevacizumab, folfiri-cetuximab, xelox) |
| Melanoma | WO 2013/059740 A1 | Chemotherapeutics (e.g. aldesleukin, dabrafenib, dacarbazine, interferon alfa-2b, ipilimumab, peginterferon alfa-2b, trametinib, vemurafenib) |

(B) Cancers wherein the dysregulation of TrkA comprises one or more deletions, insertions or mutations in the TrkA protein, including:

| Cancer | Literature reference(s) | Standard of care |
|---|---|---|
| Acute Myeloid leukemia | Meyer 2007: Leukemia 21: 2171-2180<br>Reuther et al. 2000: Mol Cell Biol 20: 8655-8666 | Chemotherapeutics as single agents (e.g. arsenic trioxide, cyclophosphamide, cytarabine, daunorubicin, doxorubicin, vincristine) or combinations (e.g. ADE) |
| Large Cell Neuroendocrine Carcinoma | Marchetti et al 2008: Human Mutation 29(5): 609-616 | Radiotherapy (e.g. radioiodide therapy, external-beam radiation, radium 223 therapy) and/or chemotherapeutics (e.g. cisplatin, carboplatin, etoposide) |
| Neuroblastoma | Tacconelli et al 2004: Cancer Cell 6: 347 | Chemotherapeutics (e.g. cyclophosphamide, doxorubicin, vincristine) |

(C) Cancers driven by overexpression of wild-type TrkA (autocrine activation), including:

| Cancer | Literature Reference(s) | Standard of care |
|---|---|---|
| Prostate Carcinoma | Walch et al: Clinical & Experimental Metastasis 17: 307-314<br>Papatsoris et al 2007: Expert Opinion on Investigational Drugs 16(3): 303-309 | Radiotherapy (e.g. radium 223 therapy) or chemotherapeutics (e.g. abiraterone, cabazitaxel, degarelix, denosumab, docetaxel, enzalutamide, leuprolide, prednisone, sipuleucel-T) |
| Neuroblastoma | Van Noesel et al 2004: Gene 325: 1-15 | Chemotherapeutics (e.g. cyclophosphamide, doxorubicin, vincristine) |
| Pancreatic Carcinoma | Zhang et al 2005: Oncology Reports 14: 161-171 | Chemotherapeutics as single agents (e.g. erlotinib, fluorouracil, gemcitabine, mitomycin C) or combinations (e.g. gemcitabine-oxaliplatin) |
| Melanoma | Truzzi et al 2008: Journal of Investigative Dermatology 128(8): 2031 | Chemotherapeutics (e.g. aldesleukin, dabrafenib, dacarbazine, interferon alfa-2b, ipilimumab, peginterferon alfa-2b, trametinib, vemurafenib) |
| Head and Neck Squamous Cell Carcinoma | Kolokythas et al 2010: Journal of Oral and Maxillofacial Surgery 68(6): 1290-1295 | Radiotherapy and/or chemotherapeutics (e.g. bleomycin, cetuximab, cisplatin, docetaxel, fluorouracil, methotrexate) |
| Gastric Carcinoma | Ni et al 2012: Asian Pacific Journal of Cancer Prevention 13: 1511 | Chemotherapeutics (e.g. docetaxel, doxorubicin, fluorouracil, mitomycin C, trastuzumab) |

In one embodiment, provided herein is a method for treating a patient diagnosed with a cancer having a dysregulation of TrkA, comprising administering to the patient a therapeutically effective amount of a compound of the invention, or a pharmaceutically acceptable salt thereof, wherein the cancer is selected from non-small cell lung cancer, papillary thyroid carcinoma, glioblastoma multiforme, acute myeloid leukemia, colorectal carcinoma, large cell neuroendocrine carcinoma, prostate cancer, neuroblastoma, pancreatic carcinoma, melanoma, head and neck squamous cell carcinoma and gastric carcinoma.

In one embodiment, the compounds of the present invention are useful for treating cancer in combination with one or more additional therapeutic agents or therapies that work by the same or a different mechanism of action.

In one embodiment, the additional therapeutic agent(s) is selected from receptor tyrosine kinase-targeted therapeutic agents, including cabozantinib, crizotinib, erlotinib, gefitinib, imatinib, lapatinib, nilotinib, pazopanib, pertuzumab, regorafenib, sunitinib, and trastuzumab.

In one embodiment, the additional therapeutic agent(s) is selected from signal transduction pathway inhibitors, including Ras-Raf-MEK-ERK pathway inhibitors (e.g. sorafenib, trametinib, vemurafenib), PI3K-Akt-mTOR-S6K pathway inhibitors (e.g. everolimus, rapamycin, perifosine, temsirolimus) and modulators of the apoptosis pathway (e.g. obataclax).

In one embodiment, the additional therapeutic agent(s) is selected from cytotoxic chemotherapeutics, including arsenic trioxide, bleomycin, cabazitaxel, capecitabine, carboplatin, cisplatin, cyclophosphamide, cytarabine, dacarbazine, daunorubicin, docetaxel, doxorubicin, etoposide, fluorouracil, gemcitabine, irinotecan, lomustine, methotrexate, mitomycin C, oxaliplatin, paclitaxel, pemetrexed, temozolomide, and vincristine.

In one embodiment, the additional therapeutic agent(s) is selected from angiogenesis-targeted therapies, including aflibercept and bevacizumab.

In one embodiment, the additional therapeutic agent(s) is selected from immune-targeted agents, including aldesleukin, ipilimumab, lambrolizumab, nivolumab, sipuleucel-T.

In one embodiment, the additional therapeutic agent(s) is selected from agents active against the TrkA pathway, including NGF-targeted biopharmaceuticals such as NGF antibodies, and panTrk inhibitors.

In one embodiment, the additional therapeutic agent or therapy is radiotherapy, including radioiodide therapy, external-beam radiation and radium 223 therapy.

In one embodiment, the additional therapeutic agent(s) includes any one of the above listed therapies or therapeutic agents which are standards of care in cancers wherein the cancer has a dysregulation of TrkA.

In one embodiment, provided herein is a method of treating cancer in a patient, comprising administering to said patient a compound of the invention or a pharmaceutically acceptable salt thereof, in combination with at least one additional therapy or therapeutic agent selected from radiotherapy (e.g. radioiodide therapy, external-beam radiation, radium 223 therapy), cytotoxic chemotherapeutics (e.g. arsenic trioxide, bleomycin, cabazitaxel, capecitabine, carboplatin, cisplatin, cyclophosphamide, cytarabine, dacarbazine, daunorubicin, docetaxel, doxorubicin, etoposide, fluorouracil, gemcitabine, irinotecan, lomustine, methotrexate, mitomycin C, oxaliplatin, paclitaxel, pemetrexed, temozolomide, vincristine), tyrosine kinase targeted-therapeutics (e.g. afatinib, cabozantinib, cetuximab, crizotinib, dabrafenib, erlotinib, gefitinib, imatinib, lapatinib, nilotinib, pazopanib, panitumumab, pertuzumab, regorafenib, sunitinib, trastuzumab), apoptosis modulators and signal transduction inhibitors (e.g. everolimus, perifosine, rapamycin, sorafenib, temsirolimus, trametinib, vemurafenib), immune-targeted therapies (e.g. aldesleukin, interferon alfa-2b, ipilimumab, lambrolizumab, nivolumab, prednisone, sipuleucel-T) and angiogenesis-targeted therapies (e.g. aflibercept, bevacizumab), wherein the amount of the compound of the invention or a pharmaceutically acceptable salt thereof is, in combination with the additional therapy or therapeutic agent, is effective in treating said cancer. These additional therapeutic agents may be administered with one or more compounds of the invention as part of the same or separate dosage forms, via the same or different routes of administration, and on the same or different administration schedules according to standard pharmaceutical practice known to one skilled in the art.

Also provided herein is (i) a pharmaceutical combination for treating cancer in a patient in need thereof, which comprises (a) a compound of the invention or a pharmaceutically acceptable salt thereof, (b) an additional therapeutic agent and (c) optionally at least one pharmaceutically acceptable carrier for simultaneous, separate or sequential use for the treatment of a tumor disease, wherein the amounts of the compound or salt thereof and of the additional therapeutic agent are together effective in treating said cancer; (ii) a pharmaceutical composition comprising such a combination; (iii) the use of such a combination for the preparation of a medicament for the treatment of cancer; and (iv) a commercial package or product comprising such a combination as a combined preparation for simultaneous, separate or sequential use; and to a method of treatment of cancer a patient in need thereof.

In one embodiment, the combination therapy is for treating a cancer is selected from non-small cell lung cancer, papillary thyroid carcinoma, glioblastoma multiforme, acute myeloid leukemia, colorectal carcinoma, large cell neuroendocrine carcinoma, prostate cancer, neuroblastoma, pancreatic carcinoma, melanoma, head and neck squamous cell carcinoma and gastric carcinoma.

Another embodiment of this invention provides a method of treating inflammation or an inflammatory disease or disorder in a mammal, comprising administering to said mammal in need thereof one or more compounds of Formula I or a pharmaceutically acceptable salt thereof in an amount effective to treat said inflammation. In one embodiment, the inflammatory disease is inflammatory lung diseases (such as asthma), interstitial cystitis, bladder pain syndrome, inflammatory bowel diseases (including ulcerative colitis and Crohn's disease), and inflammatory skin diseases such as atopic dermatitis.

In one embodiment, the method of treating inflammation or an inflammatory disease or disorder comprises administering a compound of the invention in combination with one or more additional agents. Examples of additional agents include anti-TNF treatments (for example monoclonal antibody such as infliximab (Remicade), adalimumab (Humira), certolizumab pegol (Cimzia), and golimumab (Simponi), or a circulating receptor fusion protein such as etanercept (Enbrel)), antimetabolite and antifolate drug (for example Methotrexate), or targeted kinase inhibitors (for example JAK family inhibitors Ruxolitinib, Tofacitinib, CYT387, Lestaurtinib, Pacritinib and TG101348).

Another embodiment of this invention provides a method of treating *Trypanosoma cruzi* infection in a mammal, comprising administering to said mammal in need thereof one or more compounds of Formula I or a pharmaceutically acceptable salt thereof in an amount effective to treat said *Trypanosoma cruzi* infection.

Another embodiment of this invention provides a method of treating Sjogren's syndrome in a mammal, comprising administering to said mammal in need thereof one or more compounds of Formula I or a pharmaceutically acceptable salt thereof in an amount effective to treat said syndrome.

Another embodiment of this invention provides a method of treating endometriosis in a mammal, comprising administering to said mammal in need thereof one or more compounds of Formula I or a pharmaceutically acceptable salt thereof in an amount effective to treat said endometriosis.

Another embodiment of this invention provides a method of treating diabetic peripheral neuropathy in a mammal, comprising administering to said mammal in need thereof one or more compounds of Formula I or a pharmaceutically acceptable salt thereof in an amount effective to treat said diabetic peripheral neuropathy.

Another embodiment of this invention provides a method of treating prostatitis in a mammal, comprising administering to said mammal in need thereof one or more compounds of Formula I or a pharmaceutically acceptable salt thereof in an amount effective to treat said prostatitis.

Another embodiment of this invention provides a method of treating pelvic pain syndrome in a mammal, comprising administering to said mammal in need thereof one or more compounds of Formula I or a pharmaceutically acceptable salt thereof in an amount effective to treat said pelvic pain syndrome.

Another embodiment of this invention provides a method of treating a neurodegenerative disease in a mammal, comprising administering to said mammal in need thereof one or more compounds of Formula I or a pharmaceutically acceptable salt thereof in an amount effective to treat said neurodegenerative disease.

As used herein, an "effective amount" means an amount of compound that, when administered to a mammal in need of such treatment, is sufficient to (i) treat a particular disease, condition, or disorder which can be treated with a compound of Formula I, or (ii) attenuate, ameliorate, or eliminate one or more symptoms of the particular disease, condition, or disorder described herein.

The amount of a compound of Formula I that will correspond to such an amount will vary depending upon factors such as the particular compound, disease condition and its severity, the identity (e.g., weight) of the mammal in need of treatment, but can nevertheless be routinely determined by one skilled in the art.

As used herein, the term "mammal" refers to a warm-blooded animal that has or is at risk of developing a disease described herein and includes, but is not limited to, guinea pigs, dogs, cats, rats, mice, hamsters, and primates, including humans.

The compounds of the present invention can be used in combination with one or more additional therapeutic agents that work by the same or a different mechanism of action. Examples of additional therapeutic agents include anti-inflammatory compounds, steroids (e.g., dexamethasone, cortisone and fluticasone), analgesics such as NSAIDs (e.g., aspirin, ibuprofen, indomethacin, and ketoprofen), and opioids (such as morphine), and chemotherapeutic agents.

Also provided herein is a pharmaceutical combination comprising an effective amount of: (a) at least one compound of Formula I; and (b) at least one additional therapeutic agent selected from anti-inflammatory compounds, steroids (e.g., dexamethasone, cortisone and fluticasone), analgesics such as NSAIDs (e.g., aspirin, ibuprofen, indomethacin, and ketoprofen), and opioids (such as morphine), for use in the treatment of pain in a mammal, wherein (a) and (b) can be in separate dosage forms or in the same dosage form.

The term "pharmaceutical combination" as used herein refers to a pharmaceutical therapy resulting from the mixing or combining of more than one active ingredient and includes both fixed and non-fixed combinations of the active ingredients. The term "fixed combination" means that at least one of the compounds of Formula I, and at least one additional therapeutic agent are both administered to a patient simultaneously in the form of a single entity or dosage. The term "non-fixed combination" means that at least one of the compounds of Formula I, and at least one additional therapeutic agent, are administered to a patient as separate entities either simultaneously or sequentially with variable intervening time limits, wherein such administration provides effective levels of the two or more compounds in the body of the patient. These also apply to cocktail therapies, e.g. the administration of three or more active ingredients.

Also provided herein is a method of treating pain in a mammal, comprising co-administering to a mammal in need thereof an effective amount of: (a) at least one compound of Formula I; and (b) at least one additional therapeutic agent selected from anti-inflammatory compounds, steroids (e.g., dexamethasone, cortisone and fluticasone), analgesics such as NSAIDs (e.g., aspirin, ibuprofen, indomethacin, and ketoprofen), opioids (such as morphine), calcitonin gene-related peptide receptor antagonists, subtype-selective ion channel modulators, anticonvulsants (for example Pregabalin and gabapentin), dual serotonin-norepinephrin reuptake inhibitors (for example duloxetine, venlafaxine and milnacipran), and tricyclic antidepressants (such as amitriptyline, nortriptyline and desipramine).

Another embodiment of this invention provides a method of treating diseases related to an imbalance of the regulation of bone remodeling in a mammal, comprising administering to said mammal in need thereof one or more compounds of Formula I or a pharmaceutically acceptable salt thereof in an amount effective to treat said disease. In one embodiment, the disease is osteoporosis, rheumatoid arthritis, and bone metastases.

In one embodiment, the method for treating diseases related to an imbalance of the regulation of bone remodeling in a mammal comprises administering a TrkA inhibitor of the invention in combination with one or more additional therapeutic agents or therapies. Examples of additional therapeutic agents or therapies include anti-TNF treatments (for example monoclonal antibody such as infliximab (Remicade), adalimumab (Humira), certolizumab pegol (Cimzia), and golimumab (Simponi), or with a circulating receptor fusion protein such as etanercept (Enbrel)), antimetabolite and antifolate drug (for example Methotrexate), or targeted kinase inhibitors (for example JAK family inhibitors Ruxolitinib, Tofacitinib, CYT387, Lestaurtinib, Pacritinib and TG101348).

The term "co-administering" is meant to encompass administration of the selected therapeutic agents to a single patient, and is intended to include treatment regimens in which the agents are administered by the same or different route of administration or at the same or different times. This term encompasses administration of two or more agents to a mammal so that both agents and/or their metabolites are present in the mammal at the same time. It includes simultaneous administration in separate compositions, administration at different times in separate compositions, and/or administration in a composition in which both agents are present. In some embodiments, the compound(s) of the invention and the other therapeutic agent(s) are administered in a single composition. In some embodiments, compound(s) of the invention and the other agent(s) are admixed in the composition.

Also provided herein is a medicament containing a compound of Formula I for treatment of pain in a mammal in combination with an additional therapeutic agent selected from anti-inflammatory compounds, steroids (e.g., dexamethasone, cortisone and fluticasone), analgesics such as NSAIDs (e.g., aspirin, ibuprofen, indomethacin, and ketoprofen), and opioids (such as morphine).

Also provided herein is a medicament containing a therapeutic agent selected from anti-inflammatory compounds, steroids (e.g., dexamethasone, cortisone and fluticasone), analgesics such as NSAIDs (e.g., aspirin, ibuprofen, indomethacin, and ketoprofen), and opioids (such as morphine) for treatment of pain in a mammal in combination with a compound of Formula I.

Compounds of the invention may be administered by any convenient route, e.g. into the gastrointestinal tract (e.g. rectally or orally), the nose, lungs, musculature or vasculature, or transdermally or dermally. Compounds may be administered in any convenient administrative form, e.g. tablets, powders, capsules, solutions, dispersions, suspensions, syrups, sprays, suppositories, gels, emulsions, patches etc. Such compositions may contain components conventional in pharmaceutical preparations, e.g. diluents, carriers, pH modifiers, sweeteners, bulking agents, and further active agents. If parenteral administration is desired, the compositions will be sterile and in a solution or suspension form suitable for injection or infusion. Such compositions form a further aspect of the invention.

Another formulation may be prepared by mixing a compound described herein and a carrier or excipient. Suitable carriers and excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound described herein or pharmaceutical composition thereof) or aid in the manufacturing of the pharmaceutical product (i.e., medicament).

Accordingly, another aspect of the present invention provides a pharmaceutical composition, which comprises a compound of Formula I or a pharmaceutically acceptable salt thereof, as defined hereinabove, together with a pharmaceutically acceptable diluent or carrier.

According to another embodiment, the present invention provides a compound of Formula I or a pharmaceutically acceptable salt thereof, for use in the treatment of pain in a mammal. In one embodiment, the pain is chronic pain. In one embodiment the pain is acute pain. In one embodiment, the pain is inflammatory pain, neuropathic pain, or pain associated with cancer, surgery, or bone fracture.

According to another embodiment, the present invention provides a compound of Formula I or a pharmaceutically acceptable salt thereof, for use in the treatment of cancer in a mammal.

In another embodiment, the present invention provides a compound of Formula I or a pharmaceutically acceptable salt thereof, for use in the treatment of inflammation or an inflammatory disease or disorder in a mammal. In one embodiment, the inflammatory disease is inflammatory lung diseases (such as asthma), interstitial cystitis, bladder pain syndrome, inflammatory bowel diseases (including ulcerative colitis and Crohn's disease), and inflammatory skin diseases such as atopic dermatitis.

In another embodiment, the present invention provides a compound of Formula I or a pharmaceutically acceptable salt thereof, for use in the treatment of infectious diseases, for example *Trypanosoma cruzi* infection, in a mammal.

In another embodiment, the present invention provides a compound of Formula I or a pharmaceutically acceptable salt thereof, for use in the treatment of Sjogren's syndrome in a mammal.

In another embodiment, the present invention provides a compound of Formula I or a pharmaceutically acceptable salt thereof, for use in the treatment of endometriosis in a mammal.

In another embodiment, the present invention provides a compound of Formula I or a pharmaceutically acceptable salt thereof, for use in the treatment of diabetic peripheral neuropathy in a mammal, In another embodiment, the present invention provides a compound of Formula I or a pharmaceutically acceptable salt thereof, for use in the treatment of prostatitis in a mammal, In another embodiment, the present invention provides a compound of Formula I or a pharmaceutically acceptable salt thereof, for use in the treatment of pelvic pain syndrome in a mammal, In another embodiment, the present invention provides a compound of Formula I or a pharmaceutically acceptable salt thereof, for use in the treatment of a neurodegenerative disease in a mammal.

According to a further aspect, the present invention provides the use of a compound of Formula I or a pharmaceutically acceptable salt thereof, in the manufacture of a medicament for the treatment of a condition selected from pain, cancer, inflammation, neurodegenerative disease or *Trypanosoma cruzi* infection. In one embodiment, the condition is chronic pain. In one embodiment, the condition is acute pain. In one embodiment, the pain is inflammatory pain, neuropathic pain, or pain associated with cancer, surgery, or bone fracture. In one embodiment, the condition is cancer. In one embodiment, the condition is inflammation. In one embodiment, the condition is a neurodegenerative disease. In one embodiment, the condition is *Trypanosoma cruzi* infection. In one embodiment, the condition is Sjogren's syndrome. In one embodiment, the condition is endometriosis. In one embodiment, the condition is diabetic peripheral neuropathy. In one embodiment, the condition is prostatitis. In one embodiment, the condition is pelvic pain syndrome.

EXAMPLES

The following examples illustrate the invention. In the examples described below, unless otherwise indicated all temperatures are set forth in degrees Celsius. Reagents were purchased from commercial suppliers such as Aldrich Chemical Company, Lancaster, TCI or Maybridge, and were used without further purification unless otherwise indicated.

The reactions set forth below were done generally under a positive pressure of nitrogen or argon (unless otherwise stated) in anhydrous solvents, and the reaction flasks were typically fitted with rubber septa for the introduction of substrates and reagents via syringe. Glassware was oven dried and/or heat dried.

Column chromatography was done on a Biotage system (Manufacturer: Dyax Corporation) having a silica gel or C-18 reverse phase column, or on a silica SepPak cartridge (Waters).

Biological Assays

Example A-1

TrkA Kinase Binding Assay

TrkA binding activity was determined in a TrkA LanthaScreen™ Eu Kinase Binding Assay. 5 nM His-tagged recombinant human TrkA (6HIS tagged cytoplasmic domain from Invitrogen, Cat. No. PV3144) was incubated with 4 nM Alexa-Fluor® Tracer 236 (Invitrogen Cat. No. PV5592), 2 nM biotinylated anti-His (Invitrogen Cat. No. PV6090), and 2 nM europium-labeled Streptavidin (Invitrogen Cat. No. PV5899), in buffer (25 mM MOPS, pH 7.5, 5 mM $MgCl_2$, 0.005% Triton X-100). Three fold serial dilutions of compounds of the invention in DMSO were added to a final percentage of 2% DMSO. After 60-minute incubation at 22° C., the reaction was measured using the EnVision mutlimode plate reader (PerkinElmer) via TR-FRET dual wavelength detection at 615 nM and 665 nM. The percent of control was calculated using a ratiometric emission factor. The $IC_{50}$ values were determined by fitting a four parameter model to the percent of control data.

Table A provides averaged IC$_{50}$ values for compounds of the invention when tested in the assay of Example A, where A represents an averaged IC$_{50}$ value <100 nM; and B represents an averaged IC$_{50}$ value from 100 to 1,000 nM.

TABLE A

| Example # | TrkA enzyme IC$_{50}$ (nM) |
|---|---|
| 1 (Representative example) | A |
| 2 (Representative example) | B |
| 3 (Representative example) | A |
| 4 | A |
| 5 | A |
| 6 | B |
| 7 (Representative example) | A |
| 8 (Representative example) | B |
| 9 (Representative example) | B |
| 10 (Representative example) | B |
| 11 | A |
| 12 | A |

Example A-2 p38 Kinase Binding Assay p38α binding activity was determined in a p38α LanthaScreen™ Eu Kinase Binding Assay. 5 nM of inactive, GST-tagged recombinant human p38α (GST-tagged cytoplasmic domain from Invitrogen, Catalog No. PV3305) was incubated with 5 nM Alexa-Fluor® Tracer 199 (Invitrogen Cat. No. PV5830), and 2 nM europium labeled anti-GST antibody (Invitrogen Cat. No. PV5594), in buffer (25 mM [Na$^+$] HEPES pH 7.3, 10 mM MgCl$_2$, 100 µM NaVO$_4$). Three fold serial dilutions of compounds of the invention in DMSO were added to a final percentage of 2% DMSO. After 60-minute incubation at 22° C., the reaction was measured using the EnVision multimode plate reader (PerkinElmer) via TR-FRET dual wavelength detection at 615 nM and 665 nM. The percent of control was calculated using a ratiometric emission factor. The IC$_{50}$ values were determined by fitting a four parameter model to the percent of control data. The compounds of Examples 1-12 were tested in this assay, and all compounds were found to be 1000 fold more potent against TrkA than p38α.

Example B

Off-Target Kinase Profiling

A representative compound of the invention (Example 3) was tested for off-target kinase activity at a concentration of 10 µM by Millipore, Inc. in their KinaseProfiler™ service against all the kinases available in their full kinase panel. The compound was run in duplicate at a concentration of ATP near the Km for each individual kinase according to Millipore's specifications. The results are shown in Table B. Data are reported as percent of control (POC) and are the average of the two replicates.

In the KinaseProfiler™ the compound of Example 3 showed remarkable and unexpected selectivity for inhibiting TrkA versus other kinases in the panel. In fact, the compound was largely inactive against off-target kinases at a concentration of 10 µM, and thus would not be expected to inhibit off-target kinases at therapeutic doses in mammals. The ability of compounds of the invention to selectively inhibit the Trk pathway without inhibiting other off-target kinases could translate into drug profiles that are essentially free of side-effects related to inhibition of off-target kinases. Such a drug profile would represent a safer approach to treating pain, inflammation, cancer and certain skin diseases than has been previously reported.

TABLE B

| Kinase | Example 3 Avg POC |
|---|---|
| Abl2 | 148.5 |
| Abl-P | 154.5 |
| AKT1 | 103.5 |
| AKT2 | 219.5 |
| AKT3 | 99 |
| ALK | 110 |
| ALK4 | 104.5 |
| AMPK(A1/B1/G1) | 149.5 |
| ARK5 | 92.5 |
| AURKA | 121 |
| Axl | 117 |
| BLK_m | 108.5 |
| Bmx | 114.5 |
| BrSK1 | 127 |
| BrSK2 | 135 |
| BTK | 123 |
| CAMK1 | 103.5 |
| CAMK1d | 138 |
| CAMK2b | 96.5 |
| CAMK2d | 131 |
| CAMK2g | 112 |
| CAMK4 | 147.5 |
| CDK1/cyclinB | 102.5 |
| CDK2/cyclinA | 100.5 |
| CDK2/cyclinE | 106.5 |
| CDK3/cyclinE | 103 |
| CDK5/p25 | 108.5 |
| CDK5/p35 | 110.5 |
| CDK6/cyclinD3 | 107.5 |
| CDK7/cyclinH/MAT1 | 120.5 |
| CDK9/cyclinT1 | 107.5 |
| CHK1 | 108 |
| CHK2 | 126.5 |
| CK1_y | 98 |
| CK1delta | 141 |
| CK1gamma1 | 112 |
| CK1gamma2 | 109 |
| CK1gamma3 | 125 |
| CK2 | 96.5 |
| CK2alpha2 | 102.5 |
| CLK2 | 135 |
| CLK3 | 104 |
| c-RAF | 94.5 |
| CSK | 137.5 |
| DAPK1 | 137.5 |
| DAPK2 | 106 |
| DAPK3 | 118.5 |
| DCAMKL2 | 222.5 |
| DDR2 | 98 |
| DMPK | 105 |
| DRAK1 | 129 |
| DYRK2 | 92.5 |
| eEF-2K | 148.5 |
| EGFR | 97.5 |
| EphA1 | 93.5 |
| EphA2 | 120 |
| EphA3 | 128.5 |
| EphA4 | 106.5 |
| EphA5 | 116 |
| EphA7 | 91 |
| EphA8 | 122 |
| EphB1 | 122 |
| EphB2 | 118.5 |

TABLE B-continued

| Kinase | Example 3 Avg POC |
|---|---|
| EphB3 | 63 |
| EphB4 | 116 |
| ErbB4 | 126 |
| ERK1 | 111.5 |
| ERK2 | 116 |
| FAK | 105.5 |
| FAK2 | 103.5 |
| Fer | 92.5 |
| Fes | 123 |
| FGFR1 | 96 |
| FGFR2 | 110 |
| FGFR3 | 116.5 |
| FGFR4 | 174.5 |
| Fgr | 118 |
| Flt1 | 91.5 |
| Flt3 | 71 |
| Flt4 | 80.5 |
| Fms | 91.5 |
| Fyn | 110 |
| GRK5 | 84 |
| GRK6 | 105 |
| GRK7 | 104.5 |
| GSK3alpha | 170 |
| GSK3beta | 195 |
| Haspin | 121 |
| Hck | 110.5 |
| HIPK1 | 115.5 |
| HIPK2 | 101.5 |
| HIPK3 | 109.5 |
| IGF-1R | 74.5 |
| IGF-1R Activated | 87 |
| IKKalpha | 127 |
| IKKbeta | 123 |
| IR | 90 |
| IR Activated | 99.5 |
| IRAK1 | 102.5 |
| IRAK4 | 131.5 |
| IRR | 99.5 |
| ITK | 128 |
| JAK2 | 136.5 |
| JAK3 | 117.5 |
| JNK1alpha1 | 111.5 |
| JNK2alpha2 | 99.5 |
| JNK3 | 124.5 |
| KDR | 115.5 |
| KIT | 86.5 |
| Lck | 93 |
| LIMK1 | 92 |
| LKB1 | 95.5 |
| LOK | 97.5 |
| Lyn | 98 |
| MAP3K5 | 102 |
| MAP4K2 | 113 |
| MAPKAP-K2 | 142.5 |
| MAPKAP-K3 | 128.5 |
| MAPKAP-K5 | 108.5 |
| MARK1 | 112 |
| MARK2 | 106.5 |
| MEK1 | 111 |
| MELK | 115 |
| Mer | 104.5 |
| Met | 129 |
| MINK | 105 |
| MKK4_m | 132.5 |
| MKK6 | 132.5 |
| MKK7beta | 143.5 |
| MKNK2 | 99 |
| MLK1 | 100.5 |
| MRCKalpha | 172.5 |
| MRCKbeta | 121.5 |
| MSK1 | 152.5 |
| MSK2 | 119.5 |
| MSSK1 | 140 |
| MST1 | 92.5 |
| MST2 | 102.5 |
| MST3 | 146.5 |
| mTOR | 78.5 |
| mTOR/FKBP12 | 92.5 |
| MuSK | 82.5 |
| MYLK | 122 |
| NEK11 | 110 |
| NEK2 | 125.5 |
| NEK3 | 105.5 |
| NEK6 | 125 |
| NEK7 | 118 |
| NLK | 116.5 |
| p38alpha | 93 |
| p38beta | 102 |
| p38delta | 92.5 |
| p38gamma | 114.5 |
| p70S6K | 273.5 |
| PAK2 | 98 |
| PAK4 | 103 |
| PAK5 | 145.5 |
| PAK6 | 167 |
| PASK | 147 |
| PDGFRalpha | 106 |
| PDGFRbeta | 175 |
| PDK1 | 123 |
| PhKgamma2 | 115.5 |
| Pim-1 | 119.5 |
| Pim-2 | 117.5 |
| Pim-3 | 107.5 |
| PKAC-alpha | 136.5 |
| PKCalpha | 104 |
| PKCbetaI | 87 |
| PKCbetaII | 96.5 |
| PKCdelta | 98.5 |
| PKCepsilon | 98 |
| PKCeta | 94.5 |
| PKCgamma | 100 |
| PKCiota | 69.5 |
| PKCtheta | 113.5 |
| PKCzeta | 103 |
| PKD1 | 100.5 |
| PKD2 | 115 |
| Plk1 | 95 |
| Plk2 | 106 |
| Plk3 | 115 |
| PRK2 | 106.5 |
| PRKG1alpha | 108 |
| PRKG1beta | 98 |
| PrKX | 188 |
| PTK5 | 102 |
| PTK6 | 110 |
| Ret | 89.5 |
| RIPK2 | 96.5 |
| ROCK-I | 115 |
| ROCK-II | 110 |
| Ron | 90.5 |
| Ros | 97 |
| Rse | 106.5 |
| Rsk1 | 123 |
| Rsk2 | 134 |
| Rsk3 | 104.5 |
| Rsk4 | 99 |
| SGK1 | 276.5 |
| SGK2 | 159.5 |
| SGK3 | 133 |
| SIK | 154.5 |
| SRC | 102.5 |
| SRPK1 | 111 |
| SRPK2 | 112.5 |
| STK33 | 107.5 |
| Syk | 101 |
| TAK1 | 94 |
| TAO1 | 119 |
| TAO2 | 108 |
| TAO3 | 94 |
| TBK1 | 103 |
| TEC Activated | 144.5 |
| Tie2 | 121.5 |
| TLK2 | 108.5 |
| TNK2 | 118.5 |

TABLE B-continued

| Kinase | Example 3 Avg POC |
|---|---|
| TrkA | 0.5 |
| TrkB | 95 |
| TSSK1 | 83.5 |
| TSSK2 | 132.5 |
| Txk | 139.5 |
| ULK2 | 98 |
| ULK3 | 90.5 |
| VRK2 | 96.5 |
| WNK2 | 120 |
| WNK3 | 108 |
| Yes | 114 |
| ZAP-70 | 135 |

Preparation of Synthetic Intermediates

Intermediate 1

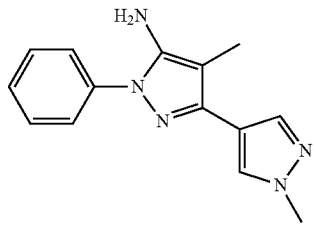 [SMILES: Cc1c(-c2cnn(C)c2)nn(-c2ccccc2)c1N]

1',4-dimethyl-1-phenyl-1H,1'H-3,4'-bipyrazol-5-amine

Step A: ethyl 1-methyl-1H-pyrazole-4-carboxylate

To a 3000-mL three-necked flask was added ethyl 2-formyl-3-oxopropanoate (100 g, 694 mmol), followed by anhydrous 200-proof EtOH (694 mL). The reaction was cooled in an ice bath to 5° C., and then methylhydrazine (35.8 mL, 680 mmol) was added dropwise. A vigorous exotherm was observed during hydrazine addition and the temperature was kept below 12° C. by controlling the addition rate. After the hydrazine addition was complete, the ice bath was removed, and the reaction was allowed to stir at ambient temperature for 16 hours. The reaction was concentrated in vacuo and the residue dissolved in DCM and re-concentrated, then dried for 2 days to yield ethyl 1-methyl-1H-pyrazole-4-carboxylate (106 g, 99% yield) as a tan orange oil. MS (apci) m/z=155.1 (M+H).

Step B: 2-methyl-3-(1-methyl-1H-pyrazol-4-yl)-3-oxopropanenitrile

To a four-necked 5-liter round bottomed flask fitted with an overhead stirrer and addition funnel was charged LHMDS (1444 mL, 1444 mmol) (1.0M in THF). The solution was cooled in an acetone/dry ice bath first (internal temperature of −79° C.) under nitrogen, followed by slow addition of propiononitrile (103 mL, 1444 mmol) via dropping funnel. The mixture was stirred at −80° C. for 90 minutes. A solution of ethyl 1-methyl-1H-pyrazole-4-carboxylate (106 g, 688 mmol) in anhydrous THF (500 mL) was then introduced dropwise via an addition funnel (addition time: about 45 minutes; internal temperature during addition remained below −76° C.). After the addition was complete, the reaction was allowed to slowly warm to ambient temperature and stirred overnight. An orange glass deposited on the bottom of the flask. The organics were decanted and the glass was dissolved in warm water. The mixture was washed with ether (3×1000 mL) The aqueous phase was then pH-adjusted to 5 (pH paper) using concentrated HCl and saturated bicarbonate solution The aqueous layer was extracted with DCM (3×1000 mL). The combined organic extracts were dried over MgSO4 filtered and concentrated to yield 2-methyl-3-(1-methyl-1H-pyrazol-4-yl)-3-oxopropanenitrile as an amber oil (92 g, 82% yield). MS (apci) m/z=162.1 (M−H).

Step C: 1',4-dimethyl-1-phenyl-1H,1'H-3,4'-bipyrazol-5-amine

A 3 L, 3 necked round bottomed flask was charged with 2-methyl-3-(1-methyl-1H-pyrazol-4-yl)-3-oxopropanenitrile (60 g, 368 mmol) absolute anhydrous ethanol (1000 mL) and phenylhydrazine hydrochloride (58 g, 404 mmol) at ambient temperature to form a yellowish suspension. The reaction vessel was equipped with a water condenser and refluxed (using a heating mantle) overnight. The reaction was concentrated and 1M NaOH (1 L) was added and the solid was broken up and collected. The solid was washed with water and hexanes. A second crop crashed out in the filtrate and was collected. The combined solids were crushed and triturated with ether (500 mL). The solid was collected by filtration, washed with hexanes and dried in vacuo to provide the title compound (93 g, 100% yield) as a yellow solid. MS (apci) m/z=254.1 (M+H).

Intermediate 2

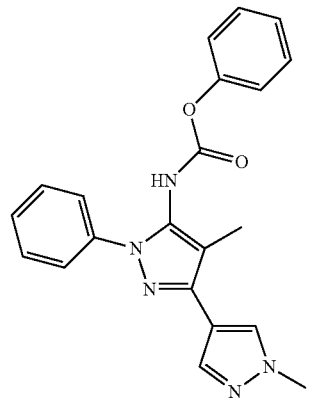 [SMILES: Cc1c(-c2cnn(C)c2)nn(-c2ccccc2)c1NC(=O)Oc1ccccc1]

phenyl (1',4-dimethyl-1-phenyl-1H,1'H-[3,4'-bipyrazol]-5-yl)carbamate

A 3 L, round bottomed flask was charged with 1',4-dimethyl-1-phenyl-1H,1'H-3,4'-bipyrazol-5-amine [Intermediate 1] (50 g, 197.4 mmol) and EtOAc (1000 mL) to obtain a clear brownish solution. To this was added NaOH (2M aq) (500 mL) in one portion to obtain a turbid mixture (the aqueous and organic layers were clear, but a precipitate was observed in between the two layers). After 3 minutes, phenyl carbonochloridate (74.29 mL, 592.2 mmol) was added slowly at ambient temperature (the temperature of the reaction mixture increased to 33° C. during the addition). The reaction stirred at ambient temperature for 2 hours. Additional phenyl carbonochloridate (10 mL) was added. After 30 minutes the organics layers were separated, washed with brine and concentrated in vacuo. The residue was purified by silica column chromatography eluting with 75% EtOAc/hexanes to provide the title compound (60 g, 81% yield) as a cream foam. MS (apci) m/z=374.1 (M+H).

Intermediate 3

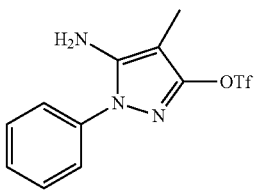 [SMILES: Cc1c(OS(=O)(=O)C(F)(F)F)nn(-c2ccccc2)c1N]

5-amino-4-methyl-1-phenyl-1H-pyrazol-3-yl trifluoromethanesulfonate

Step A: Preparation of 5-amino-4-methyl-1-phenyl-1H-pyrazol-3(2H)-one

A mixture of ethyl 2-cyanopropanoate (50.5 g, 397.2 mmol) and phenylhydrazine (39 mL, 397.2 mmol) in dioxane (100 mL) was heated at 110° C. for 5 days. The cooled mixture was concentrated to ½ volume then cooled in ice and triturated with cold Et₂O. Solids were filtered, washed extensively with Et₂O and dried in vacuo to afford 5-amino-4-methyl-1-phenyl-1H-pyrazol-3(2H)-one (34.69 g, 46% yield) as a fluffy white powder. MS (apci) m/z=190.1 (M+H).

Step B: Preparation of 5-amino-4-methyl-1-phenyl-1H-pyrazol-3-yl trifluoromethane sulfonate A suspension of 5-amino-4-methyl-1-phenyl-1H-pyrazol-3(2H)-one (13.72 g, 72.5 mmol) and N-phenylbis(trifluoromethylsulfonamide) (27.2 g, 76.1 mmol) in DMF (100 mL) was treated with DIEA (37.9 mL, 217.5 mmol) and the mixture stirred at ambient temperature for 16 hours. The mixture was partitioned between sat. NaHCO₃ (400 mL) and EtOAc (200 mL) and the aqueous layer was extracted with EtOAc (2×200 mL). The combined organic phases were washed with water (5×50 mL) and brine (50 mL) then dried over Na₂SO₄, filtered and concentrated in vacuo. The residue was purified by silica column chromatography eluting with 4:1 hexanes/EtOAc, to afford the title compound (23.1 g, 99% yield) as a pale yellow solid. MS (apci) m/z=322.0 (M+H).

Intermediate 4

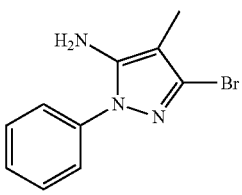

3-bromo-4-methyl-1-phenyl-1H-pyrazol-5-amine

To a suspension of 5-amino-4-methyl-1-phenyl-1H-pyrazol-3(2H)-one [Intermediate 3, step A] (1.60 g, 8.46 mmol) in acetonitrile (30 mL) was added phosphorus oxybromide (3.64 g, 12.7 mmol) in one portion. The mixture was stirred at reflux for 3 hours then cooled and concentrated in vacuo. The residue was treated with DCM (50 mL) then sat. NaHCO₃ (50 mL) was slowly added. The mixture was stirred for 30 minutes then the layers separated and the aqueous layer extracted with DCM (2×50 mL). The combined organic phases were washed with brine (20 mL), dried over Na₂SO₄, filtered and concentrated in vacuo. The residue was purified by silica column chromatography eluting with 2:1 hexanes/EtOAc, to afford the title compound (273 mg, 13% yield) as a white solid. MS (apci) m/z=254.0 (M+H).

Intermediate 5

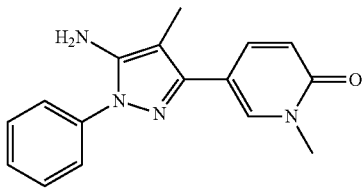 [SMILES: Cc1c(-c2ccc(=O)n(C)c2)nn(-c2ccccc2)c1N]

5-(5-amino-4-methyl-1-phenyl-1H-pyrazol-3-yl)-1-methylpyridin-2(1H)-one

3-Bromo-4-methyl-1-phenyl-1H-pyrazol-5-amine [Intermediate 4] (763 mg, 3.03 mmol), 1-methyl-5-(4,4,5,5-tetramethyl-1,3,2-dioxaborolan-2-yl)pyridin-2(1H)one (1.42 g, 6.05 mmol), K₂CO₃ (1.67 g, 12.1 mmol) and Pd(PPh₃)₄ (350 mg, 0.30 mmol) were combined in toluene (10 mL), water (5 mL) and EtOH (2.5 mL) and warmed to 95° C. in a sealed tube for 16 hours. The cooled mixture was filtered and the filtrate partitioned between water (30 mL) and EtOAc (30 mL). The aqueous layer was extracted with EtOAc (2×20 mL) and the combined organic phases were washed with brine (20 mL), dried over Na₂SO₄, filtered and concentrated in vacuo. The residue was purified by silica column chromatography eluting with 2% MeOH/DCM to afford the title compound (504 mg, 59% yield) as a yellow foam. MS (apci) m/z=281.2 (M+H).

Intermediate 6

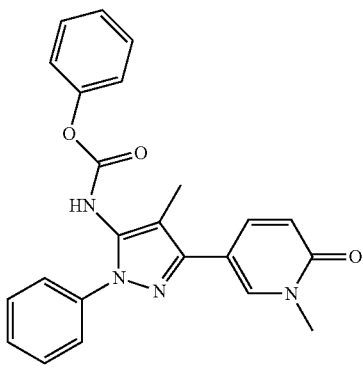 [SMILES: Cc1c(-c2ccc(=O)n(C)c2)nn(-c2ccccc2)c1NC(=O)Oc1ccccc1]

phenyl (4-methyl-3-(1-methyl-6-oxo-1,6-dihydro-pyridin-3-yl)-1-phenyl-1H-pyrazol-5-yl)carbamate To a suspension of 5-(5-amino-4-methyl-1-phenyl-1H-pyrazol-3-yl)-1-methylpyridin-2(1H)-one [Intermediate 5] (2.80 g, 9.99 mmol) in EtOAc (120 mL) was added 2N NaOH (14.98 mL, 29.97 mmol) followed by phenyl chloroformate (2.5 mL, 19.98 mmol). The mixture was stirred at ambient temperature for 16 hours then partitioned between water (100 mL) and EtOAc (100 mL) and the aqueous layer extracted with EtOAc (2×50 mL). The combined organic phases were washed with sat. NaHCO$_3$ (50 mL) and brine (50 mL) then dried over Na$_2$SO$_4$, filtered and concentrated to afford the title compound as a pale yellow syrup which was used directly without purification, assuming 100% yield. MS (apci) m/z=401.2 (M+H).

Intermediate 7

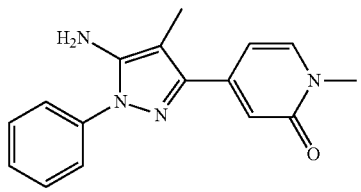 [SMILES: Cc1c(-c2ccn(C)c(=O)c2)nn(-c2ccccc2)c1N]

4-(5-amino-4-methyl-1-phenyl-1H-pyrazol-3-yl)-1-methylpyridin-2(1H)-one

Prepared according to the procedure of Intermediate 5, replacing 3-bromo-4-methyl-1-phenyl-1H-pyrazol-5-amine with 5-amino-4-methyl-1-phenyl-1H-pyrazol-3-yl trifluoromethanesulfonate [Intermediate 3] and 1-methyl-5-(4,4,5,5-tetramethyl-1,3,2-dioxaborolan-2-yl)pyridin-2(1H)one with 1-methyl-4-(4,4,5,5-tetramethyl-1,3,2-dioxaborolan-2-yl)pyridin-2(1H)-one. The product was purified by silica column chromatography eluting with 2% MeOH/DCM to afford the title compound (160 mg, 37% yield) as a pink solid. MS (apci) m/z=281.1 (M+H).

Intermediate 8

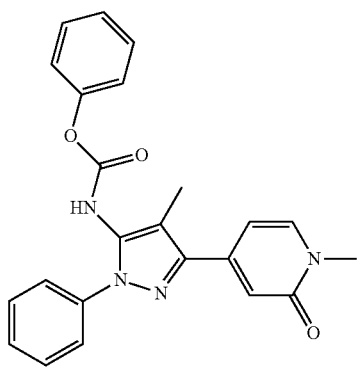 [SMILES: Cc1c(-c2ccn(C)c(=O)c2)nn(-c2ccccc2)c1NC(=O)Oc1ccccc1]

phenyl (4-methyl-3-(1-methyl-2-oxo-1,2-dihydro-pyridin-4-yl)-1-phenyl-1H-pyrazol-5-yl)carbamate Prepared according to the procedure of Intermediate 6, replacing 5-(5-amino-4-methyl-1-phenyl-1H-pyrazol-3-yl)-1-methylpyridin-2(1H)-one with 4-(5-amino-4-methyl-1-phenyl-1H-pyrazol-3-yl)-1-methylpyridin-2(1H)-one. MS (apci) m/z=401.1 (M+H).

Intermediate P107 (Representative Intermediate)

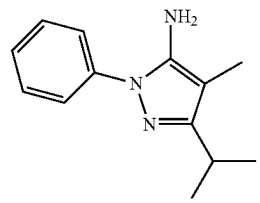 [SMILES: Cc1c(C(C)C)nn(-c2ccccc2)c1N]

3-isopropyl-4-methyl-1-phenyl-1H-pyrazol-5-amine

Step A: Preparation of 2,4-dimethyl-3-oxopentanenitrile

To a solution of propiononitrile (518 mg, 9.40 mmol) in THF (50 mL, 7.83 mmol) at −78° C. under N$_2$ was slowly added lithium bis(trimethylsilyl)amide (1M in THF) (7.83 mL, 7.83 mmol). After 30 minutes, methyl isobutyrate (0.898 mL, 7.83 mmol) was added dropwise, and the reaction mixture was warmed to 0° C. A yellow precipitate formed, the reaction mixture was stirred for 1 hour, then diluted with H$_2$O (50 mL) to dissolve the solids. The mixture was extracted with Et$_2$O (25 mL), and the basic aqueous phase was acidified with 2M HCl (5 mL) and extracted with Et$_2$O (2×50 mL). The combined organic phases were washed with brine (50 mL), dried with MgSO$_4$, filtered, and concentrated to afford the product (421 mg, 42.9% yield)

Step B: Preparation of 3-isopropyl-4-methyl-1-phenyl-1H-pyrazol-5-amine

Prepared by the method as described for Intermediate P1, substituting phenyl hydrazine for ethyl 3-hydrazinylbenzoate hydrochloride and 4,4-dimethyl-3-oxopentanenitrile with 2,4-dimethyl-3-oxopentanenitrile to yield the product as a yellow syrup (0.587 g, 81.1% yield). MS (apci) m/z=216.2 (M+H).

Intermediate P109 (Representative Intermediate)

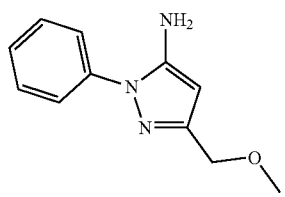

3-(methoxymethyl)-1-phenyl-1H-pyrazol-5-amine

Step A: Preparation of 4-methoxy-3-oxobutanenitrile

To a solution of methyl 2-methoxyacetate (0.4753 mL, 4.803 mmol) in THF (20 mL, 4.803 mmol) at −78° C. under N₂ was added acetonitrile (0.3033 mL, 5.763 mmol), followed by lithium bis(trimethylsilyl)amide (1M in THF) (4.803 mL, 4.803 mmol). After stirring 1 hour, the reaction mixture was warmed to 0° C. and stirred for 1 hour. The reaction mixture was then diluted with H₂O (25 mL), washed with Et₂O (25 mL), then neutralized with 2 M HCl (1.5 mL). This was extracted with Et₂O (2×25 mL) and the combined organic phases were washed with brine (25 mL), dried with MgSO₄, filtered, and concentrated to afford the product (169 mg, 31.1% yield). ¹H NMR (CDCl₃) δ 4.09 (s, 2H), 3.66 (s, 21-1), 3.46 (s, 3H)

Step B: Preparation of 3-(methoxymethyl)-1-phenyl-1H-pyrazol-5-amine

Prepared by the method as described for Intermediate P1, substituting phenyl hydrazine for ethyl 3-hydrazinylbenzoate hydrochloride and 4,4-dimethyl-3-oxopentanenitrile with 4-methoxy-3-oxobutanenitrile to yield the product as a pale yellow residue (6.0 mg, 2.0% yield). MS (apci) m/z=204.0 (M+H).

Intermediate P134

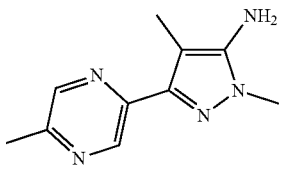

1,4-dimethyl-3-(5-methylpyrazin-2-yl)-1H-pyrazol-5-amine

Prepared by the method as described for Intermediate P107, substituting methyl isobutyrate in Step A with methyl 5-methylpyrazine-2-carboxylate to afford 2-methyl-3-(5-methylpyrazin-2-yl)-3-oxopropanenitrile. In Step B, phenylhydrazine was replaced by methylhydrazine to afford the title compound. MS (apci) m/z=204.1 (M+H).

Intermediate 151

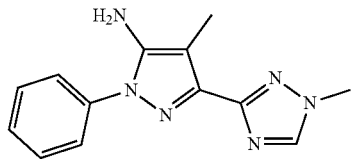

1'-(2-methoxyethyl)-1-phenyl-1H,1'H-[3,4'-bipyrazol]-5-amine

Step A: Preparation of methyl 1-methyl-1H-1,2,4-triazole-3-carboxylate

To a stirred suspension of NaH (60% oil dispersion, 0.346 g, 8.66 mmol) in DMF (20 mL) was added dropwise a solution of methyl 1H-1,2,4-triazole-3-carboxylate (1.00 g, 7.87 mmol) in DMF (20 mL) at 0° C. under nitrogen. The reaction mixture was stirred at 0° C. for 1 hour. MeI (0.982 mL, 15.7 mmol) was added dropwise. The reaction mixture was stirred at ambient temperature overnight. The reaction was poured into cold water and extracted with EtOAc. The combined organic layers were washed with brine, dried and concentrated. The residue was purified by column chromatography (3:1 hexanes/EtOAc) to give the title compound (0.380 g, 34% yield) as a white solid. MS (apci) m/z=142.1 (M+H).

Step B: Preparation of 1'-(2-methoxyethyl)-1-phenyl-1H,1'H-[3,4'-bipyrazol]5-amine Prepared according to the method described for Intermediate P109, using methyl 1-methyl-1H-1,2,4-triazole-3-carboxylate as a replacement for methyl 2-methoxyacetate, and substituting propionitrile for acetonitrile in Step A. MS (apci) m/z=255.1 (M+H).

Intermediate 152

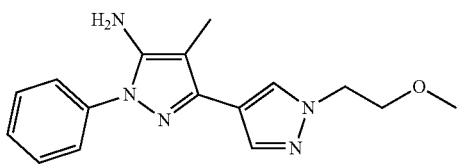 [SMILES: COCCn1cc(-c2nn(-c3ccccc3)c(N)c2C)cn1]

1'-(2-methoxyethyl)-4-methyl-1-phenyl-1H,1'H-[3,4'-bipyrazol]-5-amine

Prepared according to the method described for Intermediate P109, using ethyl 1-(2-methoxyethyl)-1H-pyrazole-4-carboxylate as a replacement for methyl 2-methoxyacetate, and substituting propionitrile for acetonitrile in Step A.

Intermediate 155

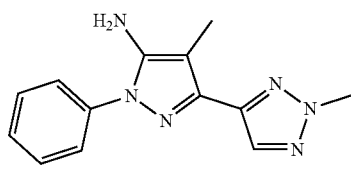 [SMILES: Cc1c(-c2cnn(C)n2)nn(-c2ccccc2)c1N]

4-methyl-3-(2-methyl-2H-1,2,3-triazol-4-yl)-1-phenyl-1H-pyrazol-5-amine

Step A: Preparation of ethyl 2-methyl-2H-1,2,3-triazole-4-carboxylate

A mixture of ethyl 2H-1,2,3-triazole-4-carboxylate (2.00 g, 14.2 mmol), K₂CO₃ (3.53 g, 25.5 mmol) and methyl iodide (3.54 mL, 56.7 mmol) in acetonitrile (40 mL) was stirred at 50° C. under nitrogen overnight. After cooling to ambient temperature, the mixture was filtered through Celite®. The filtrate was concentrated in vacuo. The residue was purified by flash chromatography on silica gel (4:1 hexane/EtOAc) to give the title compound (0.780 g, 35% yield). MS (apci) m/z=156.0 (M+H).

Step B: Preparation of 4-methyl-3-(2-methyl-2H-1,2,3-triazol-4-yl)-1-phenyl 1H-pyrazol-5-amine: Prepared according to the method described for Intermediate P109 using ethyl 2-methyl-2H-1,2,3-triazole-4-carboxylate as a replacement for methyl 2-methoxyacetate, and substituting propionitrile for acetonitrile in Step A. MS (apci) m/z=254.9 (M+H).

Intermediate 171 (Representative Example)

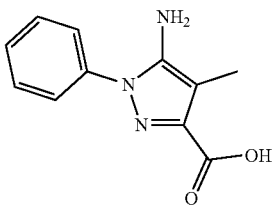 [SMILES: Cc1c(C(=O)O)nn(-c2ccccc2)c1N]

5-amino-4-methyl-1-phenyl-1H-pyrazole-3-carboxylic acid

To a solution of ethyl 5-amino-4-methyl-1-phenyl-1H-pyrazole-3-carboxylate (Intermediate 170, 1.52 mg, 6.21 mmol) in THF (12 mL) and MeOH (6 mL) was added LiOH (2M aq, 9.31 mL, 18.6 mmol). The reaction mixture was stirred at ambient temperature for 19 hours, then partially concentrated under reduced pressure, then neutralized with 6M HCl (3.2 mL), extracted with 10:90 MeOH/DCM (3×25 mL), and the combined organic extracts were washed with brine (50 mL), dried (MgSO$_4$), filtered and concentrated to give the title compound as a yellow solid (1.3 g, 96% yield) MS (apci) m/z=218.1 (M+H).

Intermediate 175

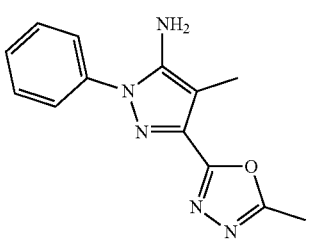 [SMILES: Cc1nnc(-c2nn(-c3ccccc3)c(N)c2C)o1]

4-methyl-3-(5-methyl-1,3,4-oxadiazol-2-yl)-1-phenyl-1H-pyrazol-5-amine

Step A: Preparation of N'-acetyl-5-amino-4-methyl-1-phenyl-1H-pyrazole-3-carbohydrazide To a solution of 5-amino-4-methyl-1-phenyl-1H-pyrazole-3-carboxylic acid (Intermediate 171, 93 mg, 0.428 mmol) in DCM (5 mL) and DIEA (0.149 mL, 0.856 mmol) was added isobutyl carbonochloridate (0.061 mL, 0.471 mmol). The reaction mixture was stirred at ambient temperature for 1 hour, then acetohydrazide (48 mg, 0.642 mmol) was added. The reaction mixture was stirred at ambient temperature for 18 hours, then diluted with H$_2$O (10 mL), extracted DCM (2×10 mL), dried (MgSO$_4$), filtered and concentrated under reduced pressure to afford the product as a pale yellow solid (119 mg, 101% yield). MS (apci) m/z=274.1 (M+H).

Step B: Preparation of 4-methyl-3-(5-methyl-1,3,4-oxadiazol-2-yl)-1-phenyl-1H-pyrazol-5-amine A mixture of N'-acetyl-5-amino-4-methyl-1-phenyl-1H-pyrazole-3-carbohydrazide (117 mg, 0.428 mmol) and POCl$_3$ (0.5 mL) was heated in a pressure tube to 90° C. for 1 hour. The reaction mixture was transferred to a separatory funnel with EtOAc (5 mL), then diluted with saturated aqueous NaHCO$_3$ (20 mL), extracted with EtOAc (2×15 mL), dried (MgSO$_4$), filtered and concentrated. The residue was purified by silica column chromatography eluting with 0-75% acetone/hexanes to afford the title compound as a yellow solid (19.6 mg, 18% yield). MS (apci) m/z=256.1 (M+H).

Intermediate 176

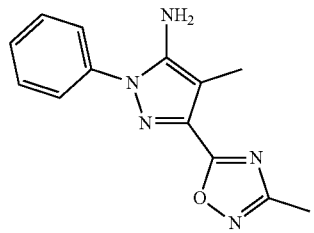 [SMILES: Cc1noc(-c2nn(-c3ccccc3)c(N)c2C)n1]

4-methyl-3-(3-methyl-1,2,4-oxadiazol-5-yl)-1-phenyl-1H-pyrazol-5-amine

To a suspension of NaH (60% in mineral oil, 36 mg, 0.897 mmol) in THF (5 mL) under N$_2$ was added N-hydroxyacetimidamide (66 mg, 0.897 mmol). The reaction mixture was heated to reflux for 1 hour, then cooled to ambient temperature and ethyl 5-amino-4-methyl-1-phenyl-1H-pyrazole-3-carboxylate (Intermediate 170, 200 mg, 0.815 mmol) was added. The reaction mixture was heated to reflux for 18 hours, then cooled to ambient temperature and additional NaH (60% in mineral oil, 18 mg, 0.449 mmol) was added. The reaction mixture was heated to reflux for 4 hours, then diluted with H$_2$O (10 mL), extracted DCM (2×15 mL), and the combined organic extracts were dried (MgSO$_4$), filtered and concentrated under reduced pressure. The residue was purified by silica column chromatography eluting with 0-50% acetone/hexanes to afford the title compound as an orange solid (84 mg, 40% yield). MS (apci) m/z=256.1 (M+H).

Intermediate 178

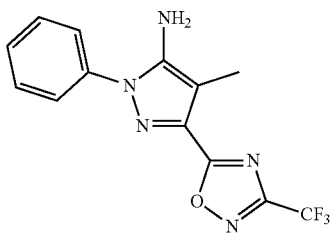 [SMILES: Cc1c(-c2nc(C(F)(F)F)no2)nn(-c2ccccc2)c1N]

4-methyl-1-phenyl-3-(3-(trifluoromethyl)-1,2,4-oxadiazol-5-yl)-1H-pyrazol-5-amine

Step A: Preparation of 2,2,2-trifluoro-N'-hydroxyacetimidamide

To a suspension of hydroxylamine hydrochloride (5.45 g, 78.4 mmol) in MeOH (100 mL) was added NaOMe (25 wt % solution in MeOH, 17.9 mL, 78.4 mmol) and the mixture stirred at ambient temperature for 10 minutes, then filtered and the solid was washed with MeOH. The filtrate was cooled to 0° C. and then 2,2,2-trifluoroacetonitrile (7.45 g, 78.4 mmol) gas was bubbled into the solution over 30 minutes. The reaction mixture was then allowed to warm to ambient temperature for 19 hours. The solution was concentrated under reduced pressure to 50 mL and the solids were filtered. The filtrate was concentrated, re-suspended in cold MeOH, and filtered. The filtrate was concentrated, again re-suspended in cold MeOH, and filtered. The filtrate was concentrated to give the product as a waxy white solid (6.7 g, 67% yield). $^1$H NMR (CD$_3$CN) δ 8.32 (s, 1H), 5.25 (br s, 2H). $^{19}$F NMR (CD$_3$CN) 8-71.8 (s).

Step B: Preparation of 4-methyl-1-phenyl-3-(3-(trifluoromethyl)-1,2,4-oxadiazol-5-yl)-1H-pyrazol-5-amine To a suspension of NaH (60% in mineral oil, 356 mg, 0.897 mmol) in THF (5 mL, 0.815 mmol) under N$_2$ was added 2,2,2-trifluoro-N'-hydroxyacetimidamide (115 mg, 0.897 mmol). The reaction mixture was heated to reflux for 1 hour, then cooled to ambient temperature and powdered 4A molecular sieves (200 mg) and ethyl 5-amino-4-methyl-1-phenyl-1H-pyrazole-3-carboxylate (Intermediate 170; 200 mg, 0.815 mmol) were added and heated to reflux. The reaction mixture was heated to reflux for 18 hours, then filtered, diluted with H$_2$O (15 mL), extracted DCM (2×25 mL), and the combined organic extracts were washed with brine (25 mL), dried (MgSO$_4$), filtered and concentrated under reduced pressure. The residue was purified by silica column chromatography eluting with 0-50% acetone/hexanes to afford the title compound as a white solid (44 mg, 17% yield). MS (apci) m/z=310.1 (M+H).

Intermediate 189 (Representative Example)

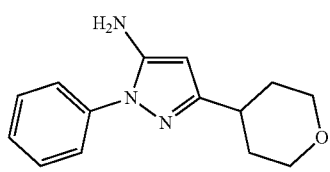 [SMILES: Nc1cc(C2CCOCC2)nn1-c1ccccc1]

1-phenyl-3-(tetrahydro-2H-pyran-4-yl)-1H-pyrazol-5-amine

Step A: 3-oxo-3-(tetrahydro-2H-pyran-4-yl)propanenitrile

A 1M solution of LHMDS in dry THF (26.3 mL, 26.3 mmol) was cooled to −78° C. and acetonitrile (1.43 mL, 27.5 mmol) was added dropwise over 2 minutes. The mixture was stirred at −78° C. for 1 hour and a solution of methyl tetrahydro-2H-pyran-4-carboxylate (3.41 mL, 25.0 mmol) in dry THF (12 mL) was added. The mixture was stirred for 1 hour, the dry ice bath was removed and the mixture allowed to reach ambient temperature. The mixture was poured into chilled H$_2$O (250 mL) and was extracted with Et$_2$O (3×). The aqueous portion was cooled to 0° C. and 6M HCl was added dropwise to pH=3 (starting pH=12). The mixture was extracted with EtOAc (3×) and the combined extracts were dried over MgSO$_4$. The solution eluted through a SiO$_2$ plug eluting with EtOAc. The filtrate was concentrated to give the title compound as a colorless oil (2.52 g, 66%). $^1$H NMR (CDCl$_3$) δ 3.99-4.06 (m, 2H), 3.54 (s, 211), 3.46 (t, 2H), 2.76-2.86 (m, 1H), 1.70-1.86 (m, 4H).

Step B: 1-phenyl-3-(tetrahydro-2H-pyran-4-yl)-1H-pyrazol-5-amine

To a solution of 3-oxo-3-(tetrahydro-2H-pyran-4-yl)propanenitrile (2.30 g, 12.8 mmol) in absolute EtOH (35 mL) was added phenylhydrazine hydrochloride (2.21 g, 15.3 mmol) and the mixture was heated at reflux until complete by TLC (5 hours). The mixture was cooled to ambient temperature and was concentrated. The residue was partitioned in H$_2$O (75 mL) and EtOAc (40 mL). 2M NaOH was added to pH=5 with vigorous mixing, the organic layer was removed and the aqueous was extracted with EtOAc (2×). The combined EtOAc fractions were washed with H$_2$O and saturated NaCl. The solution was diluted with an equal volume of hexanes, dried over MgSO$_4$/activated carbon and eluted through a SiO$_2$ plug eluting with 50% EtOAc-hexanes. The filtrate was concentrated to give a gold syrup. The syrup was treated with Et$_2$O and stirred until a fine, granular suspension formed. The solid was collected, washed with Et$_2$O and dried in vacuum to furnish the title compound as a white solid (2.01 g, 65%). $^1$H NMR (CDCl$_3$) δ 7.55 (d, 2H), 7.46 (t, 2H), 7.32 (t, 1H), 5.49 (s, 1H), 4.00-4.08 (m, 2H), 3.97 (br s, 2H), 3.52 (dt, 2H), 2.86 (m, 1H) 1.73-1.93 (m, 4H).

The following compound was prepared according to the method used for the preparation of 1-phenyl-3-(tetrahydro-2H-pyran-4-yl)-1H-pyrazol-5-amine (Intermediate 189) using either acetonitrile or propiononitrile in Step A in conjunction with the appropriate ester.

| Intermediate # | Structure | Data |
|---|---|---|
| 193 | ![structure] | $^1$H NMR (CDCl$_3$) δ 7.60 (d, 2H), 7.49 (t, 2H), 7.37 (t, 1H), 6.45 (s, 1H), 3.67 (br s, 2H), 2.45 (s, 3H), 2.24 (s, 3H). |

Intermediate 199

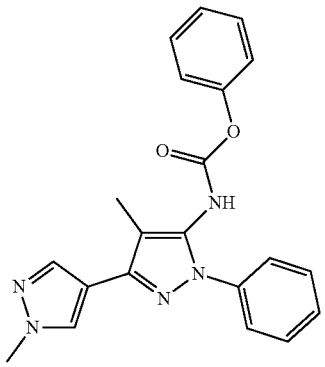 [SMILES: Cc1c(-c2cnn(C)c2)nn(-c2ccccc2)c1NC(=O)Oc1ccccc1]

Phenyl 1',4-dimethyl-1-phenyl-1H,1'H-3,4'-bipyrazol-5-ylcarbamate

Step A: ethyl 1-methyl-1H-pyrazole-4-carboxylate

To a 3000-mL three-necked flask was added ethyl 2-formyl-3-oxopropanoate (100 g, 694 mmol), followed by anhydrous 200-proof EtOH (694 mL) to obtain a clear yellowish solution. The reaction was cooled in an ice bath to 5° C., and then methylhydrazine (35.8 mL, 680 mmol) was added dropwise. A vigorous exotherm was observed during hydrazine addition and the temperature was kept below 12° C. by controlling the addition rate. After the hydrazine addition was complete, the ice bath was removed, and the reaction was allowed to stir at ambient temperature overnight. The reaction was concentrated on a rotary evaporator to a crude orange oil. The crude was taken up in DCM and re-concentrated, then on high vacuum for 2 days to yield tan orange oil. LC/MS and $^1$H NMR showed essentially pure ethyl 1-methyl-1H-pyrazole-4-carboxylate (106 g, 99.1%).

Step B: 2-methyl-3-(1-methyl-1H-pyrazol-4-yl)-3-oxopropanenitrile

To a four-necked 5-liter round bottomed flask fitted with an overhead stirrer and addition funnel was charged LHMDS (1444 mL, 1444 mmol) (1.0M in THF). The solution was cooled in an acetone/dry ice bath first (internal temperature of −79° C.) under nitrogen, followed by slow addition of propiononitrile (103 mL, 1444 mmol) via dropping funnel. The mixture was stirred at −80° C. for 90 minutes. A solution of ethyl 1-methyl-1H-pyrazole-4-carboxylate (106 g, 688 mmol) in anhydrous THF (500 mL) was then introduced dropwise via an addition funnel (addition time: about 45 minutes; internal temperature during addition remained below −76° C.). After the addition was complete, the reaction was allowed to slowly warm to ambient temperature and stirred overnight. An orange glass deposited on the bottom of the flask. The organics were decanted and the glass was dissolved in warm water. The mixture was washed with ether (3×1000 mL). The aqueous phase was then pH-adjusted to 5 (pH paper) using concentrated HCl and saturated bicarbonate solution The aqueous layer was extracted with DCM (3×1000 mL) The combined organic extracts were dried over MgSO$_4$ filtered and concentrated to yield the 2-methyl-3-(1-methyl-1H-pyrazol-4-yl)-3-oxopropanenitrile as an amber oil (92 g, 82%). MS (apci) m/z=162.1 (M−H).

Step C: 1',4-dimethyl-1-phenyl-1H,1'H-3,4'-bipyrazol-5-amine

A 3 L, 3 necked round bottomed flask was charged with 2-methyl-3-(1-methyl-1H-pyrazol-4-yl)-3-oxopropanenitrile (60 g, 368 mmol) absolute anhydrous ethanol (1000 mL) and phenylhydrazine hydrochloride (58 g, 404 mmol) at ambient temperature to form a yellowish suspension. The reaction vessel was equipped with a water condenser and refluxed (using a heating mantle) overnight. The reaction was concentrated and 1M NaOH (1 L) was added and the solid was broken up and collected. The solid was washed with water and hexanes. A second crop crashed out in the filtrate and was collected. The combined solids were crushed and triturated with ether (500 mL). The solid was collected filtration, washed with hexanes and air dried under vacuum to provide 1',4-dimethyl-1-phenyl-1H,1'H-3,4'-bipyrazol-5-amine (93 g, 100%).

Step D: phenyl 1',4-dimethyl-1-phenyl-1H,1'H-3,4'-bipyrazol-5-ylcarbamate

In a 3 L, round bottomed flask was charged with 1',4-dimethyl-1-phenyl-1H,1'H-3,4'-bipyrazol-5-amine (50 g, 197.4 mmol) and EtOAc (1000 mL) to obtain a clear brownish solution. To this was added NaOH (2M aq) (500 mL) in one portion to obtain a turbid mixture (both the aqueous and organic layers were clear but a precipitate was observed in between the two layers). After 3 minutes, phenyl carbonochloridate (74.29 mL, 592.2 mmol) was added slowly at ambient temperature exotherm to 33° C. The reaction stirred at ambient temperature for 2 hours. Additional phenyl carbonochloridate (10 mL) was added. After 30 minutes the organics were separated, washed with brine and concentrated in vacuo. The product was purified by silica gel chromatography (eluting with 75% ethyl acetate in hexanes) to provide phenyl 1',4-dimethyl-1-phenyl-1H,1'H-3,4'-bipyrazol-5-ylcarbamate (60 g, 81.4%).

Intermediate 200

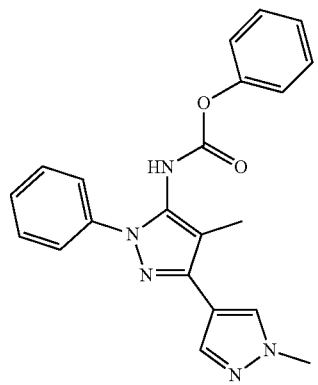 [SMILES: Cc1c(-c2cnn(C)c2)nn(-c2ccccc2)c1NC(=O)Oc1ccccc1]

phenyl 1',4-dimethyl-1-phenyl-1H,1'H-3,4'-bipyrazol-5-ylcarbamate

A 3 L, round bottomed flask was charged with 1',4-dimethyl-1-phenyl-1H,1'H-3,4'-bipyrazol-5-amine (50 g, 197.4 mmol) and EtOAc (1000 mL) to obtain a clear brownish solution. To this was added NaOH (2M aq) (500 mL) in one portion to obtain a turbid mixture (the aqueous and organic layers were clear, but a precipitate was observed in between the two layers). After 3 minutes, phenyl carbonochloridate (74.29 mL, 592.2 mmol) was added slowly at ambient temperature (the temperature of the reaction mixture increased to 33° C. during the addition). The reaction stirred at ambient temperature for 2 hours. Additional phenyl carbonochloridate (10 mL) was added. After 30 minutes the organics layers were separated, washed with brine and concentrated in vacuo. The residue was purified by silica gel chromatography (eluting with 75% ethyl acetate in hexanes) to provide phenyl 1',4-dimethyl-1-phenyl-1H,1'H-3,4'-bipyrazol-5-ylcarbamate (60 g, 81.4%).

The following compounds were prepared according to the method describe for the preparation of Intermediate 200, using the appropriate amino pyrazole intermediate.

| Intermediate # | Structure | Name | Data |
|---|---|---|---|
| 214 | 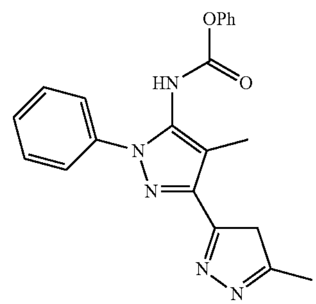 [SMILES: CC1=NN=C(c2nn(-c3ccccc3)c(NC(=O)Oc3ccccc3)c2C)C1] | phenyl (4-methyl-3-(5-methyl-1,3,4-oxadiazol-2-yl)-1-phenyl-1H-pyrazol-5-yl)carbamate | MS (apci) m/z = 376.1 (M + H). |
| 215 | 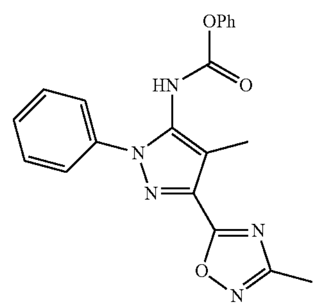 [SMILES: Cc1noc(-c2nn(-c3ccccc3)c(NC(=O)Oc3ccccc3)c2C)n1] | phenyl 4-methyl-3-(3-methyl-1,2,4-oxadiazol-5-yl)-1-phenyl-1H-pyrazol-5-ylcarbamate | MS (apci) m/z = 376.1 (M + H). |
| 216 | 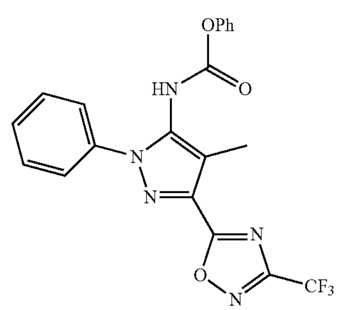 [SMILES: Cc1c(-c2nc(C(F)(F)F)no2)nn(-c2ccccc2)c1NC(=O)Oc1ccccc1] | phenyl 4-methyl-1-phenyl-3-(3-(trifluoromethyl)-1,2,4-oxadiazol-5-yl)-1H-pyrazol-5-ylcarbamate | MS (apci) m/z = 430.1 (M + H). |
| 220 | 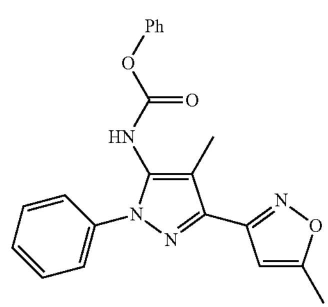 [SMILES: Cc1cc(-c2nn(-c3ccccc3)c(NC(=O)Oc3ccccc3)c2C)no1] | phenyl (4-methyl-3-(5-methylisoxazol-3-yl)-1-phenyl-1H-pyrazol-5-yl)carbamate | $^1$H NMR (CDCl$_3$) δ 7.54 (d, 2H), 7.49 (t, 2H), 7.41 (t, 1H), 7.33 (br s, 2H), 7.20 (br s, 1H), 7.08 (br s, 1H), 6.74 (br s, 1H), 6.66 (br s, 1H), 6.48 (s, 1H), 2.45 (s, 3H) 2.34 (s, 3H) |

Intermediate 245

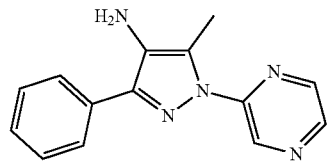 [SMILES: Cc1c(N)c(-c2ccccc2)nn1-c1cnccn1]

5-methyl-3-phenyl-1-(pyrazin-2-yl)-1H-pyrazol-4-amine

Step A: 2-(5-methyl-4-nitroso-3-phenyl-1H-pyrazol-1-yl)pyrazine

To a solution of 2-hydrazinylpyrazine (0.485 g, 4.40 mmol) in HOAc (6 mL) was added (2-(hydroxyimino)-1-phenylbutane-1,3-dione (0.765 g, 4.00 mmol) in small portions over 2 minutes. The mixture was stirred for 5 minutes and the resulting light orange suspension was stirred at 60° C. for 6 hours. EtOH (1 mL) was added and the mixture was heated at 60° C. for an additional 6 hours. The resulting dark green suspension was cooled to ambient temperature and the mixture was diluted with H$_2$O (30 mL). The green suspension was stirred for 1 hour and the solid was collected via vacuum filtration. The collected solid was washed with H$_2$O and dried in vacuum. The solid was suspended in EtOH (25 mL) and concentrated HCl (500 µL) was added. The mixture was heated at reflux for 20 hours, cooled to ambient temperature and diluted with chilled H$_2$O (75 mL). The mixture was treated with 1M NaOH to pH=7 and was extracted with Et$_2$O (3x). The combined extracts were washed with saturated NaCl and dried over MgSO$_4$. The dried solution was filtered through packed Celite® and concentrated. The residual green-yellow solid was purified on a SiO$_2$ column using step gradient elution (25% CH$_2$Cl$_2$, 50% EtOAc/hexanes) to furnish the title compound as a turquoise solid (325 mg, 31%). MS (apci) m/z=266.1 (M+H).

Step B: 5-methyl-3-phenyl-1-(pyrazin-2-yl)-1H-pyrazol-4-amine

To a mixture of 2-(5-methyl-4-nitroso-3-phenyl-1H-pyrazol-1-yl)pyrazine (325 mg, 1.04 mmol) and Zn dust (340 mg, 5.21 mmol) in EtOH (10 mL) was added concentrated HCl (95.5 µL, 1.15 mmol). The mixture was stirred at ambient temperature for 17 hours, then at 65° C. for 3 hours. The mixture was cooled to ambient temperature and was filtered through packed Celite® eluting with MeOH. The eluent was concentrated, and the residue was treated with H$_2$O and mixed. The resulting orange suspension treated with 2M HCl to pH=1 and the mixture was extracted with Et$_2$O (3x). The aqueous portion was treated with 2M NaOH to pH=8 and extracted with EtOAc (3x). The combined EtOAc extracts were washed with saturated NaCl and dried over MgSO$_4$/activated carbon. The solution was eluted through a SiO$_2$ plug eluting with EtOAc. The eluent was concentrated to give the title compound as a light yellow wax (33 mg, 13%). MS (esi) m/z=252.2 (M+H).

Intermediate 246

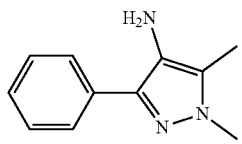

1,5-dimethyl-3-phenyl-1H-pyrazol-4-amine

Step A: 1,5-dimethyl-4-nitroso-3-phenyl-1H-pyrazole

To a solution of methylhydrazine (0.484 g, 10.5 mmol) in HOAc (10 mL) was added 2-(hydroxyimino)-1-phenylbutane-1,3-dione (2.01 g, 10.5 mmol) in small portions over 5 minutes. The reaction mixture was heated at 60° C. for 1 hour and was cooled to ambient temperature. Et$_2$O (50 mL) and H$_2$O (10 mL) were added to the mixture followed by slow addition of saturated Na$_2$CO$_3$ until pH=8 was obtained. The organic layer was removed and the aqueous layer was extracted with Et$_2$O (2x). The combined organic fractions were dried over Na$_2$SO$_4$, filtered and concentrated. The residue was purified by silica gel chromatography (1:5 EtOAc/hexanes) to give the title compound as a green solid (1.32 g, 63%). MS (apci) m/z=202.1 (M+H).

Step B: 1,5-dimethyl-3-phenyl-1H-pyrazol-4-amine

To a solution of 1,5-dimethyl-4-nitroso-3-phenyl-1H-pyrazole (1.32 g, 6.60 mmol) in MeOH (50 mL) was added Pd(OH)$_2$ on carbon (200 mg, 20 wt %, 0.286 mmol) and the reaction mixture was shaken under 50 psi of H$_2$ for 3 hours at ambient temperature. The reaction mixture was evacuated, purged with N$_2$ filtered through a pad of Celite® with MeOH elution. The eluent was concentrated and the residue dried in vacuum to provide the title compound as a tan solid (1.23 g, 100%). MS (apci) m/z=188.1 (M+H).

Intermediate A

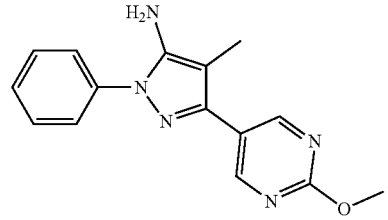 [SMILES: COc1ncc(-c2nn(-c3ccccc3)c(N)c2C)cn1]

3-(2-methoxypyrimidin-5-yl)-4-methyl-1-phenyl-1H-pyrazol-5-amine

Step A: 5-amino-4-methyl-1-phenyl-1H-pyrazol-3(2H)-one

A mixture of ethyl 2-cyanopropanoate (50.5 g, 397.2 mmol) and phenylhydrazine (39 mL, 397.2 mmol) in dioxane (100 mL) was heated at 110° C. for 5 days. The cooled mixture was concentrated to ½ volume, then cooled in ice and triturated with cold Et$_2$O. The resulting solids were filtered, washed extensively with Et$_2$O and dried under vacuum to afford 5-amino-4-methyl-1-phenyl-1H-pyrazol-3(2H)-one (34.69 g, 46% yield) as a fluffy white powder. MS (apci) m/z=190.1 (M+H).

Step B: 5-amino-4-methyl-1-phenyl-1H-pyrazol-3-yl trifluoromethane sulfonate

A suspension of 5-amino-4-methyl-1-phenyl-1H-pyrazol-3(2H)-one (13.72 g, 72.5 mmol) and N-phenylbis(trifluoromethylsulfonamide) (27.2 g, 76.1 mmol) in DMF (100 mL) was treated with DIEA (37.9 mL, 217.5 mmol) and the mixture was stirred at ambient temperature for 16 hours. The mixture was partitioned between saturated NaHCO$_3$ and EtOAc and the aqueous layer was extracted with EtOAc. The combined organic phases were washed with water and brine (50 mL), then dried over Na$_2$SO$_4$, filtered and concentrated under vacuum The residue was purified by silica column chromatography eluting with 4:1 hexanes/EtOAc, to afford the title compound (23.1 g, 99% yield) as a pale yellow solid. MS (apci) m/z=322.0 (M+H).

Step C: Preparation of 3-(2-methoxypyrimidin-5-yl)-4-methyl-1-phenyl-1H-pyrazol-5-amine 5-amino-4-methyl-1-phenyl-1H-pyrazol-3-yl trifluoromethane sulfonate (7.5 g, 23.3 mmol), (2-methoxypyrimidin-5-yl)boronic acid (5.39 g, 35.0 mmol), K$_2$CO$_3$ (12.9 g, 93.4 mmol) and Pd(PPh$_3$)$_4$ (2.7 g, 2.33 mmol) were combined in toluene (40 mL), water (20 mL) and EtOH (10 mL) and warmed to 95° C. in a sealed tube for 18 hours. The cooled mixture was filtered through GF paper and the filtrate was partitioned between water (200 mL) and EtOAc (200 mL). The aqueous layer was extracted with EtOAc (2×100 mL) and the combined organic phases were washed with brine (100 mL), dried over Na$_2$SO$_4$, filtered and concentrated under vacuum. The residue was purified by silica column chromatography eluting with 1% MeOH/DCM to afford 3-(2-methoxypyrimidin-5-yl)-4-methyl-1-phenyl-1H-pyrazol-5-amine (4.3 g, 46% yield) as a foam. MS (apci) m/z=282.1 (M+H).

Intermediate B

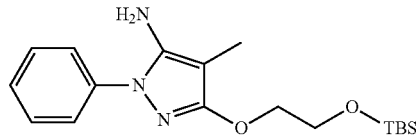

3-(2-((tert-butyldimethylsilyl)oxy)ethoxy)-4-methyl-1-phenyl-1H-pyrazol-5-amine

Step A: 5-amino-4-methyl-1-phenyl-1H-pyrazol-3(2H)-one

A mixture of ethyl 2-cyanopropanoate (50.5 g, 397.2 mmol) and phenylhydrazine (39 mL, 397.2 mmol) in dioxane (100 mL) was heated at 110° C. for 5 days. The cooled mixture was concentrated to ½ volume, then cooled in an ice bath and triturated with cold Et$_2$O. The resulting solids were filtered, washed extensively with Et$_2$O and dried under vacuum to afford 5-amino-4-methyl-1-phenyl-1H-pyrazol-3(2H)-one (34.69 g, 46% yield) as a fluffy white powder. MS (apci) m/z=190.1 (M+H).

Step B: 3-(2-((tert-butyldimethylsilyl)oxy)ethoxy)-4-methyl-1-phenyl-1H-pyrazol-5-amine To a solution of 5-amino-4-methyl-1-phenyl-1H-pyrazol-3(2H)-one (500 mg, 2.643 mmol) in DMF (5 mL) were added K$_2$CO$_3$ (730 mg, 5.285 mmol) then (2-bromoethoxy)(tert-butyl)dimethylsilane (1.134 mL, 5.285 mmol). The reaction mixture was heated to 60° C. for 17 hours, then cooled to ambient temperature. The reaction mixture was filtered, diluted with EtOAc (60 mL), washed with water and brine, dried (MgSO$_4$), filtered and concentrated. The crude product was purified by silica column chromatography eluting with 0-40% acetone/hexane, to afford the title compound (388 mg, 42% yield) as a waxy off-white solid. MS (apci) m/z=348.2 (M+H).

Synthetic Examples

Example 1 (Representative Compound)

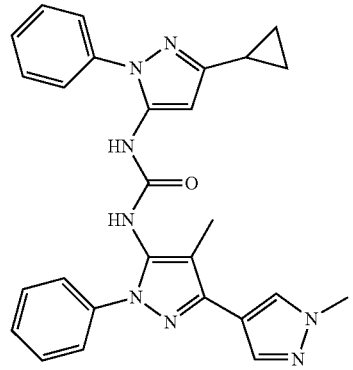 [SMILES: Cc1c(-c2cnn(C)c2)nn(-c2ccccc2)c1NC(=O)Nc1cc(C2CC2)nn1-c1ccccc1]

1-(3-cyclopropyl-1-phenyl-1H-pyrazol-5-yl)-3-(1',4-dimethyl-1-phenyl-1H,1'H-[3,4'-bipyrazol]-5-yl)urea To a solution of phenyl (1',4-dimethyl-1-phenyl-1H,1'H-[3,4'-bipyrazol]-5-yl)carbamate (Intermediate 2, 50 mg, 0.134 mmol) in DMF (0.6 mL) were added 3-cyclopropyl-1-phenyl-1H-pyrazol-5-amine (Oakwood, 26.7 mg, 0.134 mmol) and DIEA (0.047 mL, 0.268 mmol). The reaction mixture was stirred at 60° C. for 2 days. The reaction mixture was purified by silica column chromatography, eluting with 0-90% acetone in hexanes to afford the title compound as a white solid (11.3 mg, 18% yield). MS (apci) m/z=479.2 (M+H).

Example 2 (Representative Compound)

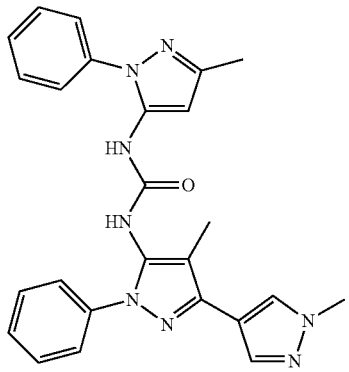 [SMILES: Cc1cc(NC(=O)Nc2c(C)c(-c3cnn(C)c3)nn2-c2ccccc2)n(-c2ccccc2)n1]

1-(1',4-dimethyl-1-phenyl-1H,1'H-[3,4'-bipyrazol]-5-yl)-3-(3-methyl-1-phenyl-1H-pyrazol-5-yl)urea Prepared according to the procedure of Example 1, replacing 3-cyclopropyl-1-phenyl-1H-pyrazol-5-amine with 3-methyl-1-phenyl-1H-pyrazol-5-amine (Aldrich, 23.2 mg, 0.134 mmol). The reaction mixture was purified by reverse-phase column chromatography, eluting with 0-90% acetonitrile/water, to afford the title compound as a white solid (7.6 mg, 13% yield). MS (apci) m/z=453.2 (M+H).

Example 3 (Representative Compound)

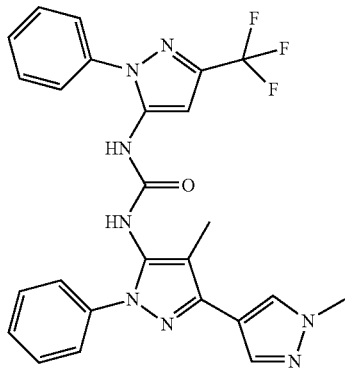 [SMILES: Cc1c(-c2cnn(C)c2)nn(-c2ccccc2)c1NC(=O)Nc1cc(C(F)(F)F)nn1-c1ccccc1]

1-(1',4-dimethyl-1-phenyl-1H,1'H-[3,4'-bipyrazol]-5-yl)-3-(1-phenyl-3-(trifluoromethyl)-1H-pyrazol-5-yl)urea Prepared according to the procedure of Example 1, replacing 3-cyclopropyl-1-phenyl-1H-pyrazol-5-amine with 1-phenyl-3-(trifluoromethyl)-1H-pyrazol-5-amine (ChemImpex, 30.4 mg, 0.134 mmol). The reaction mixture was purified by reverse-phase column chromatography, eluting with 0-90% acetonitrile/water, to afford the title compound as a white solid (7.5 mg, 11% yield). MS (apci) m/z=507.2 (M+H).

Example 4

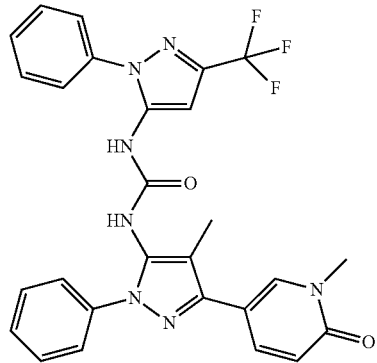 [SMILES: Cc1c(-c2ccc(=O)n(C)c2)nn(-c2ccccc2)c1NC(=O)Nc1cc(C(F)(F)F)nn1-c1ccccc1]

1-(4-methyl-3-(1-methyl-6-oxo-1,6-dihydropyridin-3-yl)-1-phenyl-1H-pyrazol-5-yl)-3-(1-phenyl-3-(trifluoromethyl)-1H-pyrazol-5-yl)urea Prepared according to the procedure of Example 3, replacing phenyl (1',4-dimethyl-1-phenyl-1H,1'H-[3,4'-bipyrazol]-5-yl)carbamate with phenyl (4-methyl-3-(1-methyl-6-oxo-1,6-dihydropyridin-3-yl)-1-phenyl-1H-pyrazol-5-yl)carbamate (Intermediate 6, 50 mg, 0.125 mmol). The reaction mixture was purified by silica column chromatography, eluting with 0-80% acetone in hexanes, to afford the title compound as a white solid (7.1 mg, 11% yield). MS (apci) m/z=534.2 (M+H).

Example 5

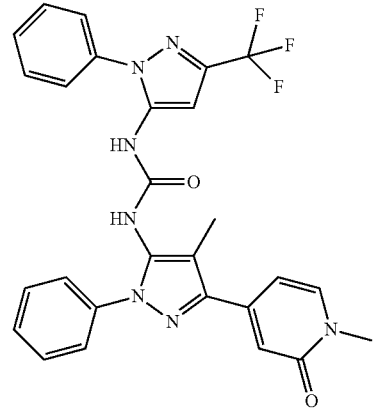 [SMILES: Cc1c(-c2ccn(C)c(=O)c2)nn(-c2ccccc2)c1NC(=O)Nc1cc(C(F)(F)F)nn1-c1ccccc1]

1-(4-methyl-3-(1-methyl-2-oxo-1,2-dihydropyridin-4-yl)-1-phenyl-1H-pyrazol-5-yl)-3-(1-phenyl-3-(trifluoromethyl)-1H-pyrazol-5-yl)urea Prepared according to the procedure of Example 4, replacing phenyl (4-methyl-3-(1-methyl-6-oxo-1,6-dihydropyridin-3-yl)-1-phenyl-1H-pyrazol-5-yl)carbamate with phenyl (4-methyl-3-(1-methyl-2-oxo-1,2-dihydropyridin-4-yl)-1-phenyl-1H-pyrazol-5-yl)carbamate (Intermediate 8, 50 mg, 0.125 mmol). The reaction mixture was purified by reverse-phase column chromatography, eluting with 5-70% acetonitrile/water, to afford the title compound as a white solid (1.0 mg, 2% yield). MS (apci) m/z=534.2 (M+H).

Example 6

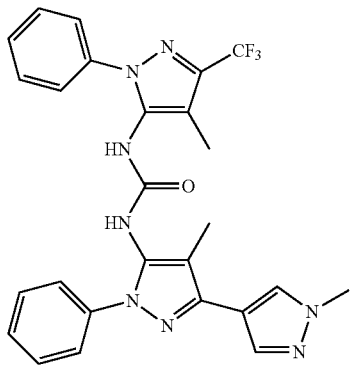 [SMILES: Cc1c(-c2cnn(C)c2)nn(-c2ccccc2)c1NC(=O)Nc1c(C)c(C(F)(F)F)nn1-c1ccccc1]

1-(1',4-dimethyl-1-phenyl-1H,1'H-[3,4'-bipyrazol]-5-yl)-3-(4-methyl-1-phenyl-3-(trifluoromethyl)-1H-pyrazol-5-yl)urea Step A: Preparation of 4,4,4-trifluoro-2-methyl-3-oxobutanenitrile To a solution of lithium bis(trimethylsilyl)amide (1M in THF, 14.78 ml, 14.78 mmol) in THF (40 mL) under $N_2$ at −78° C. was added propiononitrile (0.983 mL, 16.89 mmol) dropwise over 2 minutes. The reaction mixture was stirred at −78° C. for 90 minutes, then ethyl 2,2,2-trifluoroacetate (1.68 mL, 14.08 mmol) was added dropwise over 5 minutes. The reaction mixture was stirred at −78° C. for 30 minutes, then stirred at 0° C. for 1 hour, then diluted with $H_2O$ (100 mL) and extracted with $Et_2O$ (100 mL). The aqueous phase was neutralized with 2M aq. HCl (7 mL), then extracted with $Et_2O$ (3×100 mL). The combined organic phases were washed with brine (100 mL), dried over $MgSO_4$, filtered and partially concentrated to afford the product as a pale yellow oil (3.93 g, 184% yield) containing $Et_2O$ and THF, which was used in the following step without further purification. $^1H$ NMR (CDCl$_3$) δ 3.76 (m, 6H, THF), 3.48 (q, 0.5H, $Et_2O$), 3.20 (q, 1H, product), 1.86 (m, 6H, THF), 1.50 (d, 3H, product), 1.21 (t, 0.8H, $Et_2O$).

Step B: Preparation of 4-methyl-1-phenyl-3-(trifluoromethyl)-1H-pyrazol-5-amine

To 4,4,4-trifluoro-2-methyl-3-oxobutanenitrile (containing THF and $Et_2O$, assuming theoretical mass of 2127 mg, 14.08 mmol) were added EtOH (50 mL) and phenylhydrazine hydrochloride (2036 mg, 14.08 mmol). The reaction mixture was heated to reflux for 18 hours, then concentrated, diluted with sat. aq. NaHCO$_3$ (100 mL), extracted with DCM (3×100 mL), and the combined organic phases were washed with brine (100 mL), dried over MgSO$_4$, filtered and concentrated. The crude product was purified by silica column chromatography, eluting with 0-25% acetone in hexanes, to afford the title compound as a peach solid (2.30 g, 68% yield over 2 steps). MS (apci) m/z=242.1 (M+H).

Step C: Preparation of 1-(4-methyl-3-(1-methyl-2-oxo-1,2-dihydropyridin-4-yl)-1-phenyl-1H-pyrazol-5-yl)-3-(1-phenyl-3-(trifluoromethyl)-1H-pyrazol-5-yl)urea To a solution of 4-methyl-1-phenyl-3-(trifluoromethyl)-1H-pyrazol-5-amine (32.3 mg, 0.134 mmol) in DIEA (0.047 mL, 0.268 mmol) and DMF (0.6 mL) was added phenyl (1',4-dimethyl-1-phenyl-1H,1'H-[3,4'-bipyrazol]-5-yl)carbamate (Intermediate 2, 50 mg, 0.134 mmol). The reaction mixture was stirred at ambient temperature for 14 hours. The reaction mixture was purified by silica column chromatography, eluting with 0-85% acetone in hexanes to afford the title compound as a white solid (12.3 mg, 18% yield). MS (apci) m/z=521.2 (M+H).

Example 7 (Representative Compound)

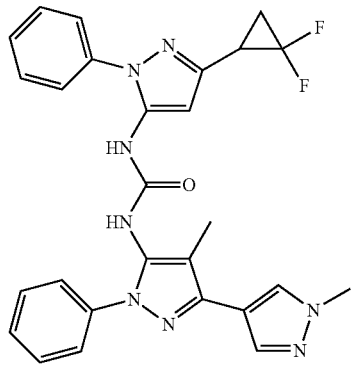 [SMILES: Cc1c(-c2cnn(C)c2)nn(-c2ccccc2)c1NC(=O)Nc1cc(C2CC2(F)F)nn1-c1ccccc1]

1-(3-(2,2-difluorocyclopropyl)-1-phenyl-1H-pyrazol-5-yl)-3-(1',4-dimethyl-1-phenyl-1H,1'H-[3,4'-bipyrazol]-5-yl)urea Step A: Preparation of phenyl 2,2-difluorocyclopropanecarboxylate To a solution of 2,2-difluorocyclopropanecarboxylic acid (Aldrich, 1.00 g, 8.19 mmol) in DCM (41 mL) cooled to 0° C. were added DMF (0.3 mL) and oxalyl dichloride (1.39 mL, 16.4 mmol). The reaction mixture was stirred at ambient temperature for 1 hour, then cooled to 0° C., and a solution of phenol (0.925 g, 9.83 mmol) and DIEA (4.28 mL, 24.6 mmol) in DCM (10 mL) was added slowly. The reaction mixture was slowly warmed to ambient temperature and stirred for 2 hours, then was diluted with DCM (20 mL) and sat. aq. NaHCO$_3$ (60 mL) The phases were separated and the aqueous phase was extracted with DCM (3×70 mL), and the combined organic phases were dried over MgSO$_4$, filtered and concentrated. The crude product was purified by silica column chromatography, eluting with 0-50% acetone in hexanes to afford the title compound as an amber syrup (391 mg, 24% yield). $^1H$ NMR (CDCl$_3$) δ 7.39 (t, 2H), 7.25 (t, 1H), 7.11 (d, 2H), 2.68 (m, 1H), 2.20 (m, 1H), 1.89 (m, 1H).

Step B: Preparation of 1-(3-(2,2-difluorocyclopropyl)-1-phenyl-1H-pyrazol-5-yl)-3-(1',4-dimethyl-1-phenyl-1H,1'H-[3,4'-bipyrazol]-5-yl)urea Prepared according to the procedure of Example 6, replacing ethyl 2,2,2-trifluoroacetate with phenyl 2,2-difluorocyclopropanecarboxylate (391 mg, 1.97 mmol) and replacing propionitrile with acetonitrile (0.124 mL, 2.17 mmol) in Step A, to afford the title compound as a white solid (26.7 mg, 10% yield). MS (apci) m/z=515.2 (M+H).

Example 8 (Representative Compound)

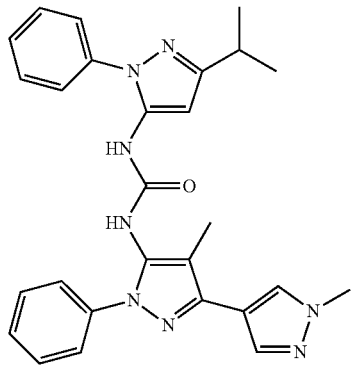 [SMILES: Cc1c(-c2cnn(C)c2)nn(-c2ccccc2)c1NC(=O)Nc1cc(C(C)C)nn1-c1ccccc1]

1-(1',4-dimethyl-1-phenyl-1H,1'H-[3,4'-bipyrazol]-5-yl)-3-(3-isopropyl-1-phenyl-1H-pyrazol-5-yl)urea Prepared according to the procedure of Example 6, Step C, replacing 4-methyl-1-phenyl-3-(trifluoromethyl)-1H-pyrazol-5-amine with 3-isopropyl-1-phenyl-1H-pyrazol-5-amine (Oakwood, 26 mg, 0.13 mmol), replacing DIEA with Et₃N, and replacing DMF with DCM. The reaction mixture was purified by silica column chromatography, eluting with 0-3% MeOH in DCM, to afford the title compound as a white solid (4 mg, 10% yield). MS (apci) m/z=481.2 (M+H).

Example 9 (Representative Compound)

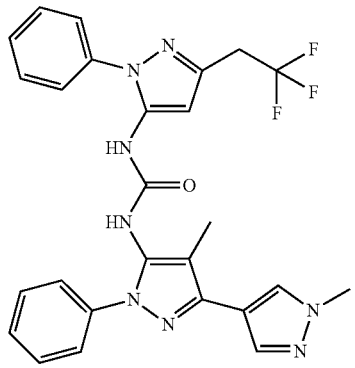 [SMILES: Cc1c(-c2cnn(C)c2)nn(-c2ccccc2)c1NC(=O)Nc1cc(CC(F)(F)F)nn1-c1ccccc1]

1-(1',4-dimethyl-1-phenyl-1H,1'H-[3,4'-bipyrazol]-5-yl)-3-(1-phenyl-3-(2,2,2-trifluoroethyl)-1H-pyrazol-5-yl)urea Step A: Preparation of 5,5,5-trifluoro-3-oxopentanenitrile To a stirred solution of 2-cyanoacetic acid (1.16 g, 13.7 mmol) and 2,2'-bipyridyl (5 mg) in THF (80 mL) cooled to −78° C. was added n-BuLi (2.5 M in hexanes, 10.9 mL, 27.3 mmol) dropwise until a pink color persisted. The temperature was raised to −10° C., then the remainder of the n-BuLi was added dropwise to maintain the pink color. The reaction mixture was cooled to −78° C., 3,3,3-trifluoropropanolyl chloride (1.00 g, 6.83 mmol) was added, and the reaction was stirred at −78° C. for 3 hours, and then quenched by the addition of water. The mixture was partitioned between Et₂O and 1 N HCl. The aqueous layer was extracted with Et₂O. The combined organic layers were washed with brine, dried and concentrated. The crude product was purified by silica column chromatography, eluting with 15% EtOAc in hexanes, to afford the title compound (0.790 g, 77%). ¹H NMR (CDCl₃) δ 3.63 (s, 2H), 3.46 (q, 2H).

Step B: Preparation of 1-(1',4-dimethyl-1-phenyl-1H,1'H-[3,4'-bipyrazol]-5-yl)-3-(1-phenyl-3-(2,2,2-trifluoroethyl)-1H-pyrazol-5-Aurea Prepared according to the procedure of Example 6, Steps B-C, replacing 4,4,4-trifluoro-2-methyl-3-oxobutanenitrile with 5,5,5-trifluoro-3-oxopentanenitrile (0.400 g, 2.64 mmol) in Step B and replacing DIEA with Et₃N, and replacing DMF with DCM in Step C. The reaction mixture was purified by reverse-phase column chromatography, eluting with 0-80% acetonitrile/water, to afford the title compound as a white solid (18 mg, 26% yield). MS (apci) m/z=521.2 (M+H).

Example 10 (Representative Compound)

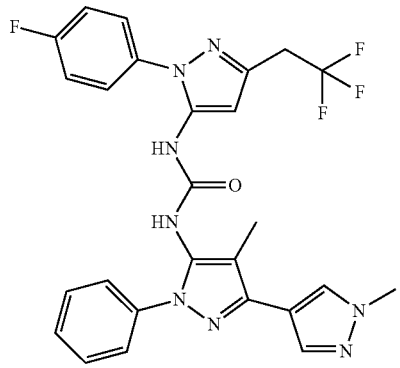 [SMILES: Cc1c(-c2cnn(C)c2)nn(-c2ccccc2)c1NC(=O)Nc1cc(CC(F)(F)F)nn1-c1ccc(F)cc1]

1-(1',4-dimethyl-1-phenyl-1H,1'H-[3,4'-bipyrazol]-5-yl)-3-(1-(4-fluorophenyl)-3-(2,2,2-trifluoroethyl)-1H-pyrazol-5-yl)urea Prepared according to the procedure of Example 9, replacing phenylhydrazine hydrochloride with (4-fluorophenyl)hydrazine hydrochloride (0.450 g, 2.77 mmol) in Step B. The reaction mixture was purified by reverse-phase column chromatography, eluting with 0-80% acetonitrile/water, to afford the title compound as a white solid (4 mg, 6% yield). MS (apci) m/z=539.2 (M+H).

Example 11

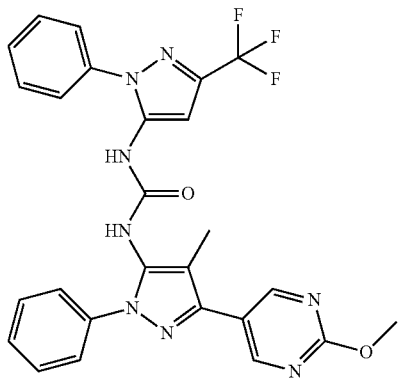 [SMILES: COc1ncc(-c2nn(-c3ccccc3)c(NC(=O)Nc3cc(C(F)(F)F)nn3-c3ccccc3)c2C)cn1]

1-(3-(2-methoxypyrimidin-5-yl)-4-methyl-1-phenyl-1H-pyrazol-5-yl)-3-(1-phenyl-3-(trifluoromethyl)-1H-pyrazol-5-yl)urea

Step A: phenyl (1-phenyl-3-(trifluoromethyl)-1H-pyrazol-5-yl)carbamate

To a solution of 1-phenyl-3-(trifluoromethyl)-1H-pyrazol-5-amine (200 mg, 0.880 mmol) in EtOAc (8 mL) was added aqueous NaOH (2M, 0.88 mL, 1.76 mmol) followed by addition of phenylchloroformate (0.13 mL, 1.06 mmol). The reaction mixture was stirred at ambient temperature for 18 hours, then additional phenylchloroformate (0.04 mL, 0.32 mmol) was added and the reaction mixture was stirred at ambient temperature for 2 hours. The reaction mixture was transferred to a separatory funnel with 10 mL EtOAc, the phases were separated, and the organic phase was washed with water and brine, dried (MgSO$_4$), filtered and concentrated. The crude solid was purified by silica column chromatography eluting with 0-40% EtOAc/hexane, to afford the title compound (221 mg, 72% yield) as a yellow solid. MS (apci) m/z=348.1 (M+H).

Step B: 1-(3-(2-methoxypyrimidin-5-yl)-4-methyl-1-phenyl-1H-pyrazol-5-yl)-3-(1-phenyl-3-(trifluoromethyl)-1H-pyrazol-5-yl)urea Phenyl (1-phenyl-3-(trifluoromethyl)-1H-pyrazol-5-yl)carbamate (40 mg, 0.12 mmol) and 3-(2-methoxypyrimidin-5-yl)-4-methyl-1-phenyl-1H-pyrazol-5-amine (Intermediate A, 32 mg, 0.12 mmol) were diluted with i-PrOH (1 mL). The suspension was heated to 50° C. for 42 hours and then heated to 80° C. for 2 hours. The reaction mixture was purified by reverse-phase column chromatography, eluting with 5-95% acetonitrile/water, and then purified by silica column chromatography eluting with 0-95% EtOAc/hexane, to afford the title compound as a white solid (2.2 mg, 4% yield). MS (apci) m/z=535.2 (M+H).

Example 12

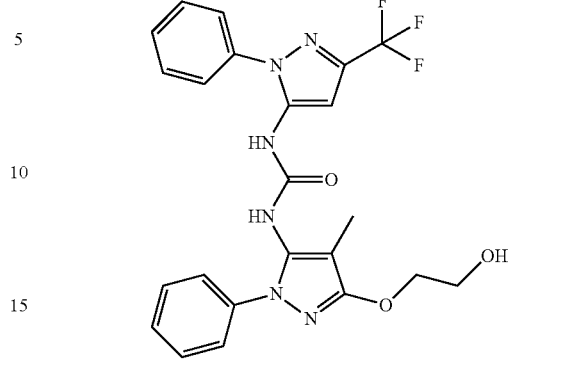

1-(3-(2-hydroxyethoxy)-4-methyl-1-phenyl-1H-pyrazol-5-yl)-3-(1-phenyl-3-(trifluoromethyl)-1H-pyrazol-5-yl)urea

Step A: 1-(3-(2-((tert-butyldimethylsilyl)oxy)ethoxy)-4-methyl-1-phenyl-1H-pyrazol-5-yl)-3-(1-phenyl-3-(trifluoromethyl)-1H-pyrazol-5-yl)urea Prepared according to the procedure of Example 11, Step B, replacing 3-(2-methoxypyrimidin-5-yl)-4-methyl-1-phenyl-1H-pyrazol-5-amine with 3-(2-((tert-butyldimethylsilyl)oxy)ethoxy)-4-methyl-1-phenyl-1H-pyrazol-5-amine (Intermediate B). The reaction mixture was partially concentrated, then purified by silica column chromatography eluting with 0-50% EtOAc/hexane, to afford the title compound as a white solid (4.2 mg, 6% yield). MS (apci) m/z=601.2 (M+H).

Step B: 1-(3-(2-hydroxyethoxy)-4-methyl-1-phenyl-1H-pyrazol-5-yl)-3-(1-phenyl-3-(trifluoromethyl)-1H-pyrazol-5-yl)urea To a solution of 1-(3-(2-((tert-butyldimethylsilyl)oxy)ethoxy)-4-methyl-1-phenyl-1H-pyrazol-5-yl)-3-(1-phenyl-3-(trifluoromethyl)-1H-pyrazol-5-yl)urea (4.2 mg, 0.007 mmol) in EtOH (1.5 mL) was added HCl (5-6 M in i-PrOH, 0.005 mL). The reaction mixture was stirred at ambient temperature for 1 hour and then concentrated. The crude solid was diluted with Et$_2$O (2×1 mL) and concentrated after each addition to give the title compound as a white solid (3.6 mg, 106% yield). MS (apci) m/z=487.2 (M+H).

What is claimed is:

1. A compound of Formula I:

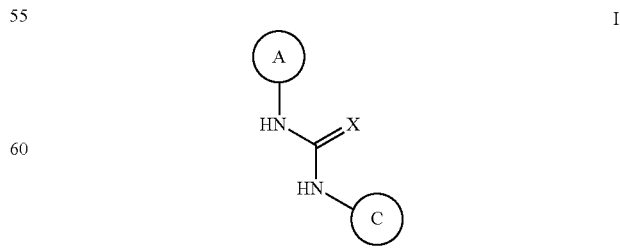

or stereoisomers, tautomers, or pharmaceutically acceptable salts, solvates or prodrugs thereof, wherein:
X is O, S, NH or N—CN;

Ring A is

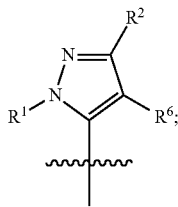

R¹ is phenyl optionally substituted with one or more substituents independently selected from halogen and (1-3C)alkyl;
R² is (1-3C)alkyl optionally substituted with 1 to 5 fluoros or (3-4C)cycloalkyl optionally substituted with one or two fluoros;
R⁶ is H or CH₃;
Ring C is formula C-1

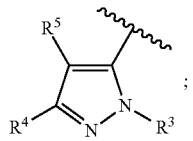

R³ is (1-6C)alkyl, hydroxy(1-6C)alkyl, Ar², hetCyc¹, (3-7C)cycloalkyl, or hetAr²;
Ar² is phenyl optionally substituted with one or more substituents independently selected from halogen and (1-6C)alkyl;
hetCyc¹ is a 5-6-membered saturated or partially unsaturated heterocyclic ring having 1-2 ring heteroatoms independently selected from N and O;
hetAr² is a 5-6 membered heteroaryl ring having 1-3 ring heteroatoms independently selected from N, O and S and optionally substituted with one or more substituents independently selected from (1-6C)alkyl and halogen;
R⁴ is hetAr⁴, hetAr⁵ or hydroxy(1-6C)alkoxy;
hetAr⁴ is a 5-6 membered heteroaryl ring having 1-3 ring heteroatoms independently selected from N, S and O and substituted with one or more substituents independently selected from (1-6C)alkyl, halogen, CN, hydroxy(1-6C)alkyl, trifluoro(1-6C)alkyl, difluoro(1-6C)alkyl, fluoro(1-6C)alkyl, (3-6C)cycloalkyl, (3-6C cycloalkyl)CH₂— (3-6C cycloalkyl)C(=O)—, (1-3C alkoxy)(1-6C)alkyl, (1-6C)alkoxy, (1-6C)alkylsulfonyl, NH₂, (1-6C alkyl)amino, di(1-6C alkyl)amino, (1-3C trifluoroalkoxy), fluoro(1-6C alkyl)amino, difluoro(1-6C alkyl)amino, trifluoro(1-6C alkyl)amino, and (3-4C cycloalkyl)amino;
hetAr⁵ is a group selected from the structures:

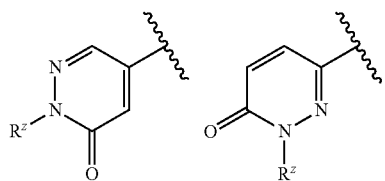

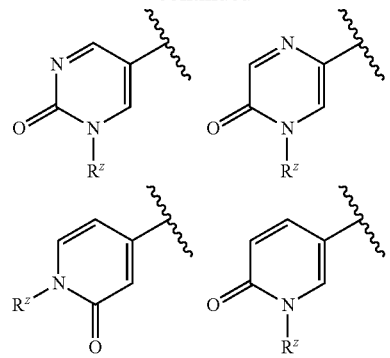

where R^z is (3-4C)cycloalkyl or (1-3C)alkyl optionally substituted with 1-3 fluoros, wherein each of said hetAr⁵ groups is optionally further substituted with one or more substituents independently selected from F and (1-3C)alkyl optionally substituted with 1-3 fluoros; and
R⁵ is (1-6C)alkyl, monofluoro(1-6C)alkyl, difluoro(1-6C)alkyl, trifluoro(1-6C)alkyl, tetrafluoro(2-6C)alkyl, pentafluoro(2-6C)alkyl, halogen, CN, (1-4C)alkoxy, hydroxy(1-4C)alkyl, (1-3C alkoxy)(1-4C)alkyl, (1-4C alkyl)OC(=O)—, (1-6C)alkylthio, (3-4C)cycloalkyl, amino, aminocarbonyl, trifluoro(1-3C alkyl)amido, or phenyl optionally substituted with one or more substituents independently selected from halogen, (1-6C)alkyl and (1-6C)alkoxy; or
R⁴ and R⁵ together with the atoms to which they are attached form a 5-6 membered saturated, partially unsaturated or unsaturated carbocyclic ring optionally substituted with one or more substituents independently selected from (1-6C)alkyl, or
R⁴ and R⁵ together with the atoms to which they are attached form 5-6 membered saturated, partially unsaturated or unsaturated heterocyclic ring having a ring heteroatom selected from N, O or S, wherein said heterocyclic ring is optionally substituted with one or two substituents independently selected from (1-6C alkyl)C(=O)O—, (1-6C)acyl, (1-6C)alkyl and oxo, and said sulfur ring atom is optionally oxidized to S(=O) or SO₂.

2. A compound according to claim 1, wherein X is O.
3. A compound according to claim 1, wherein R¹ is phenyl.
4. A compound according to claim 1, wherein R² is (3-4C)cycloalkyl optionally substituted with one or two fluoros.
5. A compound according to claim 1, wherein R⁴ is hetAr⁴ or hetAr⁵; and
R⁵ is (1-6C)alkyl, monofluoro(1-6C)alkyl, difluoro(1-6C)alkyl, trifluoro(1-6C)alkyl, tetrafluoro(2-6C)alkyl, pentafluoro(2-6C)alkyl, halogen, CN, (1-4C)alkoxy, hydroxy(1-4C)alkyl, (1-3C alkoxy)(1-4C)alkyl, (1-4C alkyl)OC(=O)—, (1-6C)alkylthio, (3-4C)cycloalkyl, amino, aminocarbonyl, trifluoro(1-3C alkyl)amido, or phenyl optionally substituted with one or more substituents independently selected from halogen, (1-6C)alkyl and (1-6C)alkoxy.
6. The compound according to claim 5, wherein R⁴ is hetAr⁴.
7. The compound according to claim 6, wherein R⁴ is pyrazole optionally substituted with one or more substituents independently selected from (1-6C)alkyl.

8. The compound according to claim 5, wherein $R^4$ is hetAr⁵.

9. A compound according to claim 1, wherein $R^4$ is hydroxyl(1-6C)alkoxy; and $R^5$ is (1-6C)alkyl, monofluoro(1-6C)alkyl, difluoro(1-6C)alkyl, trifluoro(1-6C)alkyl, tetrafluoro(2-6C)alkyl, pentafluoro(2-6C)alkyl, halogen, CN, (1-4C)alkoxy, hydroxy(1-4C)alkyl, (1-3C alkoxy)(1-4C)alkyl, (1-4C alkyl)OC(=O)—, (1-6C)alkylthio, (3-4C)cycloalkyl, amino, aminocarbonyl, trifluoro(1-3C alkyl)amido, or phenyl optionally substituted with one or more substituents independently selected from halogen, (1-6C)alkyl and (1-6C)alkoxy.

10. The compound according to claim 1, wherein $R^5$ is (1-6C)alkyl.

11. A compound according to claim 1, wherein $R^3$ is $Ar^2$.

12. A compound according to claim 11, wherein $R^3$ is phenyl.

13. A compound according to claim 1, selected from

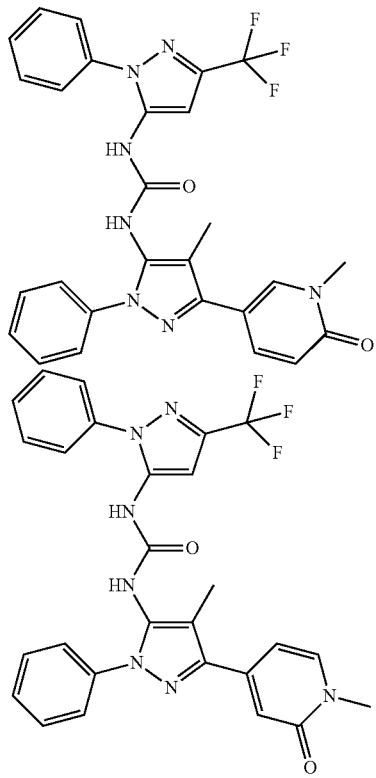

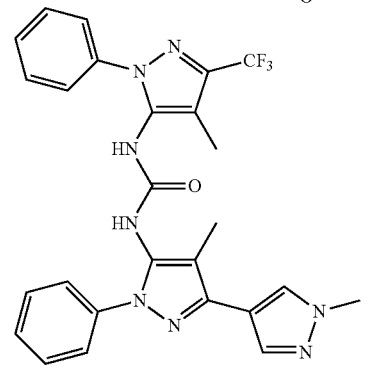

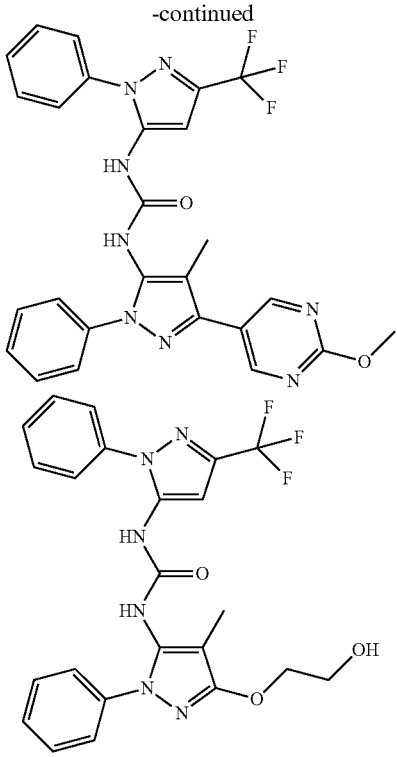

or a pharmaceutically acceptable salt thereof.

14. A pharmaceutical composition, which comprises a compound of Formula I as defined in claim 1 or a pharmaceutically acceptable salt thereof, and a pharmaceutically acceptable diluent or carrier.

15. A method of treating dysregulation of TrKA associated with pain or glioblastoma multiforme a in a mammal, which comprises administering to said mammal a therapeutically effective amount of a compound of Formula I as defined in claim 1 or pharmaceutically acceptable salt thereof.

16. The method of claim 15, wherein the method is a method for treating pain.

17. The method of claim 15, wherein the method is a method for treating glioblastoma multiforme.

18. A process for the preparation of a compound of claim 1, which comprises:
(a) for a compound of Formula I where X is O, coupling a corresponding compound having the formula II

II with a corresponding compound having the formula III

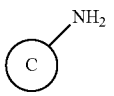

III in the presence carbonyldiimidazole or triphosgene and a base; or (b) for a compound of Formula I where X is S, coupling a corresponding compound having the formula II

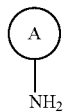

with a corresponding compound of formula III

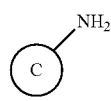

in the presence di(1H-imidazol-2-yl)methanethione and a base; or (c) for a compound of Formula I where X is O, coupling a corresponding compound having the formula II

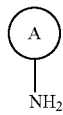

with a corresponding compound having the formula IV

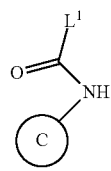

where $L^1$ is a leaving group, in the presence of a base; or (d) for a compound of Formula I where X is O, coupling a corresponding compound having the formula V

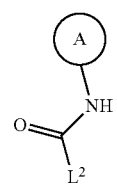

where $L^2$ is a leaving group, with a corresponding compound having the formula III

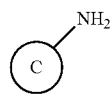

in the presence of a base; or (e) for a compound of Formula I where X is O, activating a corresponding compound having the formula VI

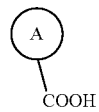

with diphenylphosphoryl azide followed by coupling the activated intermediate with a corresponding compound having the formula III

in the presence a base; or (f) for a compound of Formula I where X is O, coupling a corresponding compound having the formula II

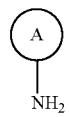

with a corresponding compound having the formula VII

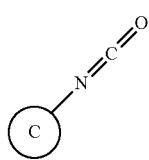

in the presence of a base;

or (g) for a compound of Formula I where X is O, coupling a corresponding compound having the formula VIII

with a corresponding compound having the formula III

in the presence of a base; and optionally removing protecting groups and optionally preparing a pharmaceutically acceptable salt thereof.

* * * * *

UNITED STATES PATENT AND TRADEMARK OFFICE
CERTIFICATE OF CORRECTION

PATENT NO.         : 9,809,578 B2
APPLICATION NO.    : 14/442495
DATED              : November 7, 2017
INVENTOR(S)        : Barbara J. Brandhuber et al.

Page 1 of 1

It is certified that error appears in the above-identified patent and that said Letters Patent is hereby corrected as shown below:

In the Claims

Column 71, Lines 44, Claim 18, please delete "where $L^i$ is a leaving" and insert -- where $L^1$ is a leaving -- therefor.

Signed and Sealed this
Fifteenth Day of May, 2018

Andrei Iancu
*Director of the United States Patent and Trademark Office*